(12) United States Patent
Taishi et al.

(10) Patent No.: US 7,919,623 B2
(45) Date of Patent: *Apr. 5, 2011

(54) NAPHTHYRIDINE DERIVATIVES HAVING INHIBITORY ACTIVITY AGAINST HIV INTEGRASE

(75) Inventors: Teruhiko Taishi, Osaka (JP); Yukio Tada, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 1285 days.

This patent is subject to a terminal disclaimer.

(21) Appl. No.: 10/587,857

(22) PCT Filed: Feb. 2, 2005

(86) PCT No.: PCT/JP2005/001454
§ 371 (c)(1),
(2), (4) Date: Jul. 28, 2006

(87) PCT Pub. No.: WO2005/075475
PCT Pub. Date: Aug. 18, 2005

(65) Prior Publication Data
US 2009/0227621 A1  Sep. 10, 2009

(30) Foreign Application Priority Data
Feb. 4, 2004 (JP) .................. 2004-027849

(51) Int. Cl.
C07D 471/02 (2006.01)
(52) U.S. Cl. ....................................... 546/123
(58) Field of Classification Search .................. 546/123
See application file for complete search history.

(56) References Cited

U.S. PATENT DOCUMENTS

| | | | |
|---|---|---|---|
| 6,211,376 B1 | 4/2001 | Romines et al. | |
| 6,252,080 B1 | 6/2001 | Thaisrivongs et al. | |
| 6,310,211 B1 | 10/2001 | Vaillancourt et al. | |
| 7,358,249 B2 * | 4/2008 | Murai et al. | 514/234.5 |
| 2003/0055071 A1 | 3/2003 | Anthony et al. | |
| 2006/0128669 A1 * | 6/2006 | Murai et al. | 514/81 |

FOREIGN PATENT DOCUMENTS

| | | |
|---|---|---|
| JP | 2002-505660 | 2/2002 |
| WO | 2002/030931 | 4/2002 |
| WO | 2004/024693 | 3/2004 |
| WO | WO2004/0424693 | * 3/2004 |

OTHER PUBLICATIONS

Andrea Savarino, A Historical Sketch of the Discovery and Development of HIV-1 Integrase Inhibitors, 15 Expert Opin. Investig. Drugs 1507 (2006).*
Fatima Zouhiri, et al, Structure-Activity Relationships and Binding Mode of Styrylquinolines as Potent Inhibitors of HIV-1 Integrase and Replication of HIV-1 in Cell Culture, 43 J Med. Chem. 1533 (2000).*
Ya-Qiu Long, et al, Rational Design and Synthesis of Novel Dimeric Diketoacid-Containing Inhibitors of HIV-1 Integrase: Implication for Binding to Two Metal Ions on the Active Site of Integrase, 47 J Med. Chem. 2561 (2004).*

* cited by examiner

*Primary Examiner* — Jeffrey S. Lundgren
*Assistant Examiner* — Sean Basquill
(74) *Attorney, Agent, or Firm* — Wenderoth, Lind and Ponack, L.L.P.

(57) ABSTRACT

A compound having HIV Integrase Inhibitory activity of the formula:

[Formula 1]

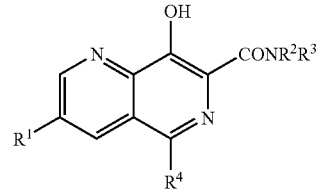

(I)

(wherein:
$R^1$ is optionally substituted aralkyl;
$R^2$ and $R^3$ are each independently hydrogen, optionally substituted alkyl, optionally substituted amino, optionally substituted alkenyl or optionally substituted alkoxy (provided that each substituent for "optionally substituted" is a non-cyclic group);
$R^4$ is hydrogen, optionally substituted carboxy, optionally substituted formylamino, optionally substituted carbamoyl, optionally substituted amino (provided that a substituent on amino in "optionally substituted formylamino", "optionally substituted carbamoyl" and "optionally substituted amino" may form an optionally-substituted N-atom containing heterocyclic ring together with an adjacent N atom), optionally substituted alkyl, optionally substituted alkenyl, optionally substituted aryl, or optionally substituted heteroaryl) or a salt thereof.

6 Claims, No Drawings

NAPHTHYRIDINE DERIVATIVES HAVING INHIBITORY ACTIVITY AGAINST HIV INTEGRASE

TECHNICAL FIELD

The present invention relates to novel compounds having antiviral activities, in detail naphthyridine derivatives having inhibitory activity against HIV integrase and a pharmaceutical composition, especially an anti-HIV agent, containing the same.

BACKGROUND ART

Among viruses, human immunodeficiency virus (HIV), a kind of retrovirus, is known to cause acquired immunodeficiency syndrome (AIDS). The therapeutic agent for AIDS is mainly selected from a group of reverse transcriptase inhibitors (e.g., AZT, 3TC) and protease inhibitors (e.g., Indinavir), but they are proved to be accompanied by side effects such as nephropathy and the emergence of resistant viruses. Thus, the development of anti-HIV agents having the other mechanism of action has been desired.

On the other hand, a multidrug combination therapy is reported to be efficient in treatment for acquired immunodeficiency syndrome (AIDS) because of the frequent emergence of the resistant mutant. Reverse transcriptase inhibitors and protease inhibitors are clinically used as an anti-HIV agent, however agents having the same mechanism of action often exhibit cross-resistance or only an additional activity. Therefore, anti-HIV agents having the other mechanism of action are desired.

As a compound having inhibitory activity against HIV integrase, 1,6-naphthyridine derivative is known (see Patent documents 1 to 7). The derivative has a cyclic group such as aryl or heteroaryl at 7-position of side chain end.

Also a 1,6-naphthyridine derivative having a similar structure to the compound of the present invention was internationally filed by the present applicant (see Patent document 8).

[Patent document 1]
WO 2002/30426
[Patent document 2]
WO 2002/30930
[Patent document 3]
WO 2002/30931
[Patent document 4]
WO 2002/36734
[Patent document 5]
WO 2002/44079
[Patent document 6]
WO2003/77850
[Patent document 7]
WO2003/77857
[Patent document 8]
PCT/JP 03/10212

Under the above circumstance, the development of a novel integrase inhibitor has been desired.

DISCLOSURE OF INVENTION

The present inventors have intensively studied to find that a novel naphthyridine derivative has a strong inhibitory activity against HIV integrase. Moreover, the present inventors have discovered that a compound of the present invention and a pharmaceutical composition containing the same are useful as an antiviral agent (e.g., an antiretroviral agent, an anti-HIV agent, an anti-HTLV-1 (Human T cell leukemia virus type 1) agent, an anti-FIV (Feline immunodeficiency virus) agent or an anti-SIV (Simian immunodeficiency virus) agent), especially an anti-HIV agent or, an anti-AIDS agent, pharmaceutical agents for related diseases and the like, to accomplish the present invention.

Specifically, the present invention relates to the following inventive features:

(1) A compound of the formula:

[Formula 1]

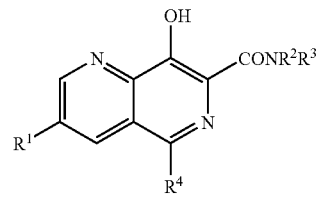

(I)

(wherein:
$R^1$ is optionally substituted aralkyl;
$R^2$ and $R^3$ are each independently hydrogen, optionally substituted alkyl, optionally substituted amino, optionally substituted alkenyl or optionally substituted alkoxy (provided that each substituent for "optionally substituted" is a non-cyclic group);
$R^4$ is hydrogen, optionally substituted carboxy, optionally substituted formylamino, optionally substituted carbamoyl, optionally substituted amino (provided that a substituent on amino in "optionally substituted formylamino", "optionally substituted carbamoyl" and "optionally substituted amino" may form an optionally-substituted N-atom containing heterocyclic ring together with an adjacent N atom), optionally substituted alkyl, optionally substituted alkenyl, optionally substituted aryl, or optionally substituted heteroaryl), a pharmaceutically acceptable salt or a solvate thereof (except for Compound (I-A) shown in Table 1 below).

TABLE 1

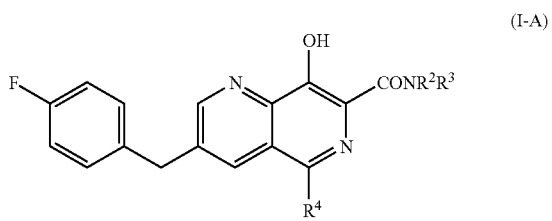

(I-A)

| Compound No. | $R^2$ | $R^3$ | $R^4$ |
|---|---|---|---|
| 20 | H | CH2CH2OMe | H |
| 27 | H | Me | NHMs |
| 28 | H | CH2CH2OMe | NHMs |
| 29 | H | i-Pr | NHMs |
| 85 | Me | Me | H |
| 86 | H | NHMe | H |
| 87 | H | NMe2 | H |
| 88 | H | OMe | H |
| 89 | H | H | H |
| 90 | H | Me | H |
| 91 | H | Et | H |
| 92 | H | i-Pr | H |
| 126 | H | CH2CH2NMe2 | H |
| 160 | H | CH2CH2OMe | NHCOCH2OMe |
| 161 | H | CH2CH2OMe | NHCOCH2CH2CO2Et |

TABLE 1-continued

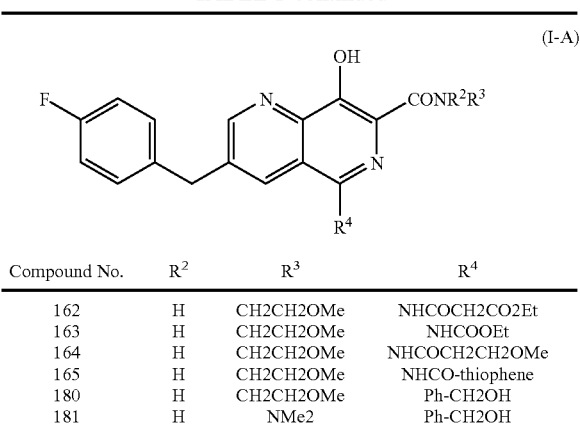

(I-A)

| Compound No. | R² | R³ | R⁴ |
|---|---|---|---|
| 162 | H | CH2CH2OMe | NHCOCH2CO2Et |
| 163 | H | CH2CH2OMe | NHCOOEt |
| 164 | H | CH2CH2OMe | NHCOCH2CH2OMe |
| 165 | H | CH2CH2OMe | NHCO-thiophene |
| 180 | H | CH2CH2OMe | Ph-CH2OH |
| 181 | H | NMe2 | Ph-CH2OH |

(Me = methyl; i-Pr = isopropyl; Et = ethyl; Ms = methanesulfonyl; thiophene = thiophene; Ph = phenyl)

The above Compound (I-A) is an exemplary amide-type compound having a 1,6-naphthyridine scaffold disclosed in PCT/JP03/10212.

(2) The compound according to the above (1), wherein R¹ is p-fluorobenzyl, a pharmaceutically acceptable salt or a solvate thereof.

(3) The compound according to the above (1), wherein R² is hydrogen; R³ is optionally substituted alkyl (substituent: lower alkoxy, amino optionally substituted with lower alkyl, cyano, hydroxy, carboxy, or lower alkoxycarbonyl), or optionally substituted amino (substituent: lower alkyl), a pharmaceutically acceptable salt or a solvate thereof.

(4) The compound according to the above (1), wherein R² is hydrogen; R³ is CH₂CH₂OCH₃, CH₂CH₂OEt, CH₂CH₂COOCH₃, CH₂CH₂CH₂OCH₃, CH₂CH₂CH₂O(i-Pr), N(CH₃)₂, CH₂CH₂CN, CH₂CH₂N(CH₃)₂, CH₂CH₂N(i-Pr)₂, CH₂CH₂CH₂N(CH₃)₂, CH₂CH₂CH₂N(Et)₂, CH(CH₃)CH₂OH, CH(CH₃)COOCH₃ or CH₂CH(OH)CH₂CH₃, a pharmaceutically acceptable salt or a solvate thereof.

(5) The compound according to the above (1), wherein R⁴ is optionally substituted carboxy, optionally substituted carbamoyl (provided that the substituent on amino may form an optionally-substituted N-atom containing heterocyclic ring together with an adjacent N atom), optionally substituted formylamino, optionally substituted alkyl, optionally substituted alkenyl or optionally substituted heteroaryl, a pharmaceutically acceptable salt or a solvate thereof.

(6) The compound according to the above (1), wherein in R⁴,
a substituent for "optionally substituted carboxy" is lower alkyl, hydroxy lower alkyl, lower alkoxy lower alkyl, optionally substituted amino lower alkyl, or optionally substituted heterocyclic group;

a substituent for "optionally substituted formylamino" is lower alkyl, hydroxy lower alkyl, lower alkoxy lower alkyl, optionally substituted carbamoyl lower alkyl, optionally substituted lower alkoxy, optionally substituted amino, or optionally substituted carbamoyl;

a substituent for "optionally substituted carbamoyl" is lower alkyl, optionally substituted lower alkyl (substituent: hydroxy, lower alkoxy, optionally substituted amino, optionally substituted lower alkoxy, carbamoyl), optionally substituted heterocyclic group, optionally substituted heterocyclic group lower alkyl, optionally substituted aryl, optionally substituted aryloxy lower alkyl, optionally substituted aralkyl, optionally substituted carbamoyl lower alkyl, optionally substituted lower alkoxy, optionally substituted amino, optionally substituted alkenyl, or optionally substituted alkynyl;

a substituent for "optionally substituted amino" is lower alkyl, hydroxy lower alkyl, lower alkoxy lower alkyl, optionally substituted heterocyclic group, or optionally substituted carbamoyl lower alkyl;

a substituent for "optionally substituted alkyl" or "optionally substituted alkenyl" is hydroxy, halogen, optionally substituted heterocyclic group, optionally substituted lower alkoxy, optionally substituted amino, optionally substituted carbamoyl, or optionally substituted carboxy;

a substituent for "optionally substituted aryl" or "optionally substituted heteroaryl" is hydroxy, lower alkyl, hydroxy lower alkyl, lower alkoxy lower alkyl, optionally substituted aminoalkyl, optionally substituted carbamoyl lower alkyl, optionally substituted lower alkoxy, optionally substituted amino, optionally substituted carbamoyl, optionally substituted alkenyl, optionally substituted carboxy, optionally substituted carboxyalkyl, optionally substituted salfamoyl, or optionally substituted salfamoylalkyl (provided that a substituent on amino in "optionally substituted formylamino", "optionally substituted amino" or "optionally substituted carbamoyl" may form an optionally-substituted N-atom containing heterocyclic ring together with an adjacent N atom), a pharmaceutically acceptable salt or a solvate thereof.

(7) The compound according to the above (1), wherein R⁴ is a group shown below, a pharmaceutically acceptable salt or a solvate thereof.

[Formula 2]

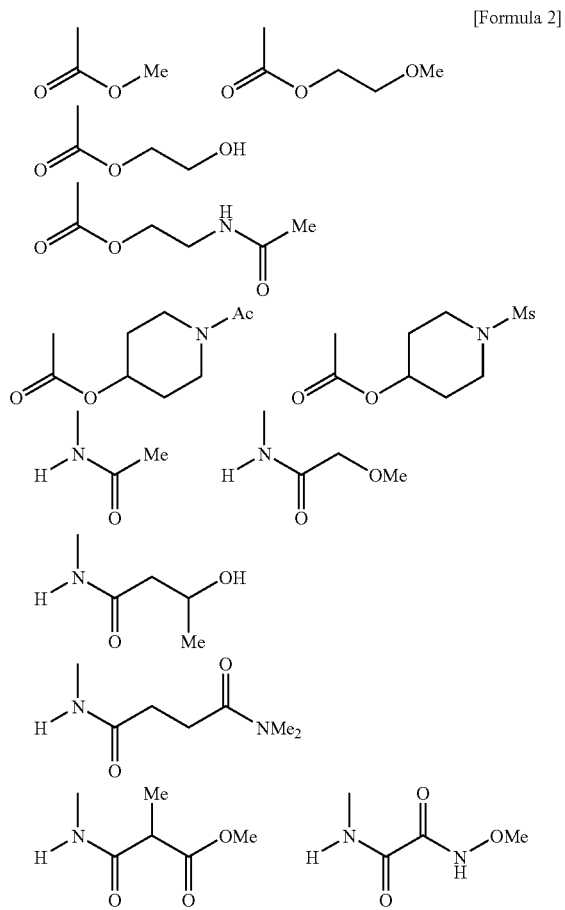

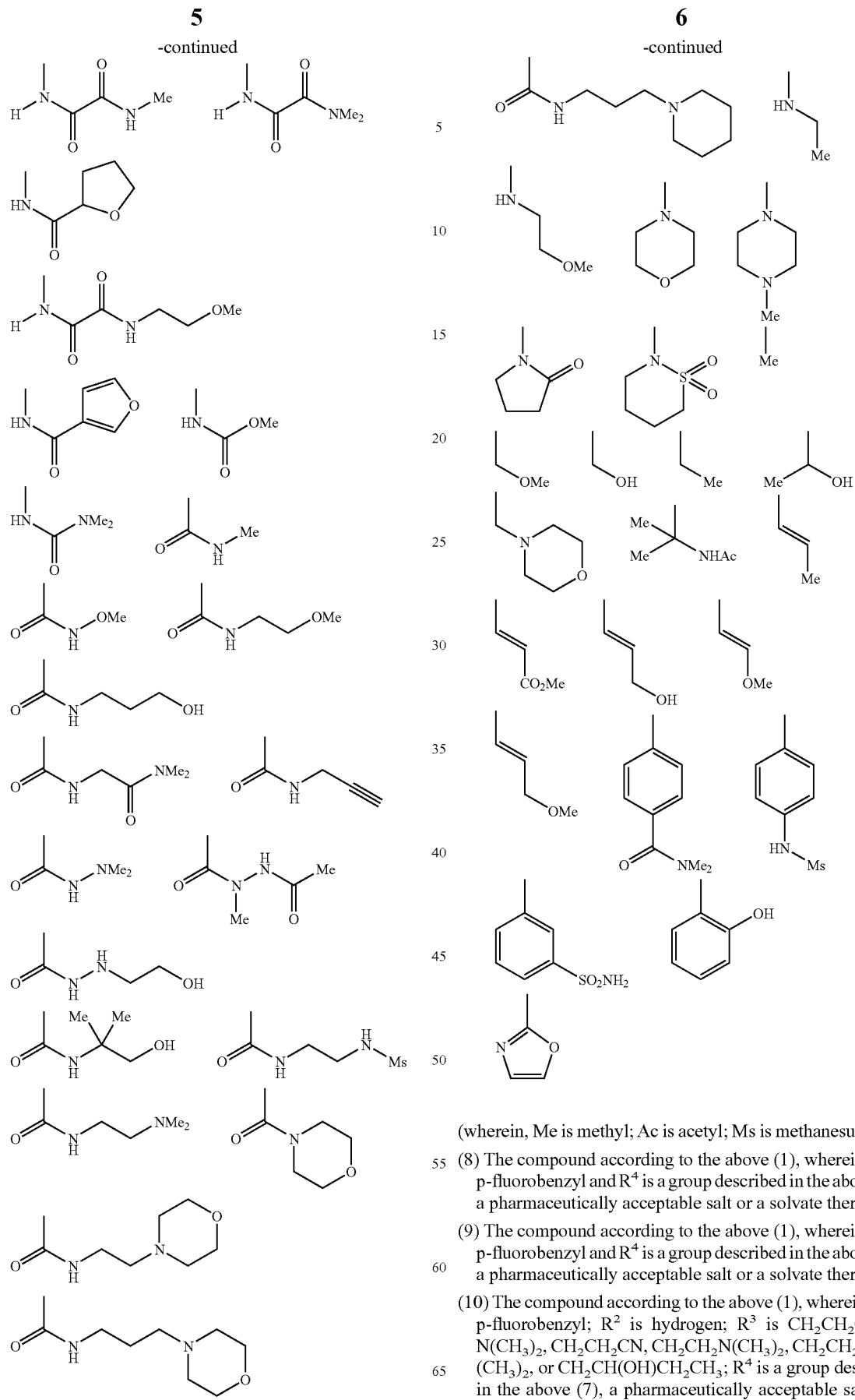

(wherein, Me is methyl; Ac is acetyl; Ms is methanesulfonyl)

(8) The compound according to the above (1), wherein $R^1$ is p-fluorobenzyl and $R^4$ is a group described in the above (5), a pharmaceutically acceptable salt or a solvate thereof.

(9) The compound according to the above (1), wherein $R^1$ is p-fluorobenzyl and $R^4$ is a group described in the above (7), a pharmaceutically acceptable salt or a solvate thereof.

(10) The compound according to the above (1), wherein $R^1$ is p-fluorobenzyl; $R^2$ is hydrogen; $R^3$ is $CH_2CH_2OCH_3$, $N(CH_3)_2$, $CH_2CH_2CN$, $CH_2CH_2N(CH_3)_2$, $CH_2CH_2CH_2N(CH_3)_2$, or $CH_2CH(OH)CH_2CH_3$; $R^4$ is a group described in the above (7), a pharmaceutically acceptable salt or a solvate thereof.

(11) A pharmaceutical composition comprising the compound according to any of the above (1) to (10), a pharmaceutically acceptable salt or a solvate thereof.

(12) A pharmaceutical composition according to the above (11), wherein it is a HIV integrase inhibitor.

EFFECT OF THE INVENTION

Compounds of the present invention have inhibitory activity against integrase, and/or have activity of inhibiting proliferation of viruses, especially HIV.

Therefore, they are useful for prophylaxis and therapy of a variety of integrase-related diseases, and viral infectious diseases (e.g., AIDS).

BEST MODE FOR CARRYING OUT THE INVENTION

The terms used in the present specification are explained as follows. Each term by itself or as part of another has the following meaning.

The term "alkyl" means preferably a C1-C10 straight or branched alkyl group, for example, methyl, ethyl, n-propyl, isopropyl, n-butyl, isobutyl, sec-butyl, tert-butyl, n-pentyl, isopentyl, neopentyl, tert-pentyl, n-hexyl, isohexyl, n-heptyl, n-octyl, n-nonyl or n-decyl. More preferred is a lower (C1-C6) alkyl group, and more preferred is a C1-C4 lower alkyl such as methyl, ethyl, n-propyl, isopropyl, n-butyl, isobutyl, sec-butyl, tert-butyl n-pentyl, isopentyl, neopentyl, tert-pentyl, n-hexyl or isohexyl.

The term "alkenyl" means a C2-C10 straight or branched alkenyl group which is the above "alkyl" having one or more double bonds, for example, vinyl, 1-propenyl, 2-propenyl, 1-butenyl, 2-butenyl, 3-butenyl, 1,3-butadienyl or 3-methyl-2-butenyl.

The term "cycloalkyl" means a C3-C10 cyclic saturated hydrocarbon group, for example, cyclopropyl, cyclobutyl, cyclopentyl, cyclohexyl, cycloheptyl, or cyclooctyl. Preferred is a C3-C6 cycloalkyl group.

An alkyl moiety of "alkoxy" has the same meanings as the above "alkyl", and includes methoxy, ethoxy, n-propoxy, isopropoxy, n-butoxy, isobutoxy, tert-butoxy and the like.

The term "aryl" means a monocyclic aromatic hydrocarbon group (e.g., phenyl) or a polycyclic aromatic hydrocarbon group (e.g., 1-naphthyl, 2-naphthyl, 1-antolyl, 2-antolyl, 9-antolyl, 1-phenantolyl, 2-phenantolyl, 3-phenantolyl, 4-phenantolyl or 9-phenantolyl). Preferred is phenyl or naphthyl (e.g., 1-naphthyl or 2-naphthyl).

The term "aralkyl" means the above "alkyl" to which "aryl" is bound, for example, benzyl, phenylthyl, phenylpropyl, α-naphthylmethyl or β-naphthylmethyl. Preferred is benzyl.

The term "heterocyclic group" means "heterocycle" or "heteroaryl".

The term "heterocycle" means a non-aromatic heterocyclic group (preferably 5 to 7-membered) which contains at least one of nitrogen atom, oxygen atom and sulfur atom, and which has a bonding position at any substitutable position, for example, 1-pyrrolinyl, 2-pyrrolinyl, 3-pyrrolinyl, 1-pyrrolidinyl, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidyl, 3-piperidyl, 4-piperidyl, 1-piperazinyl, 2-piperazinyl, 2-morpholinyl, 3-morpholinyl, morpholino or tetrahydropyranyl. Then, "a non-aromatic heterocyclic group" can be saturated or unsaturated insofar as it is non-aromatic.

The term "heteroaryl" means a monocyclic aromatic heterocyclic group and a condensed aromatic heterocyclic group.

A monocycle aromatic heterocyclic group means a group, which is derived from a 5- to 8-membered aromatic ring which may contain 1 to 4 of oxygen atom, sulfur atom, and/or nitrogen atom and which may have a bonding position at any substitutable position.

A condensed aromatic heterocyclic group means a group, wherein a 5- to 8-membered aromatic ring which may contain 1 to 4 of oxygen atom, sulfur atom, and/or nitrogen atom is condensed with 1 to 4 of 5- to 8-membered aromatic carbon ring or the other 5- to 8-membered aromatic hetero ring and which may have a bonding position at the any substitutable position.

The term "heteroaryl" means the following groups, for example, furyl (e.g., 2-furyl or 3-furyl), thienyl (e.g., 2-thienyl or 3-thienyl), pyrrolyl (e.g., 1-pyrrolyl, 2-pyrrolyl or 3-pyrrolyl), imidazolyl (e.g., 1-imidazolyl, 2-imidazolyl or 4-imidazolyl), pyrazolyl (e.g., 1-pyrazolyl, 3-pyrazolyl or 4-pyrazolyl), triazolyl (e.g., 1,2,4-triazol-1-yl, 1,2,4-triazol-3-yl or 1,2,4-triazol-4-yl), tetrazolyl (e.g., 1-tetrazolyl, 2-tetrazolyl or 5-tetrazolyl), oxazolyl (e.g., 2-oxazolyl, 4-oxazolyl or 5-oxazolyl), isoxazolyl (e.g., 3-isoxazolyl, 4-isoxazolyl or 5-isoxazolyl), thiazolyl (e.g., 2-thiazolyl, 4-thiazolyl or 5-thiazolyl), thiadiazolyl, isothiazolyl (e.g., 3-isothiazolyl, 4-isothiazolyl or 5-isothiazolyl), pyridyl (e.g., 2-pyridyl, 3-pyridyl or 4-pyridyl), pyridazinyl (e.g., 3-pyridazinyl or 4-pyridazinyl), pyrimidinyl (e.g., 2-pyrimidinyl, 4-pyrimidinyl or 5-pyrimidinyl), furazanyl (e.g., 3-furazanyl), pyrazinyl (e.g., 2-pyrazinyl), oxadiazolyl (e.g., 1,3,4-oxadiazol-2-yl), benzofuryl (e.g., 2-benzo[b]furyl, 3-benzo[b]furyl, 4-benzo[b]furyl, 5-benzo[b]furyl, 6-benzo[b]furyl or 7-benzo[b]furyl), benzothienyl (e.g., 2-benzo[b]thienyl, 3-benzo[b]thienyl, 4-benzo[b]thienyl, 5-benzo[b]thienyl, 6-benzo[b]thienyl or 7-benzo[b]thienyl), benzimidazolyl (e.g., 1-benzoimidazolyl, 2-benzoimidazolyl, 4-benzoimidazolyl or 5-benzoimidazolyl), dibenzofuryl, benzooxazolyl, quinoxalyl (e.g., 2-quinoxalinyl, 5-quinoxalinyl or 6-quinoxalinyl), cinnolinyl (e.g., 3-cinnolinyl, 4-cinnolinyl, 5-cinnolinyl, 6-cinnolinyl, 7-cinnolinyl or 8-cinnolinyl), quinazolyl (e.g., 2-quinazolinyl, 4-quinazolinyl, 5-quinazolinyl, 6-quinazolinyl, 7-quinazolinyl or 8-quinazolinyl), quinolyl (e.g., 2-quinolyl, 3-quinolyl, 4-quinolyl, 5-quinolyl, 6-quinolyl, 7-quinolyl or 8-quinolyl), phthalazinyl (e.g., 1-phthalazinyl, 5-phthalazinyl or 6-phthalazinyl), isoquinolyl (e.g., 1-isoquinolyl, 3-isoquinolyl, 4-isoquinolyl, 5-isoquinolyl, 6-isoquinolyl, 7-isoquinolyl or 8-isoquinolyl), puryl, pteridinyl (e.g., 2-pteridinyl, 4-pteridinyl, 6-pteridinyl or 7-pteridinyl), carbazolyl, phenantridinyl, acridinyl (e.g., 1-acridinyl, 2-acridinyl, 3-acridinyl, 4-acridinyl or 9-acridinyl), indolyl (e.g., 1-indolyl, 2-indolyl, 3-indolyl, 4-indolyl, 5-indolyl, 6-indolyl or 7-indolyl), isoindolyl, phanazinyl (e.g., 1-phenazinyl or 2-phenazinyl) or phenothiazinyl (e.g., 1-phenothiazinyl, 2-phenothiazinyl, 3-phenothiazinyl or 4-phenothiazinyl).

As the "heterocyclic ring", rings similar to those described above are exemplified.

When a specific group has a substituent, the substituent may be identical or different 1 to 4 substituents selected from the substituent group B listed below.

Substituent group B: hydroxy, carboxy, halogen (F, Cl, Br, I), haloalkyl (e.g., $CF_3$, $CH_2CF_3$, $CH_2CCl_3$), alkyl (e.g., methyl, ethyl, isoproopyl, tert-butyl), optionally substituted alkenyl (e.g., vinyl), optionally substituted alkynyl (e.g., ethynyl), hydroxy lower alkyl, alkoxyalkyl, optionally substituted amino lower alkyl, optionally substituted carbamoyl lower alkyl, cycloalkyl (e.g., cyclopropyl), cycloalkenyl (e.g., cyclopropenyl), optionally substituted alkoxyl (e.g., methoxy, ethoxy, propoxy, butoxy), alkenyloxy (e.g., vinyloxy, allyloxy), alkoxycarbonyl (e.g., methoxycarbonyl, ethoxycarbonyl, tert-butoxycarbonyl), hydroxy lower alkoxy, lower alkoxy lower alkoxy, nitro, nitroso, optionally substituted amino (e.g., amino, alkylamino (e.g., methylamino, ethylamino, dimethylamino), acylamino (e.g., acetylamino, benzoylamino), aralkylamino (e.g., benzylamino, tritylamino), hydroxyamino, lower alkyl carbonyl amino, lower alkenylamino), azide, aryl (e.g., phenyl), aralkyl (e.g., benzyl), cyano, isocyano, isocyanato, thiocyanato, isothiocyanato, mercapto, alkylthio (e.g., methylthio), hydroxy alkylthio, alkylsulfonyl (e.g., methanesulfonyl, ethanesulfonyl), optionally substituted carbamoyl (e.g., alkylcarbamoyl (e.g., methylcarbamoyl, ethylcarbamoyl, dimethylcarbamoyl)), sulfamoyl, acyl (e.g., formyl, lower alkylcarbonyl (e.g., acetyl)), formyloxy, haloformyl, oxalo, thioformyl, thiocarboxy, dithiocarboxy, thiocarbamoyl, sulfino, sulfo, sulfoamino, hydrazino, azide, ureido, amidino, guanidino, phthalimide, oxo, imino, —SO$_2$OH, COCONH$_2$, CSNH$_2$, thiocarbonyl optionally substituted with lower alkyl, cyano lower alkylcarbonyl, cyano lower alkenyl, lower alkenylamino carbonyl, lower alkenylamino thiocarbonyl, substituted lower alkyl (substituent: CN, =O, and/or =NH), optionally substituted heterocyclic group, optionally substituted carboxy, optionally substituted carboxyalkyl, optionally substituted salfamoyl, and optionally substituted salfamoylalkyl.

More Preferred Embodiment $R^1$ is optionally substituted aralkyl, preferably optionally substituted benzyl. Examples of such substituent include one or more substituent selected from halogen, hydroxy, cyano, nitro, amino, substituted amino (example of substituent: lower alkyl), lower alkyl, lower alkoxy and the like, preferably halogen. $R^1$ is more preferably benzyl at least optionally substituted with halogen, more preferably 4-F-benzyl.

$R^2$ and $R^3$ are each independently hydrogen, optionally substituted alkyl, optionally substituted amino, optionally substituted alkenyl, or optionally substituted alkoxy. Preferably, $R^2$ is hydrogen; and $R^3$ is optionally substituted alkyl, optionally substituted amino, optionally substituted alkenyl, or optionally substituted alkoxy. More preferably, $R^3$ is optionally substituted alkyl, optionally substituted alkenyl or optionally substituted amino.

Each substituent for "optionally substituted" in the definitions of $R^2$ and $R^3$ is a non-cyclic group. Examples of such non-cyclic group is one or more identical or different group(s) selected from the group consisting of lower alkyl, lower alkoxy, lower alkoxy lower alkyl, hydroxy lower alkoxy lower alkyl, hydroxy, hydroxy lower alkyl, amino, substituted amino (e.g., formylamino, lower alkylcarbonylamino, lower alkylamino, lower alkylaminothiocarbonylamino), lower alkylamino lower alkyl, halogen, carboxy, lower alkoxy carbonyl, CN, SO$_3$H, lower alkylthio, lower alkylthio lower alkyl, hydroxy lower alkylthio, lower alkenyloxy, lower alkoxy lower alkoxy, COCONH$_2$, CSNH$_2$, thiocarbonyl optionally substituted with lower alkyl, cyano lower alkylcarbonyl, cyano lower alkenyl, formyl, lower alkenylamino carbonyl, lower alkenylaminothiocarbonyl, lower alkenylaminothiocarbonylamino, substituted lower alkyl (example of substituent: CN, =O, =NH, OH), carbamoyl optionally substituted with optionally substituted lower alkyl, halogenated lower alkyl, halogenated lower alkoxy, NO$_2$ and the like.

More preferably, $R^2$ is hydrogen, $R^3$ is optionally substituted alkyl, optionally substituted alkenyl or optionally substituted amino. $R^3$ is preferably lower alkyl (preferably C1 to C6, more preferably C2 to C4 alkyl) optionally substituted with a substituent selected from the group consisting of lower alkoxy (e.g., OCH$_3$), CN, amino optionally substituted with mono or di lower alkyl(e.g., NHCH$_3$, N(CH$_3$)$_2$), OH, carboxy, and lower alkoxycarbonyl (e.g., COOCH$_3$). More preferably, CH$_2$CH$_2$OCH$_3$, CH$_2$CH$_2$OEt, CH$_2$CH$_2$COOCH$_3$, CH$_2$CH$_2$CH$_2$OCH$_3$, CH$_2$CH$_2$CH$_2$O(i-Pr), N(CH$_3$)$_2$, CH$_2$CH$_2$CN, CH$_2$CH$_2$N(CH$_3$)$_2$, CH$_2$CH$_2$N(i-Pr)$_2$, CH$_2$CH$_2$CH$_2$N(CH$_3$)$_2$, CH$_2$CH$_2$CH$_2$N(Et)$_2$, CH(CH$_3$) CH$_2$OH, CH(CH$_3$)COOCH$_3$ or CH$_2$CH(OH)CH$_2$CH$_3$. The "optionally substituted amino" is preferably amino substituted with one or two lower alkyl (e.g., N(CH$_3$)$_2$).

$R^4$ is hydrogen, optionally substituted carboxy, optionally substituted formylamino, optionally substituted carbamoyl, optionally substituted amino (provided that a substituent on amino in "optionally substituted formylamino", "optionally substituted carbamoyl" and "optionally substituted amino" may form an optionally-substituted N-atom containing heterocyclic ring together with an adjacent N atom), optionally substituted alkyl, optionally substituted alkenyl, optionally substituted aryl, or optionally substituted heteroaryl.

Each substituent for "optionally substituted" in $R^4$ may be any of non-cyclic group, cyclic group, optionally substituted aryloxy, optionally substituted aryloxy lower alkylcarbonyl, optionally substituted arylcarbonyl, and optionally substituted heteroarylcarbonyl. Examples of the cyclic group include optionally substituted saturated or unsaturated carbon ring or heterocyclic ring (e.g., aryl (e.g., phenyl) or heteroaryl). Examples of non-cyclic group include one or two identical or different group(s) selected from the group consisting of lower alkyl, lower alkoxy, lower alkoxy lower alkyl, hydroxy lower alkoxy lower alkyl, hydroxy, hydroxy lower alkyl, amino, substituted amino (e.g., formylamino, lower alkylcarbonylamino, lower alkylamino, lower alkylamino thiocarbonylamino), lower alkylamino lower alkyl, halogen, carboxy, lower alkoxy carbonyl, CN, SO$_3$H, lower alkylthio, lower alkylthio lower alkyl, hydroxy lower alkylthio, lower alkenyloxy, lower alkylcarbonyl, lower alkoxy carbonyl lower alkyl, hydroxy lower alkoxy, lower alkoxy lower alkoxy, COCONH$_2$, CSNH$_2$, thiocarbonyl optionally substituted with lower alkyl, cyano lower alkylcarbonyl, cyano lower alkenyl, formyl, lower alkenylaminocarbonyl, lower alkenylaminothiocarbonyl, lower alkenylaminothiocarbonylamino, substituted lower alkyl (example of substituent: CN, =O, =NH, OH), carbamoyl optionally substituted with optionally substituted lower alkyl, halogenated lower alkyl, halogenated lower alkoxy, NO$_2$ and the like.

$R^4$ is preferably optionally substituted carboxy, optionally substituted formylamino, optionally substituted carbamoyl (provided that, substituent on amino may form an optionally-substituted N-atom containing heterocyclic ring together with an adjacent N atom), optionally substituted alkyl, optionally substituted alkenyl or optionally substituted heteroaryl.

$R^4$ is more preferably optionally substituted formylamino, optionally substituted carbamoyl (provided that a substituent on amino may form an optionally-substituted N-atom containing heterocyclic ring together with an adjacent N atom), optionally substituted alkyl, or optionally substituted alkenyl.

The term "optionally substituted carboxy" in $R^4$ means —COOR (R is hydrogen or substituent), and the R is preferably lower alkyl (e.g., CH₃), hydroxy lower alkyl (e.g., CH₂CH₂OH), lower alkoxy lower alkyl (e.g., CH₂CH₂OCH₃), optionally substituted amino lower alkyl (example of substituent: lower alkanoyl (e.g., acetyl); specific example: CH₂CH₂NHCOCH₃), or optionally substituted heterocyclic group (e.g., optionally substituted piperidyl (example of substituent: lower alkylcarbonyl (e.g., acetyl), lower alkylsulfonyl (e.g., methanesulfonyl))).

The term "optionally substituted formylamino" in $R^4$ means "—NHCOH" whose one or two hydrogen is optionally substituted, and the substituent is selected from lower alkyl (e.g., CH₃), hydroxy lower alkyl (e.g., CH₂CH(OH)CH₃), lower alkoxy lower alkyl (e.g., CH₂OCH₃), optionally substituted carbamoyl lower alkyl (example of substituent: lower alkyl; specific example: CH₂CH₂CON(CH₃)₂), optionally substituted lower alkoxy (e.g., OCH₃), optionally substituted amino (e.g., N(CH₃)₂), optionally substituted heterocyclic group (e.g., furan, tetrahydrofuran), lower alkoxy carbonyl lower alkyl (e.g., CH(CH₃)COOCH₃), and optionally substituted carbamoyl (example of substituent: lower alkoxy (e.g., OCH₃), lower alkyl (e.g., CH₃), and lower alkylamino (e.g. N(CH₃)₂), lower alkoxy lower alkyl).

The substituent for "optionally substituted carbamoyl" in $R^4$ is preferably 1) lower alkyl (e.g., CH₃, CH(CH₃)₂), 2) optionally substituted lower alkyl (substituent: hydroxy, lower alkoxy (e.g., OCH₃), halogen, cyano, optionally substituted amino (e.g., NHMe), optionally substituted lower alkoxy, carbamoyl, aryloxy), 3) cycloalkyl, 4) cycloalkyl lower alkyl, 5) optionally substituted heterocyclic group (substituent: halogen, OH, lower alkyl, lower alkoxy, amino, lower alkylamino, oxo; heterocyclic, for example, thiophene, pyrazolidine, morpholino, furan, tetrahydrofuran, piperidine, thiazole, pyrrolidine), 6) optionally substituted heterocyclic group lower alkyl (substituent: halogen, OH, lower alkyl, lower alkoxy, amino, lower alkylamino, oxo; heterocyclic, for example, those as same as the above 5), 7) optionally substituted aryl (example of substituent: halogen, OH, lower alkyl, lower alkoxy, amino, lower alkylamino), 8) optionally substituted aryloxy lower alkyl (example of substituent: halogen, OH, lower alkyl, lower alkoxy, amino, lower alkylamino), 9) optionally substituted aralkyl (example of substituent: halogen, OH, lower alkyl, lower alkoxy, amino, lower alkylamino), 10) optionally substituted carbamoyl lower alkyl (e.g., CH₂CON(CH₃)₂), 11) optionally substituted lower alkoxy (e.g., OCH₃), 12) optionally substituted amino (e.g., N(CH₃)₂, NHCOCH₃, NHCH₂CH₂OH), 13) optionally substituted alkenyl, or 14) optionally substituted alkynyl (e.g., CH₂C≡CH).

Preferably, examples of the substituent for "optionally substituted amino" in $R^4$ include lower alkyl (e.g., CH₂CH₃), hydroxy lower alkyl, lower alkoxy lower alkyl (e.g., CH₂CH₂OCH₃), optionally substituted heterocyclic group, and optionally substituted carbamoyl lower alkyl.

The substituent for "optionally substituted alkyl" or "optionally substituted alkenyl" in $R^4$ is preferably hydroxy, halogen, optionally substituted heterocyclic group (e.g., morpholino), optionally substituted lower alkoxy (e.g., OCH₃), optionally substituted amino (example of substituent: lower alkyl, lower alkylcarbonyl (e.g., COCH₃)), optionally substituted carbamoyl, or optionally substituted carboxy (e.g., lower alkoxy carbonyl), and more preferably, hydroxy or lower alkoxy (e.g., OCH₃).

The substituent for "optionally substituted aryl" or "optionally substituted heteroaryl" in $R^4$ is preferably hydroxy, lower alkyl, hydroxy lower alkyl, lower alkoxy lower alkyl, optionally substituted aminoalkyl, optionally substituted carbamoyl lower alkyl, optionally substituted lower alkoxy, optionally substituted amino (e.g., NHMs), optionally substituted carbamoyl (e.g., CON(CH₃)₂), optionally substituted alkenyl, optionally substituted carboxy, optionally substituted carboxyalkyl, optionally substituted salfamoyl (e.g., SO₂NH₂), or optionally substituted salfamoylalkyl.

The substituent on amino in the above "optionally substituted formylamino", "optionally substituted amino" or "optionally substituted carbamoyl" may form an optionally-substituted N-atom containing heterocyclic ring together with an adjacent N atom. Such an N-atom containing heterocyclic ring is preferably 5 to 8-membered aromatic ring or aliphatic ring, and the ring may further intervened by N, O, S, SO₂ and the like. More preferably, morpholine and piperazine are exemplified. The heterocyclic ring may be optionally substituted with oxo, lower alkyl (e.g., methyl) and the like.

More preferably, $R^4$ is, for example, groups shown below or substituents corresponding to $R^4$ in each compound described in Example B-30.

[Formula 3]

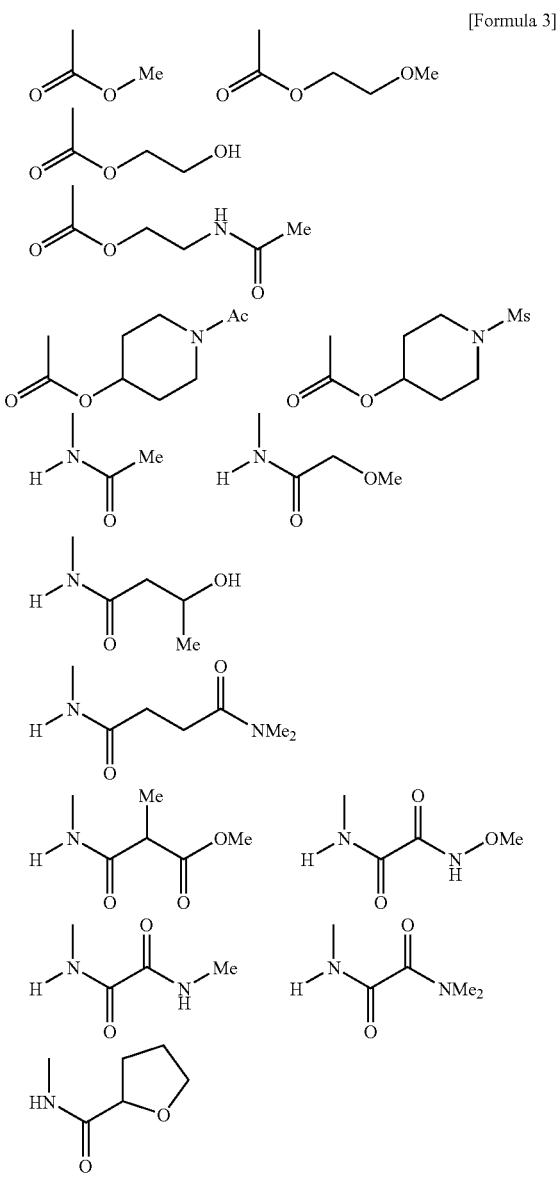

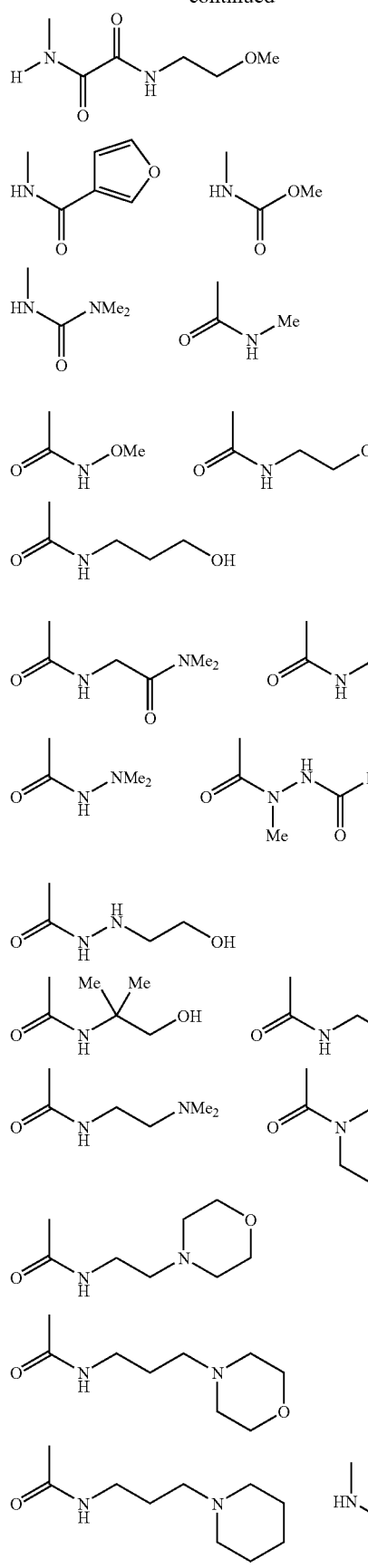
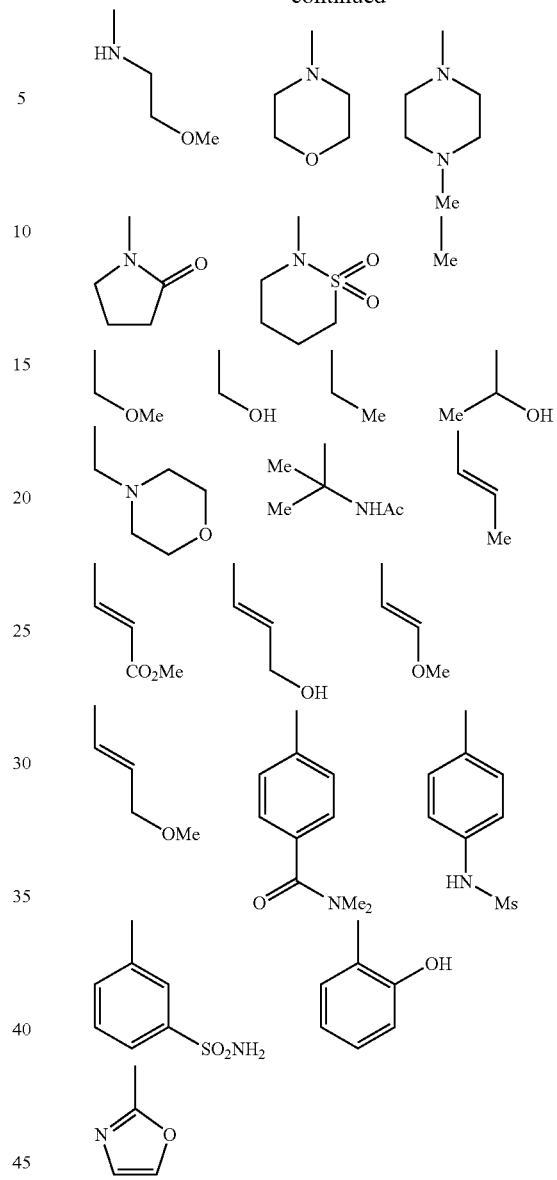

In compound (I), $R^1$ is preferably optionally substituted aralkyl, more preferably optionally substituted benzyl, particularly preferably benzyl optionally substituted with at least halogen (e.g., 4-F-benzyl); $R^2$ is hydrogen; $R^3$ is lower alkyl (preferably C1 to C6, more preferably C2 to C4 alkyl) which is optionally substituted with a substituent selected from a group consisting of optionally substituted alkyl, optionally substituted amino, optionally substituted alkenyl, or optionally substituted alkoxy, more preferably lower alkoxy (e.g., $OCH_3$), CN, amino optionally substituted with mono- or di-lower alkyl (e.g., $NHCH_3$, $N(CH_3)_2$), OH, carboxy, and lower alkoxy carbonyl(e.g., $COOCH_3$), and each substituent for "optionally substituted" in $R^3$ is preferably the aforementioned non-cyclic group, $R^3$ is more preferably $CH_2CH_2OCH_3$, $CH_2CH_2OEt$, $CH_2CH_2COOCH_3$, $CH_2CH_2CH_2OCH_3$, $CH_2CH_2CH_2O(i\text{-}Pr)$, $N(CH_3)_2$, $CH_2CH_2CN$, $CH_2CH_2N(CH_3)_2$, $CH_2CH_2N(i\text{-}Pr)_2$, $CH_2CH_2CH_2N(CH_3)_2$, $CH_2CH_2CH_2N(Et)_2$, $CH(CH_3)CH_2OH$, $CH(CH_3)COOCH_3$ or $CH_2CH(OH)CH_2CH_3$; $R^4$ is preferably optionally substituted carboxy, optionally substituted formylamino, optionally substituted carbamoyl (provided that the substituent on amino may form an optionally-substituted N-atom containing heterocyclic ring together with an adjacent N atom), optionally substituted alkyl, optionally substituted alkenyl or optionally substituted heteroaryl.

The present invention also provides a pharmaceutically acceptable salt of Compound (I) and solvates thereof. All of the theoretical possible tautomers and geometrical isomers of a compound of the present invention are also within the scope of the present invention.

Pharmaceutically acceptable salts of a compound of the present invention include, as basic salts, for example, alkali metal salts such as sodium or potassium salts; alkaline-earth metal salts such as calcium or magnesium salts; ammonium salts; aliphatic amine salts such as trimethylamine, triethylamine, dicyclohexylamine, ethanolamine, diethanolamine, triethanolamine, brocaine, meglumine, diethanolamine or ethylenediamine salts; aralkyl amine salts such as N,N-dibenzylethylenediamine or benethamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts or lysine salts. Acid salts include, for example, inorganic acid salts such as hydrochloride, sulfates salts, nitrate salts, phosphates salts, carbonates salts, hydrogencarbonates or perchlorate; organic acid salts such as acetates, propionates, lactates, maleates, fumarates, tartaric acid salts, malates, citrates salts, or ascorbates; sulfonates such as methanesulfonates, isethionates, benzenesulfonates, or p-toluenesulfonates; and acidic amino acid salts such as aspartates or glutamates.

As a solvate of compound of the present invention, alcoholate, hydrate and the like are exemplified.

Representative general production process of compounds of the present invention will be explained below. Preferably, 8-hydroxy-1,6-naphthyridine scaffold is constructed in accordance with or following the method described in Example A-1 below. Then according to methods well-known by ones skilled in the art, modification of 5-position or 7-position in side chains, or deprotection of a protecting group of hydroxyl group at 8-position may be conducted.

(1) Formation of amide group at 7-position

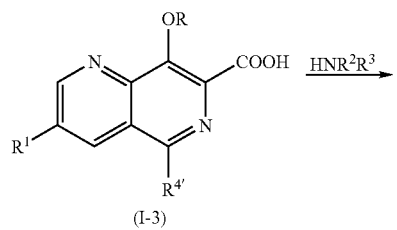

[Formula 4]

(I-3)

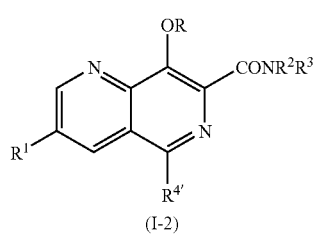

(I-2)

(R is hydrogen or hydroxy protecting group; $R^{4'}$ is $R^4$ or leaving group (e.g., halogen))

Compound (I-3) is amidated to produce Compound (I-2). This step may be preferably conducted by allowing amines ($HNR^2R^3$) to react in a solvent in the presence of a condensing agent.

As the condensing agent, dicyclohexylcarbodiimide, 1-ethyl-3-(3-dimethylaminopropyl)carbodiimide hydrochloride and the like may be used. If necessary, 1-hydroxybenzotriazole, N-hydroxysuccinimide or the like reagent may be added.

The reaction may be conducted at a temperature ranging from 0 to 100° C., preferably from 20 to 30° C.

As the reaction solvent, a wide variety of aprotic solvents may be used, and tetrahydrofuran, N,N-dimethylformamide, dichloromethane and the like are preferred.

In the above reaction, when the $R^{4'}$ moiety is a leaving group such as halogen, the leaving group may be converted to $R^4$ such as carboxy, carboxy ester, substituted amino in accordance with the method of later-described (3) after amidation of 7-position.

(2) Deprotection of protecting group of hydroxyl group at 8-position

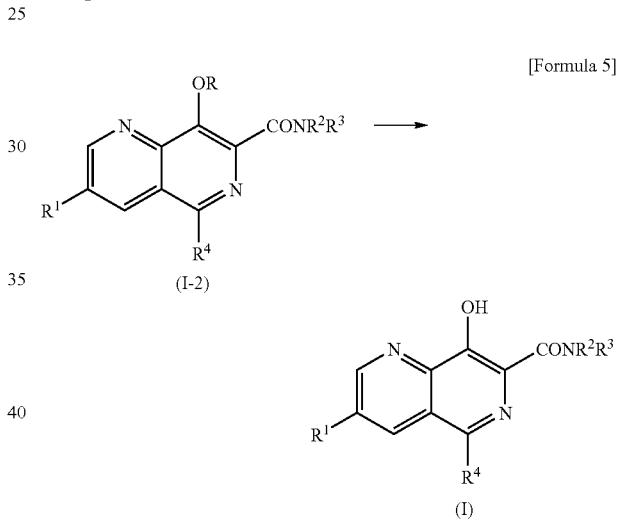

[Formula 5]

(I-2)

(I)

(R is hydroxy protecting group)

Compound (I-2) is deprotected to produce Compound (I). This step may be conducted by heating in a reaction solvent in the presence of trialkylsilyl halide and alkaline metal iodide.

As the trialkylsilyl halide, trimethylsilyl chloride and the like may be used.

As the alkaline metal iodide, for example, NaI or KI may be used.

The reaction may be conducted at a temperature ranging from room temperature to 100° C., preferably 70 to 90° C.

As the reaction solvent, a polar solvent such as acetonitrile is preferably used.

This step may be conducted using hydrogen bromide/acetic acid and under heating.

As the hydrogen bromide/acetic acid, 47% hydrogen bromide/acetic acid is preferably used.

This step may further be conducted by using $BBr_3$ at a temperature ranging form 0° C. to room temperature, or using pyridinium chloride at 150 to 220° C. Deprotection may be conducted by treating with trifluoroacetic acid.

(3) Introduction of substituted amino group in 5-position

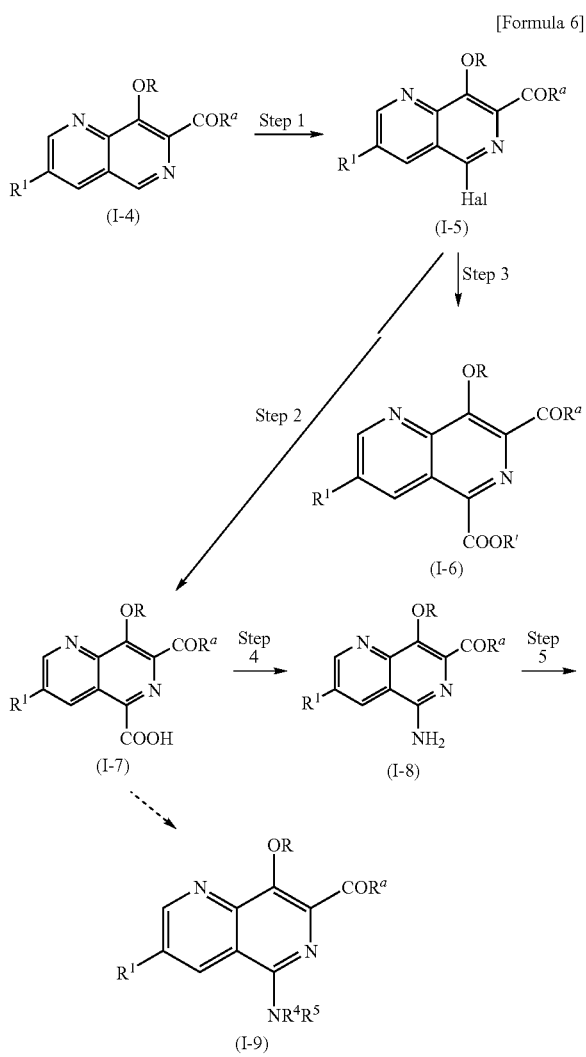

(R is hydrogen or hydroxy protecting group; $R^a$ is OH, ester residue (e.g., lower alkoxy), or $NR^2R^3$)

(Step 1)
Compound (I-4) is caused to react with halogen (e.g., bromine) preferably in acetic acid solvent in the presence of sodium acetate or the like, to give Compound (I-5). The reaction temperature is usually about 0° C. to 100° C., preferably about 20° C. to 30° C.

(Step 2)
Compound (I-5) is subjected to carbon monoxide introducing reaction to give Compound (I-7). Preferably, Compound (I-5) is caused to react with carbon monoxide in a solvent such as dimethyl sulfoxide in the presence of palladium acetate (II), 1,3-bis(diphenylphosphino)propane, triethylamine, and water. The reaction temperature is usually from room temperature to 100° C., preferably room temperature.

(Step 3)
Compound (I-5) is subjected to carbon monoxide introducing reaction similarly to Step 2, to produce Compound (I-6). In this case, alcohol having a R' moiety may coexist.

(Step 4)
Compound (I-7) is treated with diphenylphosphoryl azide and triethyl amine preferably in a solvent such as dimethylformamide, to give Compound (I-8). The reaction temperature is usually about 70° C. to 80° C.

(Step 5)
Compound (I-8) is N-alkylated, N-acylated, or N-sulfonylated, to give Compound (I-9). The reaction temperature is usually from about 0° C. to 100° C., preferably from about 0° C. to room temperature. Compound (I-9) may also be obtained by amidation of Compound (I-7).

Examples of hydroxy protecting group represented by "R" include C1 to C8 alkyls (methyl, methoxymethyl, ethyl, ethoxymethyl, iodoethyl, propyl, isopropyl, butyl, isobutyl, ethoxyethyl, methylthioethyl, methanesulfonyl ethyl, trichloroethyl, t-butyl etc.), C3 to C8 alkenyls (propenyl, allyl, isoprenyl, hexenyl, phenylpropenyl, dimethylhexenyl etc.), C7 to C19 aralkyls (benzyl, methylbenzyl, dimethylbenzyl, methoxybenzyl, ethoxybenzyl, nitrobenzyl, aminobenzyl, diphenylmethyl, phenylethyl, trityl, di-t-butylhydroxybenzyl, phthalidyl, phenacyl etc.), C6 to C12 aryls (phenyl, toluoyl, diisopropylphenyl, xylyl, trichlorophenyl, pentachlorophenyl, indanyl etc.), C1 to C12 amino groups (groups that form esters with acetone oxime, acetophenone oxime, acetoaldoxime, N-hydroxysuccinic imide, N-hydroxyphthalimide and the like), C3 to C12 hydrocarbonated silyls (trimethylsilyl, dimethylmethoxysilyl, t-butyldimethylsilyl etc.), C3 to C12 hydrocarbonated stanyls (trimethylstanyl etc.).

Compounds of the present invention obtained by the above methods may further be chemically modified by methods that are well known by ones having originally skill in the art. As a starting material for each reaction, a salt or reactive derivative may be used as desired. When a functional group exists (e.g., amino, hydroxy, carboxy) in each reaction, it may be protected in advance.

The compound of the present invention is useful as a pharmaceutical composition such as an antiviral agent. The compound of the present invention has an outstanding inhibitory activity against integrase of viruses. Therefore, the compound of the present invention is expected to prevent or treat various diseases caused by viruses producing at least integrase to grow in animal bells upon infection, and is useful as, for example, an integrase inhibitor against retroviruses (e.g., HIV-1, HIV-2, HTLV-1, SIV or FIV), especially, an anti-HIV agent.

The compound of the present invention can be used in a combination therapy with an anti-HIV agent possessing other inhibitory mechanism such as a reverse transcriptase inhibitory agent and/or a protease inhibitory agent. Since any integrase inhibitor has not been on sale yet, it is useful to use the compound of the present invention in combination therapy with a reverse transcriptase inhibitory agent and/or a protease inhibitory agent.

And the compound of the present invention can be used not only as an anti-HIV mixture but also as a concomitant agent enhancing the anti-HIV activity of the other anti-HIV agent such as in a cocktail therapy.

The compound of the present invention can be used so as in the gene therapy using a retrovirus vector derived from HIV or MLV to suppress the spread of the retrovirus vector infection over non-target tissues. Especially, in the case that cells infected with such a vector in vitro are put back in a body, a previous administration of the compound of the present invention prevents an unnecessary infection inside the body.

The compounds of the present invention can be administered orally or parenterally. For oral administration, the compounds of the present invention can be used in any form of usual formulations, for example, solid formulations such as tablets, powders, granules, capsules; aqueous formulations; oleaginous suspensions; or solutions such as syrup or elixir.

For parenteral administration, the compounds of the present invention can be used as an aqueous or oleaginous suspension injection, or nose drops. In the preparation of such formulations, conventional excipients, binding agents, lubricants, aqueous solvents, oleaginous solvents, emulsifying agents, suspending agents, preservatives or stabilizers can be optionally used. And as an anti-HIV agent, oral agents are especially preferable.

The formulation according to the present invention may be manufactured by combining (for example, admixing) a curatively effective amount of a compound of the present invention with a pharmaceutically acceptable carrier or diluent. The formulation of the present invention may be manufactured with well-known and easily available ingredients in accordance with a known method.

In the case of manufacturing a pharmaceutical composition according to the present invention, an active ingredient is admixed or diluted with a carrier, or they are contained in a carrier in the form of capsule, sacheier, paper, or another container. In the case of a carrier functioning as a diluent, the carrier is a solid, semi-solid, or liquid material, which functions as a medium. Accordingly, a formulation according to the present invention may be produced in the form of tablet, pill, powder medicine, intraoral medicine, elixir agent, suspending agent, emulsifier, dissolving agent, syrup agent, aerosol agent (solid in liquid medium), and ointment. Such a formulation may contain up to 10% of an active compound. It is preferred to formulate a compound of the present invention prior to administration.

Any suitable carrier well known to those skilled in the art may be used for the formulation. In such formulation, a carrier is in the form of solid, liquid or a mixture thereof. For instance, a compound of the present invention is dissolved into 4% dextrose/0.5% sodium citrate aqueous solution so as to be 2 mg/ml concentration for intravenous injection. Solid formulation includes powder, tablet, and capsule. Solid carrier consists of one or more of material(s) for serving also as fragrant, lubricant, dissolving agent, suspension, binder, tablet disintegrator or capsule. A tablet for oral administration contains a suitable excipient such as calcium carbonate, sodium carbonate and lactose, calcium phosphate together with a disintegrator such as corn starch and alginic acid and/or a binder such as gelatin and acacia, and a lubricant such as magnesium stearate, stearic acid and talc.

In a powder medicine, a carrier is a finely pulverized solid, which is blended with finely pulverized active ingredients. In a tablet, active ingredients are admixed with a carrier having required binding power in a suitable ratio, and it is solidified in a desired shape and size. Powder medicine and tablet contain as the active ingredient about 1 to about 99% by weight of novel compounds of the present invention. Example of suitable solid carriers include magnesium carbonate, magnesium stearate, talc, sugar, lactose, pectin, dextrin, starch, gelatin, tragacanth gum, methyl cellulose, sodium carboxymethylcellulose, low-melting wax, and cocoa butter.

A liquid formulation contains suspending agent, emulsifier, syrup agent or elixir agent. Active ingredients may be dissolved or suspended into a pharmaceutically acceptable carrier such as sterile water, a sterile organic solvent or a mixture thereof. Active ingredients may be dissolved frequently into a suitable organic solvent such as propylene glycol aqueous solution. When finely pulverized active ingredients are dispersed into aqueous starch, sodium carboxylmethylcellulose solution or suitable oil, the other compositions can be prepared.

Although an appropriate dosage of the compound of the present invention varies depending on the administration route, age, body weight, conditions of the patient, and kind of disease, in the case of oral administration, the daily dosage for an adult can be usually between approximately 0.05-3000 mg, preferably approximately 0.1-1000 mg, if necessary, in divisions. In the case of parenteral administration, the daily dosage for an adult can be between approximately 0.01-1000 mg, preferably approximately 0.05-500 mg.

EXAMPLES

Abbreviations

Me=methyl; Bn=benzyl; Bz=benzoyl; Boc=tert-butoxycarbonyl; Cbz=benzyloxycarbonyl; DMSO=dimethylsulfoxide Example A-1

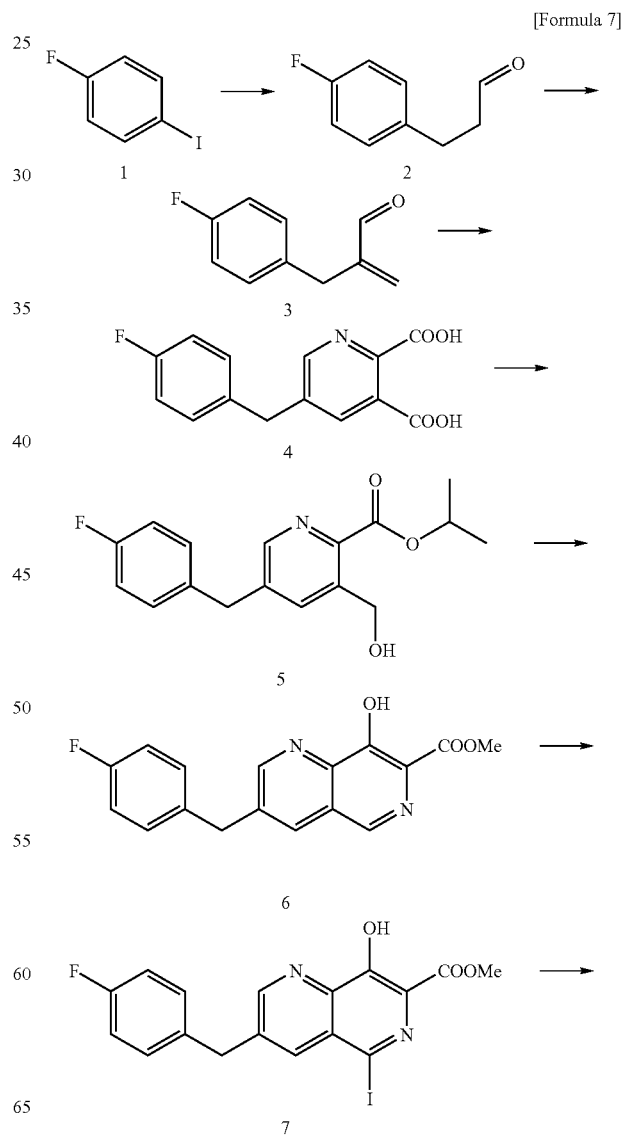

[Formula 7]

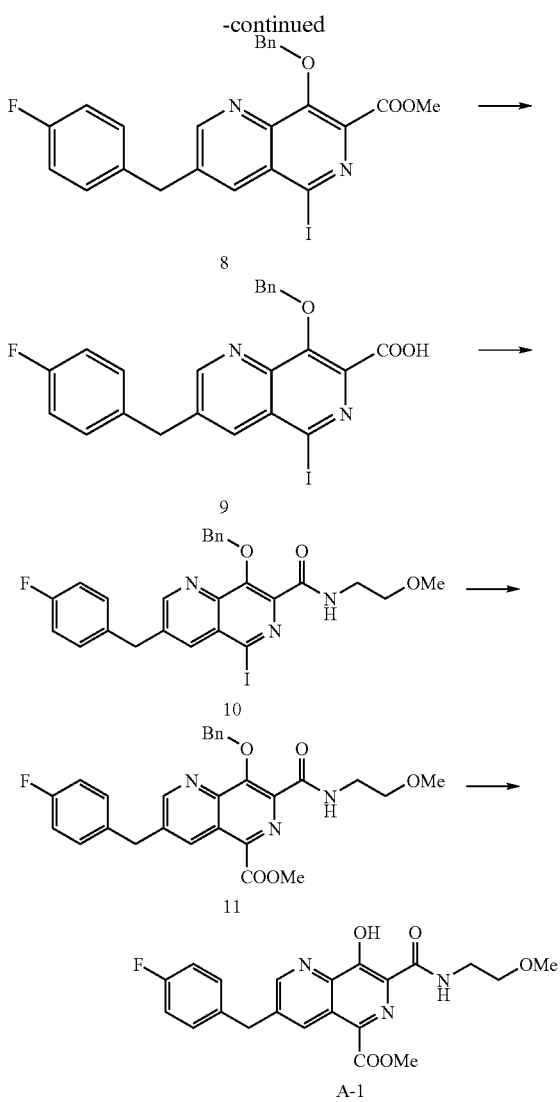

A-1. Methyl 3-(4-fluorobenzyl)-8-hydroxy-7-(2-methoxyethylcarbamoyl) [1,6]naphthyridine-5-carbonate 1) According to the method reported in Document (Chem. Commun., 1984, 1287), 4-fluoroiodobenzene (50 g, 225 mmol) and allyl alcohol (23 ml, 337 mmol) were subjected to Heck reaction in the presence of palladium acetate, which were then distilled under reduced pressure (94-96° C., 7 mmHg), to give 3-(4-fluorophenyl)propional 2 (27.5 g) in 80% yield.

NMR (CDCl$_3$) d: 2.73-2.79 (2H, m), 2.93 (2H, t, J=7.4 Hz), 6.94-7.00 (2H, m), 7.12-7.17 (2H, m), 9.81 (1H, t, J=1.2 Hz).

2) The above compound 2 (53 g, 348 mmol) was heated for 1 hour at 110° C. in 37% formalin (31.2 ml) and diethylamine hydrochloride (38.3 g), and added with ether and washed three times. After drying over anhydrous magnesium sulfate, distillation under reduced pressure (101-103° C., 8 mmHg) was conducted to give 2-(4-fluorobenzyl)-2-propenal 3 (45.3 g) in 79% yield.

NMR (CDCl$_3$) d: 3.54 (2H, s), 6.07 (1H, d, J=0.6 Hz), 6.11 (1H, t, J=1.4 Hz), 6.94-7.01 (2H, m), 7.11-7.16 (2H, m), 9.59 (1H, s).

3) According to the method reported in Document (JP-A 64-16764), after causing the above Compound 3 (253 g, 1.54 mol) and 2-aminobutane dicarboxylic acid diethylester (240 g, 1.28 mol) which is known in Document (Chem. Pharm. Bull., 1989, 37, 3236.) to react, sodium hydroxide (154 g, 3.85 mol) aqueous solution (600 ml) was added for alkaline hydrolysis, to give 2-(4-fluorobenzyl)pyridine-2,3-dicarboxylic acid 4 (150 g) in 43% yield.

NMR (DMSO-d$_6$) d: 4.09 (2H, s), 7.11-7.18 (2H, m), 7.32-7.38 (2H, m), 8.05 (1H, d, J=2.0 Hz), 8.68 (1H, d, J=2.0 Hz), 13.50 (2H, br s).

4) After heating the above Compound 4 (120 g, 466 mmol) for 2 hours at 120° C. in acetic anhydride, the solvent was distilled off, and the resultant acid anhydride was subjected to isopropyl-added alcoholysis, followed by reduction of the acid chloride according to the method reported in Document (J. Med. Chem., 1989, 32, 827.), to give 5-(4-fluorobenzyl)-3-hydroxymethylpyridine-2-carboxylic acid isopropyl ester 5 (32.1 g) in 35% yield.

NMR (CDCl$_3$) d: 1.45 (6H, d, J=6.2 Hz), 3.63 (1H, br s), 4.01 (2H, s), 4.76 (2H, s), 5.34 (1H, sep, J=6.2 Hz), 6.69-7.03 (2H, m), 7.00-7.15 (2H, m), 7.61 (1H, d, J=2.1 Hz), 8.54 (1H, d, J=2.1 Hz).

5) After subjecting the above Compound 5 (59.0 g, 195 mmol) to Mitsunobu reaction with N-tosylglycine methyl ester according to the method described in Document (WO02/30930), ring-closure was caused with 1M sodium methoxide, to give 3-(4-fluorobenzyl)-8-hydroxy-1,6-naphthyridine-7-carboxylic acid methyl ester 6 (50.3 g) in 83% yield.

NMR (CDCl$_3$) d: 4.13 (3H, s), 4.23 (2H, s), 7.02-7.08 (2H, m), 7.17-7.23 (2H, m), 7.97 (1H, m), 8.77 (1H, s), 9.08 (1H, d, J=2.1 Hz), 11.77 (1H, s).

6) To a dimethylformamide solution (200 ml) of the above Compound 6 (3.56 g, 11.4 mmol) was added N-iodo succinimide (3.06 g, 13.6 mmol), and the solution was stirred overnight at room temperature. The reaction solution was distilled off under reduced pressure, and the residue was added with chloroform, washed with 10% sodium hydrogen sulfite aqueous solution and water, and dried over anhydrous sodium sulfate, and then the solvent was distilled off. Precipitated crystals were collected by filtering, and washed with methanol to give 3-(4-fluorobenzyl)-8-hydroxy-5-iodo[1,6]naphthyridine-7-carboxylic acid methyl ester 7 (4.97 g) in 99% yield.

NMR (CDCl$_3$) d: 4.10 (3H, s), 4.27 (2H, s), 7.03-7.09 (2H, m), 7.18-7.23 (2H, m), 8.10 (1H, m), 8.99 (1H, d, J=1.8 Hz), 11.76 (1H, s).

7) To a dimethylformamide suspension (80 ml) of the above Compound 7 (8.76 g, 20 mmol) were added DBU (4.48 ml, 30 mmol) and benzylbromide (3.56 ml, 30 mmol), and the solution was stirred for 5 hours at room temperature. The reaction solution was added with 0.5M citric acid aqueous solution and 10% sodium hydrogen sulfite aqueous solution, and extracted twice with ethyl acetate. The organic phase was washed with water, saturated sodium hydrogen carbonate and saturated brine. After drying over anhydrous magnesium sulfate, the residue obtained by distilling off the solvent was subjected to silica gel chromatography. The precipitated crystals were collected by filtering, and washed with diisopropyl ether, to give 8-benzyloxy-3-(4-fluorobenzyl)-5-iodo[1,6] naphthyridine-7-carboxylic acid methyl ester 8 (7.64 g) in 72% yield.

NMR (CDCl$_3$) d: 3.94 (3H, s), 4.26 (2H, s), 5.54 (2H, s), 7.03-7.09 (2H, m), 7.19-7.26 (2H, m), 7.32-7.41 (3H, m), 7.55-7.57 (2H, m), 8.13 (1H, m), 8.97 (1H, d, J=2.1 Hz).

8) To the above Compound 8 (20.0 g, 37.86 mmol) was added tetrahydrofuran (100 ml) and methanol (100 ml) to give suspension, followed by addition of 2N sodium hydroxide aqueous solution (24.6 ml, 49.2 mmol) under stirring at room temperature and stirring was continued. After 4 hours, 2N hydrochloric acid (24.6 ml, 49.2 mmol) was added, and the reaction solution was concentrated under reduced pressure and added with chloroform (150 ml) and water (150 ml). Then the solution was shaken for separation, washed with saturated sodium hydrogen carbonate and dried over sodium sulfate, followed by distillation under reduced pressure. The residue (20.8 g) was added with diisopropyl ether (80 ml) and n-hexane (80 ml), warmed on a water bath for crystallization, and then the crystals were collected by filtering and washed with diisopropyl ether:n-hexane (1:1), to give 8-benzyloxy-3-(4-fluorobenzyl)-5-iodo[1,6]naphthyridine-7-carboxylic acid 9 in a yield of (19.41 g, 99.7%).

Melting point: 132-134° C.

NMR (CDCl$_3$) d: 4.28 (2H, s), 5.69 (2H, s), 7.05-7.11 (2H, m), 7.20-7.26 (2H, m), 7.31-7.39 (3H, m), 7.59-7.62 (2H, m), 8.13-8.14 (1H, m), 9.03 (1H, d, J=2.1 Hz), 10.80 (1H, brs).

9) To the above Compound 9 (7.0 g, 13.6 mmol), 1-hydroxybenzotriazole (208 mg, 1.36 mmol) was added dichloromethane (75 ml) to give suspension, and was added 2-methoxyethyl amine (1.42 ml, 16.3 mmol) in nitrogen gas flow under stirring on ice, followed by 1-ethyl-3-(3-dimethylaminopropyl)carbodiimide hydrochloride (3.13 g, 16.3 mmol). 30 minutes later, the solution was stirred at room temperature. After 3 hours, the reaction solution was subjected to distillation under reduced pressure, and to the residue (12 g) was added and solved ethyl acetate (150 ml) and water (100 ml), and followed by 2N hydrochloric acid aqueous solution (5.7 ml, 11.4 mmol). Then the solution was shaken for separation, washed once with water and with sodium chloride aqueous solution, dried over sodium sulfate and subjected to distillation under reduced pressure. The resultant residue (7.97 g) was solved in methanol (5 ml), and added with diisopropyl ether (35 ml) little by little under warming and left at room temperature. Then the product was collected by filtering and washed with diisopropyl ether, to give Compound 10 (6.31 g, 81.1%). The filtrate was subjected to silica gel silica gel chromatography, to give 8-benzyloxy-3-(4-fluorobenzyl)-5-iodo[1,6]naphthyridine-7-carboxylic acid (2-methoxyethyl) amide 10 (437 mg, 5.6%).

NMR (CDCl$_3$) d: 3.38 (3H, s), 3.56-3.59 (2H, m), 3.64-3.70 (2H, m), 4.25 (2H, s), 5.52 (2H, s), 7.03-7.10 (2H, m), 7.19-7.24 (2H, m), 7.31-7.39 (3H, m), 7.64-7.66 (2H, m), 7.98 (1H, m), 8.09-8.10 (1H, m), 8.97 (1H, d, J=2.1 Hz).

10) The above Compound 10 (400 mg, 0.7 mmol) and palladium acetate (8 mg, 0.035 mmol) were solved in dimethylformamide (11 ml), added with methanol (0.29 ml, 7.16 mmol) followed by triethylamine (0.30 ml, 2.15 mmol), and deaeration of the reaction vessel with carbon monoxide was repeated three times. Then the solution was stirred at room temperature in the presence of carbon monoxide. After 6 hours, the reaction mixture was added with ethyl acetate (40 ml), water (30 ml), an 10% citric acid (4 ml), and shaken for separation. Then the aqueous phase was extracted once with ethyl acetate, and the ethyl acetate phase was washed twice with water, dried over sodium sulfate and subjected to distillation under reduced pressure. The obtained residue (0.38 g) was subjected to silica gel chromatography, to give crystalline 8-benzyloxy-3-(4-fluorobenzyl)-7-(2-methoxyethylcarbamoyl)[1,6]naphthyridine-5-carboxylic acid methyl ester 11 (296 mg, 84.1%).

Melting point: 94° C.

NMR (CDCl$_3$) d: 3.373H, s), 3.56-3.59 (2H, m), 3.65-3.71 (2H, m), 4.04 (3H, s), 4.22 (2H, s), 5.67 (2H, s), 7.01-7.07 (2H, m), 7.19-7.24 (2H, m), 7.30-7.39 (3H, m), 7.61-7.64 (2H, m), 8.08 (1H, m), 9.03 (1H, d, J=2.1 Hz), 9.10 (1H, m).

11) To the above Compound 11 (293 mg, 0.583 mmol) was added and solved trifluoroacetic acid (2.9 ml), and the solution was left at room temperature. After 1.5 hours, the reaction solution was distilled under reduced pressure, and the residue was added with toluene and distilled again. To the resultant residue was added and solved chloroform, and the solution was injected into ice water, and a saturated sodium hydrogen carbonate aqueous solution (2 ml) was added and shaken, and then pH was adjusted to 8.60. Thereafter, the solution was added with 10% citric acid aqueous solution (2.5 ml), shaken, and separated after adjusting pH to 5.36, and then washed once with water. After drying over sodium sulfate, the residue obtained by distillation under reduced pressure was recrystallized from acetone-diethyl ether, to give Compound A-1 (174 mg, 72.5%).

Melting point: 168-169° C.

Elemental analysis for $C_{21}H_{20}FN_3O_5$
Calcd.(%): C, 61.01; H, 4.88; F, 4.60; N, 10.16.
Found.(%): C, 61.15; H, 4.76; F, 4.44; N, 10.26.

NMR (CDCl$_3$) d: 3.44 (3H, s), 3.62-3.66 (2H, m), 3.70-3.76 (2H, m), 4.02 (3H, s), 4.22 (2H, s), 7.00-7.06 (2H, m), 7.17-7.22 (2H, m), 8.34 (1H, m), 9.02 (1H, d, J=2.1 Hz), 9.11 (1H, d, J=2.1 Hz), 13.88 (1H, brs).

Example A-2

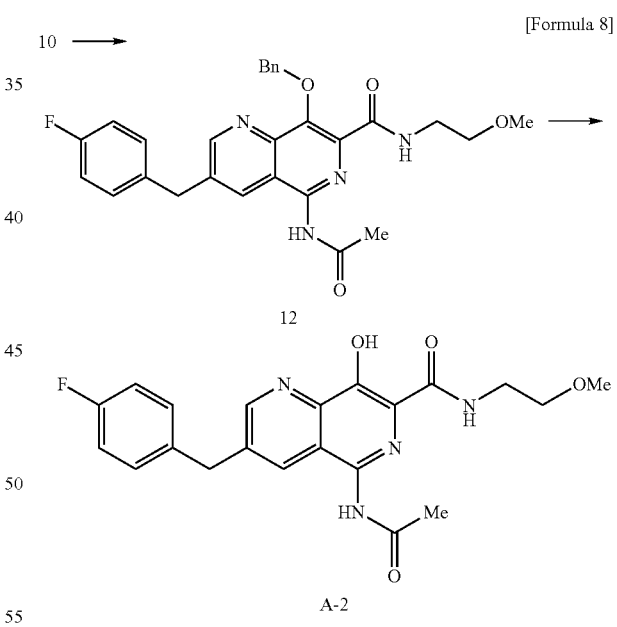

A-2

5-acetylamino-3-(4-fluorobenzyl)-8-hydroxy[1,6] naphthyridine-7-carboxylic acid 2-methoxyethyl amide 1) To Compound 10 (571 mg, 1 mmol) and acetic acid amide (89 mg, 1.5 mmol) was added and solved dioxane (12 ml), and were added cesium carbonate (48.8 mg, 1.5 mmol) and 4,5-bis(diphenylphosphino)-9,9-dimethylxancene (88 mg, 0.152 mmol), and palladium acetate (24 mg, 0.107 mmol) under stirring at room temperature in nitrogen gas flow, and then the solution was stirred for 5 hours under heating in an oil bath at 70° C. The mixture was added with ethyl acetate, water and ammonium chloride aqueous solution for extraction, washed with sodium chloride aqueous solution, dried over sodium sulfate and the subjected to distillation. The obtained residue was subjected to silica gel chromatography and recrystallized from acetone-diisopropyl ether, to give 5-acetylamino-8-benzyloxy-3-(4-fluorobenzyl)[1,6]naphthyridine-7-carboxylic acid (2-methoxyethyl)amide 12 (245 mg, 80.9%) as colorless crystals.

Melting point: 147-149° C.

NMR (CDCl$_3$) d: 2.31 (3H, brs), 3.28 (3H, s), 3.46 (2H, t, J=5.1 Hz), 3.58 (2H, t, J=5.1 Hz), 4.21 (2H, s), 5.53 (2H, s), 7.00-7.06 (2H, m), 7.19-7.23 (2H, m), 7.36-7.39 (3H, m), 7.57-7.59 (2H, m), 8.12 (1H, brs), 8.20 (1H, m), 8.46 (1H, brs), 9.00 (1H, d, J=1.8 Hz).

2) According to the method of 11) in Example A-1, A-2 (271 mg) was obtained from the above Compound 10 (390 mg, 0.776 mmol) in 85% yield.

Melting point: 216-217° C.

Elemental analysis for C$_{21}$H$_{20}$FN$_4$O$_4$

Calcd.(%): C, 61.16; H, 5.13; F, 4.61; N, 13.59.

Found.(%): C, 61.06; H, 5.17; F, 4.38; N, 13.43.

NMR (CDCl$_3$) d: 2.30 (3H, brs), 3.43 (3H, s), 3.59-3.63 (2H, m), 3.66-3.72 (2H, m), 4.20 (2H, s), 6.99-7.05 (2H, m), 7.15-7.20 (2H, m), 7.67 (1H, brs), 7.97 (1H, brs), 8.06 (1H, m), 9.00 (1H, d, J=2.1 Hz), 13.21 (1H, brs).

Example A-3

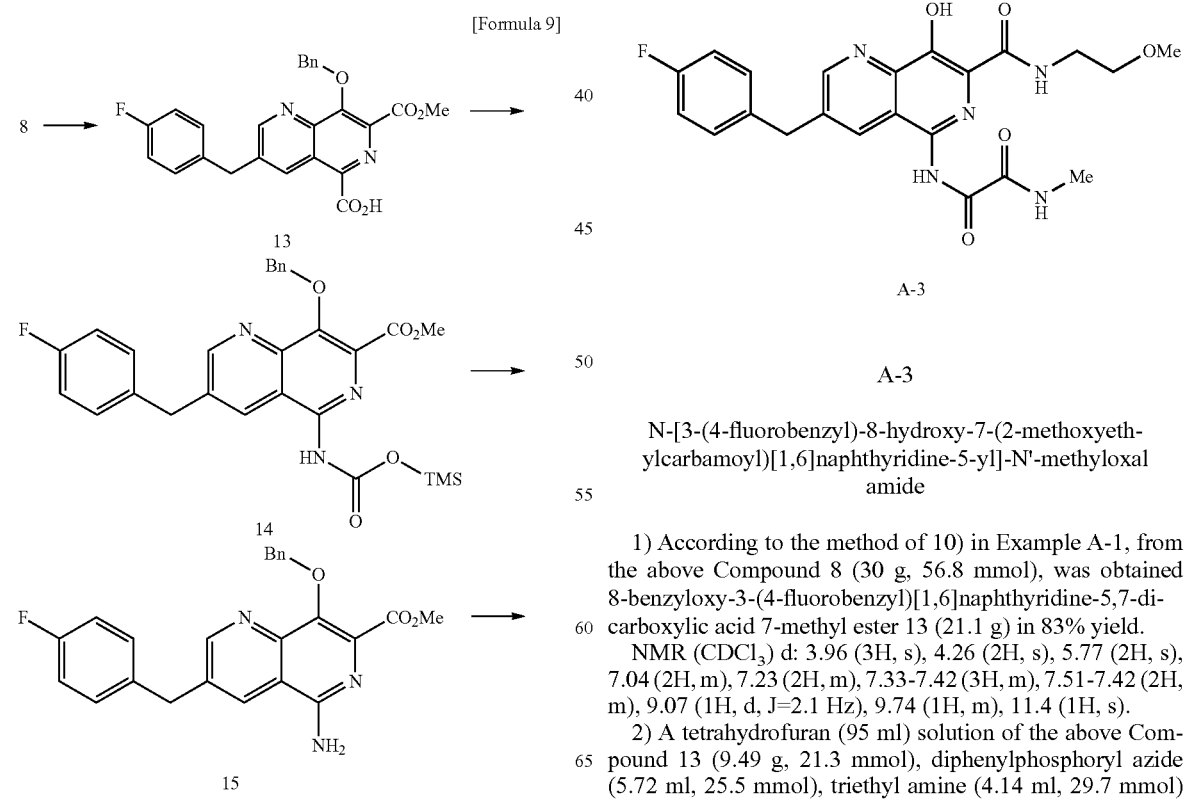

A-3

N-[3-(4-fluorobenzyl)-8-hydroxy-7-(2-methoxyethylcarbamoyl)[1,6]naphthyridine-5-yl]-N'-methyloxalamide 1) According to the method of 10) in Example A-1, from the above Compound 8 (30 g, 56.8 mmol), was obtained 8-benzyloxy-3-(4-fluorobenzyl)[1,6]naphthyridine-5,7-dicarboxylic acid 7-methyl ester 13 (21.1 g) in 83% yield.

NMR (CDCl$_3$) d: 3.96 (3H, s), 4.26 (2H, s), 5.77 (2H, s), 7.04 (2H, m), 7.23 (2H, m), 7.33-7.42 (3H, m), 7.51-7.42 (2H, m), 9.07 (1H, d, J=2.1 Hz), 9.74 (1H, m), 11.4 (1H, s).

2) A tetrahydrofuran (95 ml) solution of the above Compound 13 (9.49 g, 21.3 mmol), diphenylphosphoryl azide (5.72 ml, 25.5 mmol), triethyl amine (4.14 ml, 29.7 mmol) and 2-(trimethylsilyl)ethanol (4.26 ml, 29.7 mmol) was refluxed under heating for 3 hours in a nitrogen gas flow. After restoring to room temperature, the reaction solution was added with 10% citric acid aqueous solution and ethyl acetate, and extracted three times with ethyl acetate. The extract was washed with 10% citric acid aqueous solution, saturated sodium hydrogen carbonate aqueous solution and water. After drying over anhydrous sodium sulfate, and concentrating under reduced pressure, a crude product of Compound 14 was obtained as oily substance (14.31 g). This was used for the subsequent reaction without further purification.

3) To a tetrahydrofuran (95 ml) solution of the above crude product of Compound 14 (14.31 g) were added 1M tetrabutyl ammonium fluoride-tetrahydrofuran solution (32 ml) and potassium fluoride (1.86 g), and the mixture was stirred overnight at room temperature. The reaction solution was added with 10% citric acid aqueous solution and ethyl acetate, and extracted three times with ethyl acetate. The extract was washed with 10% citric acid aqueous solution, saturated sodium hydrogen carbonate aqueous solution, water and saturated brine, and then dried over anhydrous sodium sulfate. The residue concentrated under reduced pressure was purified on silica gel chromatography, and then recrystallized with ethyl acetate-diisopropyl ether, to give 5-amino-8-benzyloxy-3-(4-fluorobenzyl)[1,6]naphthyridine-7-carboxylic acid methyl ester 15 (7.48 g) in 84% yield. Further, 431 mg of second crystals were obtained.

Melting point: 159-160° C.

NMR (CDCl$_3$) d: 3.91 (3H, s), 4.19 (2H, s), 5.28 (2H, br. s), 5.35 (2H, s), 7.03 (2H, t like, J=8.7 Hz), 7.16-7.24 (2H, m), 7.30-7.40 (3H, m), 7.56-7.63 (2H, m), 7.86 (1H, br.s), 9.01 (1H, d, J=2.1 Hz).

4) A tetrahydrofuran (20 ml) solution of the above Compound 15 (1.0 g, 2.40 mmol) and pyridine (0.49 ml, 6.00 mmol) was cooled to −10° C., added with oxalyl chloride (0.42 ml, 4.80 mmol) and stirred for 20 minutes. At the same temperature, 40% methylamine aqueous solution (1.9 ml) was added and stirred for another 10 minutes. The reaction solution was added with water and 2M hydrochloric acid and extracted with ethyl acetate. The extract was washed with water and saturated brine, and dried over anhydrous magnesium sulfate. The solvent was distilled off under reduced pressure, and the residue was purified on silica gel chromatography. The obtained solid was washed with methanol, to give 8-benzyloxy-3-(4-fluorobenzyl)-5-(methylaminooxalylamino)[1,6]naphthyridine-7-carboxylic acid methyl ester 16 (908 mg) in 75% yield.

NMR (CDCl$_3$) d: 3.01 (3H, d, J=5.4 Hz), 3.9.4 (3H, s), 4.20 (2H, s), 5.54 (2H, s), 7.00-7.06 (2H, m), 7.16-7.22 (2H, m), 7.30-7.45 (3H, m), 7.56-7.61 (2H, m), 7.98 (1H, s), 9.03 (1H, d, J=2.1 Hz), 9.81 (1H, br s).

5) The above Compound 16 (388 mg, 0.772 mmol) was dissolved in dimethylformamide (5 ml), added with 5M sodium hydroxide aqueous solution (0.46 ml, 2.30 mmol), and stirred for 4 hours at room temperature. To the reaction solution was added 5M hydrochloric acid (0.46 ml, 2.30 mmol) for neutralizing the solution, and then was added 2 M hydrochloric acid (0.5 ml) for acidifying the solution. Then water was added followed by extraction with chloroform. The extract was washed with water and dried over anhydrous magnesium sulfate. The solvent was distilled off under reduced pressure, and the resultant residue was recrystallized with tetrahydrofuran-methanol, to give 8-benzyloxy-3-(4-fluorobenzyl)-5-(methylaminooxalylamino)[1,6]naphthyridine-7-carboxylic acid 17 (271 mg) in 72% yield.

NMR (DMSO-d$_6$) d: 2.78 (3H, d, J=4.9 Hz), 4.26 (2H, s), 5.47 (2H, s), 7.11-7.19 (2H, m), 7.35-7.44 (5H, m), 7.56-7.61 (2H, m), 8.30 (1H, s), 8.92 (1H, d, J=4.9 Hz), 9.18 (1H, d, J=2.1 Hz), 11.18 (1H, s), 13.44 (1H, s).

6) According to the method of 9) in Example A-1, from the above Compound 17 (183 mg, 0.375 mmol), N-[8-benzyloxy-3-(4-fluorobenzyl)-7-(2-methoxyethylcarbamoyl)[1,6]naphthyridine-5-yl]-N'-methyl oxalamide 18 (107 mg) was obtained in 52% yield.

NMR (CDCl$_3$) d: 3.02 (3H, d, J=5.1 Hz), 3.34 (3H, s), 3.49-3.55 (2H, m), 3.61-3.66 (2H, m), 4.20 (1H, s), 5.54 (1H, s), 7.00-7.07 (2H, m), 7.16-7.23 (3H, m), 7.43-7.48 (1H, m), 7.61-7.66 (2H, m), 8.06 (1H, s), 8.10-8.14 (1H, m), 9.03 (1H, d, J=2.1 Hz).

7) According to the method of 11) in Example A-1, A-3 (64 mg) was obtained in 77% yield from the above Compound 18 (100 mg, 0.183 mmol).

NMR (DMSO-d$_6$) d: 2.77 (3H, d, J=4.8 Hz), 3.28 (3H, s), 3.52 (4H, s), 4.25 (2H, s), 7.10-7.18 (2H, m), 7.32-7.39 (2H, m), 8.23 (1H, s), 8.84-8.95 (2H, m), 9.09 (1H, s), 11.00 (1H, s), 13.71 (1H, s).

Example A-4

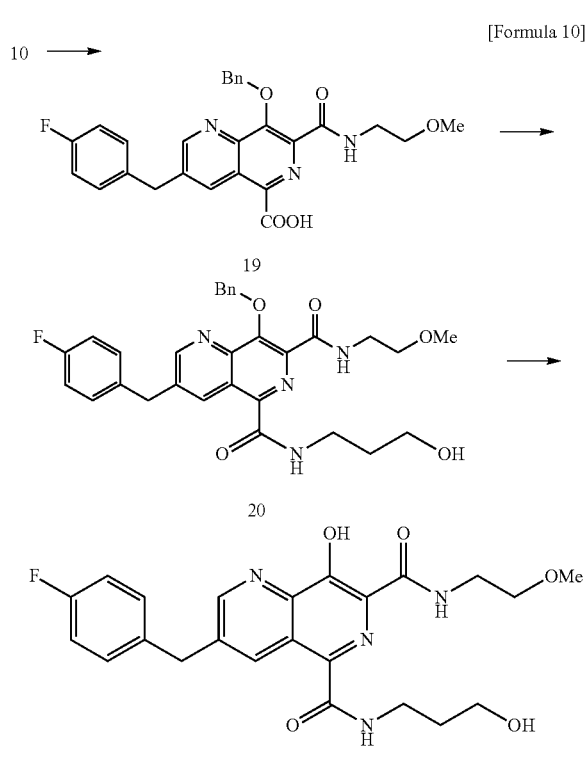

A-4

3-(4-fluorobenzyl)-8-hydroxy[1,6]naphthyridine-5,7-carboxylic acid 5-[(3-hydroxypropyl)amide]

7-[(2-methoxyethyl)amide]

1) According to the method 10) in Example A-1, from the above Compound 10 (3.00 g, 5.25 mmol), 8-benzyloxy-3-(4-fluorobenzyl)-7-(2-methoxyethylcarbamoyl)[1,6]naphthyridine-5-carboxylic acid 19 (1.56 g) was obtained in 61% yield.

NMR (CDCl$_3$) d: 3.29 (3H, s), 13.42-3.50 (2H, m), 3.57-3.64 (2H, m), 4.25 (2H, s), 5.79 (2H, s), 7.00-7.08 (2H, m), 7.20-7.26 (2H, m), 7.34-7.43 (3H, m), 7.48-7.53 (2H, m), 8.09-8.13 (1H, m), 9.05 (1H, d, J=2.1 Hz), 9.74 (1H, d, J=2.1 Hz).

2) According to the method of 9) in Example A-1, from the above Compound 19 (200 mg, 0.409 mmol), 8-benzyloxy-3-(4-fluorobenzyl)-7-(2-methoxyethylcarbamoyl)[1,6]naphthyridine-5-carboxylic acid 3-hydroxypropyl ester 20 (176 mg) was obtained in 77% yield.

NMR (CDCl$_3$) d: 1.87-1.95 (2H, m), 3.40 (3H, s), 3.57-3.61 (2H, m), 3.64-3.73 (4H, m), 3.94 (2H, t, J=5.3 Hz), 4.21 (2H, s), 5.63 (2H, s), 6.97-7.06 (2H, m), 7.15-7.26 (2H, m), 7.27-7.39 (3H, m), 7.61-7.66 (2H, m), 8.33 (1H, t, J=5.4 Hz), 9.02 (1H, d, J=2.2 Hz), 9.36-9.40 (1H, m), 9.94 (1H, s).

3) According to the method 11) in Example A-1, A-4 (82 mg) was obtained in 58% yield from the above Compound 20 (170 mg, 0.311 mmol).

NMR (CDCl$_3$) d: 1.89-1.98 (2H, m), 3.49 (3H, s), 3.62-3.71 (4H, m), 3.72-3.79 (2H, m), 4.05 (2H, t, J=5.0 Hz), 4.20 (2H, s), 6.95-7.04 (2H, m), 7.15-7.23 (2H, m), 8.48-8.54 (1H, m), 8.99 (1H, d, J=2.2 Hz), 9.50 (1H, br s), 9.90 (1H, d, J=2.2 Hz), 13.40 (1H, s).

Example A-5 to A-8

According to the method of Example A-1, Compounds A-5 to A-8 were synthesized.

[Formula 11]

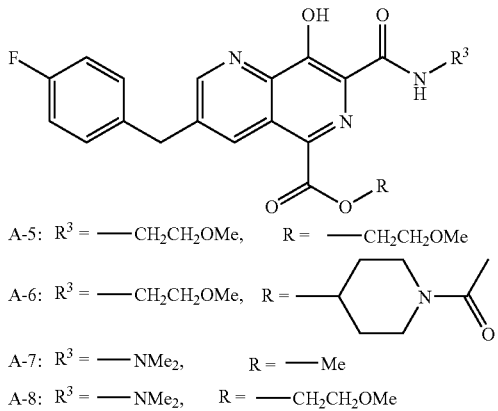

A-5: R$^3$ = —CH$_2$CH$_2$OMe,  R = —CH$_2$CH$_2$OMe

A-6: R$^3$ = —CH$_2$CH$_2$OMe,  R = 1-acetylpiperidin-4-yl

A-7: R$^3$ = —NMe$_2$,  R = —Me

A-8: R$^3$ = —NMe$_2$,  R = —CH$_2$CH$_2$OMe

Example A-5

3-(4-fluorobenzyl)-8-hydroxy-7-(2-methoxyethylcarbamoyl)[1,6]naphthyridine-5-carboxylic acid 2-methoxyethyl ester Melting point: 139-141° C.
Elemental analysis for C$_{23}$H$_{24}$FN$_3$O$_6$
Calcd.(%): C, 60.39; H, 5.29; F, 4.15; N, 9.19.
Found.(%): C, 60.20; H, 5.21; F, 4.06; N, 9.29.
NMR (CDCl$_3$) d: 3.44 (3H, s), 3.46 (3H, s), 3.61-3.65 (2H, m), 3.70-3.75 (2H, m), 3.78-3.81 (2H, m), 4.21 (2H, s), 4.57-4.60 (2H, m), 6.70-7.06 (2H, m), 7.17-7.22 (2H, m), 8.36-8.40 (1H, m), 9.02 (1H, d, J=2.4 Hz), 9.08 (1H, d, J=2.4 Hz), 13.88 (1H, brs).

Example A-6

3-(4-fluorobenzyl)-8-hydroxy-7-(2-methoxyethylcarbamoyl)[1,6]naphthyridine-5-carboxylic acid 1-acetylpiperidine-4-yl ester Melting point: 92-94° C.
Elemental analysis for C$_{27}$H$_{29}$FN$_4$O$_6$.0.7H$_2$O
Calcd.(%): C, 60.39; H, 5.29; F, 4.15; N, 9.19.
Found.(%): C, 60.20; H, 5.21; F, 4.06; N, 9.29.
NMR (CDCl$_3$) d: 1.80-1.95 (2H, m), 1.95-2.10 (2H, m), 2.15 (3H, s), 3.41 (3H, s), 3.47-3.54 (1H, m), 3.63-3.75 (6H, m), 3.85-3.91 (1H, m), 4.23 (2H, s), 5.32-5.39 (1H, m), 7.01-7.07 (2H, m), 7.18-7.23 (2H, m), 8.34-8.38 (1H, m), 9.04 (1H, d, J=2.1 Hz), 9.07 (1H, d, J=2.1 Hz), 13.84 (1H, brs).

Example A-7

7-(N',N'-dimethylhydrazinocarbonyl)-3-(4-fluorobenzyl)-8-hydroxy[1,6]naphthyridine-5-carboxylic acid methyl ester Melting point: 169-170° C.
Elemental analysis for C$_{20}$H$_{19}$FN$_4$O$_4$
Calcd.(%): C, 60.39; H, 5.29; F, 4.15; N, 9.19.
Found.(%): C, 60.20; H, 5.21; F, 4.06; N, 9.29.
NMR (CDCl$_3$) d: 2.82 (6H, s), 4.03 (3H, s), 4.22 (2H, s), 7.00-7.06 (2H, m), 7.17-7.22 (2H, m), 8.77 (1H, brs), 9.03 (1H, d, J=2.1 Hz), 9.07 (1H, d, J=2.1 Hz), 13.60 (1H, brs)

Example A-8

7-(N',N'-dimethylhydrazinocarbonyl)-3-(4-fluorobenzyl)-8-hydroxy[1,6]naphthyridine-5-carboxylic acid 2-methoxyethyl ester Melting point: 138 (wet)-210° C.
Elemental analysis for C$_{22}$H$_{23}$FN$_4$O$_5$
Calcd.(%): C, 60.39; H, 5.29; F, 4.15; N, 9.19.
Found.(%): C, 60.20; H, 5.21; F, 4.06; N, 9.29.
NMR (CDCl$_3$) d: 2.79 (6H, s), 3.47 (3H, s), 3.78-3.81 (2H, m), 4.21 (2H, s), 4.58-4.61 (2H, m), 7.00-7.06 (2H, m), 7.17-7.22 (2H, m), 8.76 (1H, brs), 9.02 (1H, d, J=2.1 Hz), 9.05 (1H, m), 13.68 (1H, brs).

Example A-9 to A-10

According to the method of Example A-3, Compounds A-9 to A-10 were synthesized.

[Formula 12]

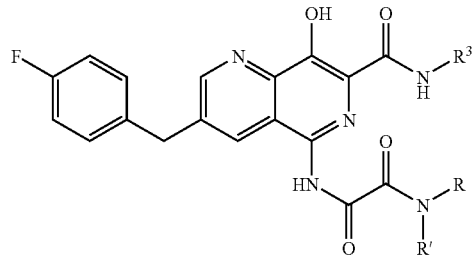

-continued

A-9: R³ = —CH₂CH₂OMe, R = —OMe, R' = —H
A-10: R³ = —NMe₂, R = —OMe, R' = —H
A-11: R³ = —NMe₂, R = —Me, R' = —H
A-12: R³ = —NMe₂, R = —NMe₂, R' = —H
A-13: R³ = —CH₂CH₂OMe, R = —CH₂CH₂OMe, R' = —H
A-14: R³ = —CH₂CH₂OMe, R = —NMe₂, R' = —H
A-15: R³ = —CH₂CH₂OMe, R = —Me, R' = —Me

A-9. N-[3-(4-fluorobenzyl)-8-hydroxy-7-(2-methoxyethylcarbamoyl)[1,6]naphthyridine-5-yl]-N'-methoxy oxalamide NMR (DMSO-d₆) d: 3.28 (3H, s), 3.52 (4H, s), 3.71 (3H, s), 4.26 (2H, s), 7.10-7.18 (2H, m), 7.33-7.38 (2H, m), 8.26 (1H, s), 8.86 (1H, br s), 9.10 (1H, d, J=1.8 Hz), 11.11 (1H, s), 12.34 (1H, s), 13.71 (1H, br s).

A-10

N-[7-(N',N'-dimethylhydrazinocarbonyl)-3-(4-fluorobenzyl)-8-hydroxy[1,6]naphthyridine-5-yl]-N'-methoxy oxalamide NMR (DMSO-d₆) d: 2.62 (6H, s), 3.71 (3H, s), 4.25 (2H, s), 7.11-7.18 (2H, m), 7.33-7.38 (2H, m), 8.24 (1H, s), 9.09 (1H, d, J=2.1 Hz), 9.83 (1H, br s), 11.03 (1H, br s), 12.35 (1H, br s), 13.70 (1H, br s).

A-11

N-[7-(N',N'-dimethylhydrazinocarbonyl)-3-(4-fluorobenzyl)-8-hydroxy[1,6]naphthyridine-5-yl]-N'-methyl oxalamide NMR (CDCl₃) d: 2.82 (6H, s), 3.04 (3H, d, J=5.2 Hz), 4.20 (2H, s), 6.98-7.07 (2H, m), 7.13-7.21 (2H, m), 7.46-7.54 (1H, m), 7.93 (1H, d, J=1.8 Hz), 8.61 (1H, br s), 9.03 (1H, d, J=1.8 Hz), 9.66 (1H, s), 12.95 (1H, br s).

A-12

2-(N',N'-dimethylhydrazino)-N-[7-(N',N'-dimethylhydrazinocarbonyl)-3-(4-fluorobenzyl)-8-hydroxy[1,6]naphthyridine-5-yl]-2-oxoacetamide NMR (CDCl₃) d: 2.73 (6H, s), 2.78 (6H, s), 4.21 (2H, s), 6.99-7.07 (2H, m), 7.13-7.21 (2H, m), 7.88 (1H, d, J=2.0 Hz), 8.10 (1H, br s), 8.47 (1H, s), 9.04 (1H, d, J=2.0 Hz), 9.61 (1H, s), 13.11 (1H, br s).

A-13. N-[3-(4-fluorobenzyl)-8-hydroxy-7-(2-methoxyethylcarbamoyl)[1,6]naphthyridine-5-yl]-N'-(2-methoxyethyl)oxalamide NMR (CDCl₃) d: 3.42 (3H, s), 3.44 (3H, s), 3.55-3.65 (6H, m), 3.65-3.73 (2H, m), 4.21 (2H, s), 6.98-7.07 (2H, m), 7.13-7.21 (2H, m), 7.72-7.79 (1H, m), 7.94 (1H, d, J=2.1 Hz) 8.05-8.12 (1H, m), 9.03 (1H, d, J=2.1 Hz), 9.61 (1H, s), 13.34 (1H, s).

A-14

5-[(N',N'-dimethylhydrazinooxalyl)amino]-3-(4-fluorobenzyl)-8-hydroxy[1,6]naphthyridine-7-carboxylic acid (2-methoxyethyl)amide NMR (CDCl₃) d: 2.73 (6H, s), 3.43 (3H, s), 3.58-3.67 (2H, m), 3.66-3.73 (2H, m), 4.21 (2H, s), 6.98-7.07 (2H, m), 7.14-7.20 (2H, m), 7.87 (1H, d, J=2.1 Hz), 8.46-8.16 (m, 2H), 9.03 (1H, d, J=2.1 Hz), 9.60 (1H, s), 13.36 (1H, s).

A-15

N-[3-(4-fluorobenzyl)-8-hydroxy-7-(2-methoxyethylcarbamoyl)[1,6]naphthyridine-5-yl]-N',N'-dimethyl oxalamide NMR (CDCl₃) d: 3.13 (3H, s), 3.42 (6H, s), 3.58-3.63 (2H, m), 3.65-3.71 (2H, m), 4.20 (2H, s), 6.98-7.06 (2H, m), 7.14-7.22 (2H, m), 7.89 (1H, s), 8.09 (1H, br s), 9.03 (1H, d, J=2.1 Hz), 9.61 (1H, br s), 13.31 (1H, s).

Example A-16 to A-19

According to the method of Example A-4, Compounds A-16 to A-19 were synthesized.

[Formula 13]

A-16: R³ = —CH₂CH₂OMe, R = —CH₂CH₂OMe,
A-17: R³ = —CH₂CH₂OMe, R = —NMe₂
A-18: R³ = —CH₂CH₂OMe R = (propyl-morpholine)
A-19: R³ = —CH₂CH₂OMe R = (butyl-morpholine)

A-16

3-(4-fluorobenzyl)-8-hydroxy[1,6]naphthyridine-5,7-dicarboxylic acid bis[(2-methoxyethyl)amide]

NMR (CDCl₃) d: 3-0.44 (3H, s), 3.45 (3H, s), 3.61-3.69 (4H, m), 3.69-3.78 (4H, m), 4.20 (2H, s), 6.97-7.05 (2H, m), 7.16-7.23 (2H, m), 7.99 (1H, br s), 8.15 (1H, br s), 9.01 (1H, d, J=2.0 Hz), 9.74 (1H, d, J=2.0 Hz), 13.79 (1H, s).

A-17

5-(N',N'-dimethylhydrazinocarbonyl)-3-(4-fluorobenzyl)-8-hydroxy[1,6]naphthyridine-7-carboxylic acid (2-methoxyethyl)amide NMR (CDCl$_3$) d: 2.83 (6H, s), 3.48 (3H, s), 3.66-3.71 (2H, m), 3.71-3.78 (2H, m), 4.21 (2H, s), 6.96-7.05 (2H, m), 7.17-7.24 (2H, m), 8.18 (1H, br s), 8.34 (1H, br s), 9.01 (1H, d, J=2.1 Hz), 9.56 (1H, d, J=2.1 Hz), 13.77 (1H, br s).

A-18

3-(4-fluorobenzyl)-8-hydroxy[1,6]naphthyridine-5,7-carboxylic acid 7-[(2-methoxyethyl)amide]

5-[(2-morpholine-4-ylethyl)amide]

NMR (CDCl$_3$) d: 2.55-2.59 (4H, m), 2.68 (2H, t, J=6.0 Hz), 3.41 (3H, s), 3.58-3.64 (4H, m), 3.72-3.81 (6H, m), 4.20 (2H, s), 6.96-7.04 (2H, m), 7.15-7.22 (2H, m), 8.16-8.25 (2H, m), 9.00 (1H, d, J=2.2 Hz), 9.74 (1H, d, J=2.2 Hz), 13.77 (1H, br s).

A-19

3-(4-fluorobenzyl)-8-hydroxy[1,6]naphthyridine-5,7-carboxylic acid 7-[(2-methoxyethyl)amide]

5-[(2-morpholine-4-ylpropyl)amide]

NMR (CDCl$_3$) d: 1.95 (2H, t, J=6.2 Hz), 2.58-2.70 (6H, m), 3.42 (3H, s), 3.57-3.69 (4H, m), 3.69-3.80 (6H, m), 4.20 (2H, s), 6.96-7.05 (2H, m), 7.16-7.23 (2H, m), 8.54 (2H, br s), 9.00 (1H, d, J=2.0 Hz), 9.72 (1H, d, J=2.0 Hz), 13.89 (1H, br s).

Example A-20

The present invention also comprehends the following compounds. Such compounds may be synthesized in the same manner as the above Examples.

[Formula 14]

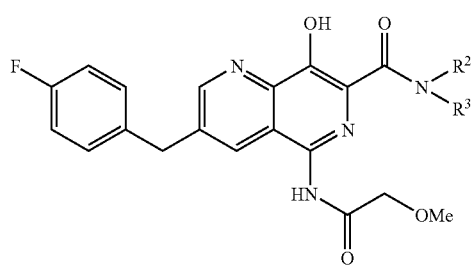

(I-1)

Structure of —NR$^2$R$^3$ moiety is shown below.

TABLE 2

| No. | Structure |
|---|---|
| 001 | —NH—iPr |
| 002 | —NH—CH$_2$CH$_2$—C≡N |
| 003 | —NH—CH$_2$CH$_2$—O—iPr |
| 004 | —NH—CH$_2$CH$_2$—S(=O)$_2$—CH$_3$ |
| 005 | —N(CH$_2$OH)$_2$ |
| 006 | —NH—C(CH$_3$)=CH—C≡N |
| 007 | —N(Et)$_2$ |
| 008 | —NH—NH—C(=O)—C(=O)—NH$_2$ |
| 009 | —N(CH$_3$)—CH$_2$—C≡N |
| 010 | —NH—CH$_2$—CF$_3$ |
| 011 | —HN—NH—C(=S)—NH$_2$ |
| 012 | —NH—NH—C(=O)—O—CH$_3$ |
| 013 | —NH—CH$_2$CH$_2$CH$_2$—S—CH$_3$ |

TABLE 2-continued
| No. | Structure |
|---|---|
| 014 | 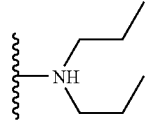 |
| 015 | 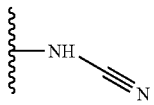 |
| 016 | 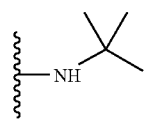 |
| 017 | 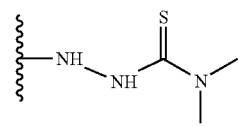 |
| 018 | 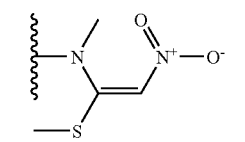 |
| 019 | 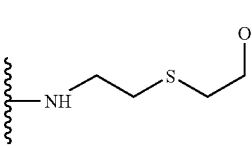 |
| 020 | 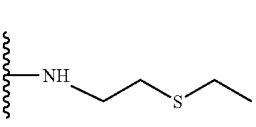 |
TABLE 3
| No. | Structure |
|---|---|
| 021 | 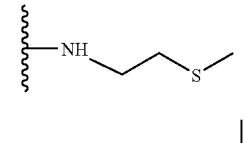 |
| 022 | 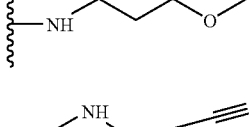 |
| 023 | 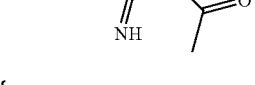 |
| 024 | 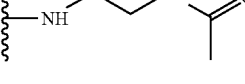 |
TABLE 3-continued
| No. | Structure |
|---|---|
| 025 | 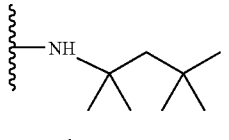 |
| 026 | 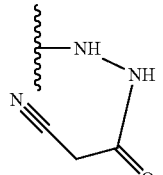 |
| 027 | 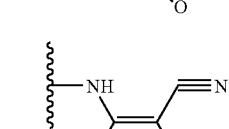 |
| 028 | 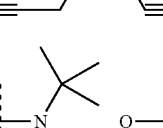 |
| 029 | 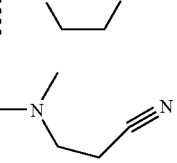 |
| 030 | 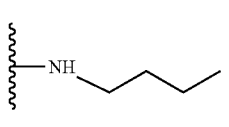 |
| 031 | 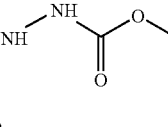 |
| 032 | 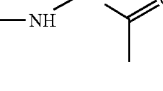 |
| 033 | 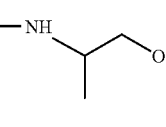 |
| 034 | 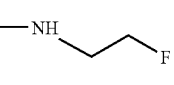 |
| 035 | 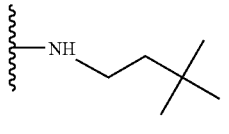 |
| 036 | 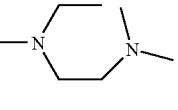 |

TABLE 3-continued
| No. | Structure |
|---|---|
| 037 | 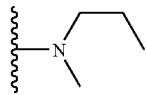 |
| 038 | 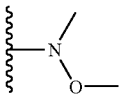 |
| 039 | 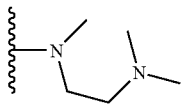 |
| 040 | 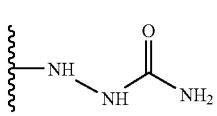 |
TABLE 4
| No. | Structure |
|---|---|
| 041 | 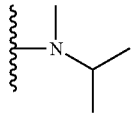 |
| 042 | 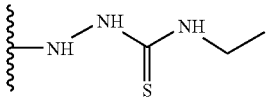 |
| 043 | 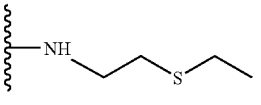 |
| 044 | 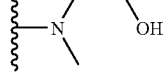 |
| 045 | 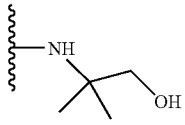 |
| 046 | 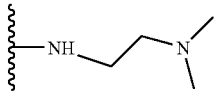 |
| 047 | 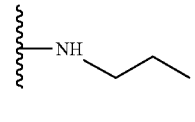 |
| 048 | 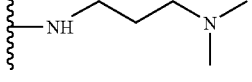 |
TABLE 4-continued
| No. | Structure |
|---|---|
| 049 | 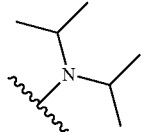 |
| 050 | 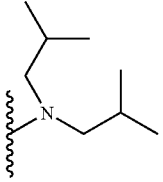 |
| 051 | 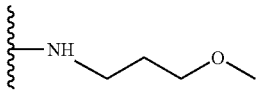 |
| 052 | 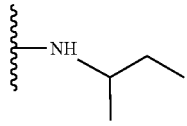 |
| 053 | 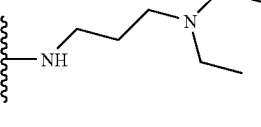 |
| 054 | 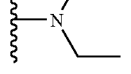 |
| 055 | 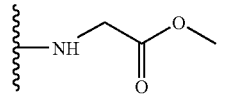 |
| 056 | 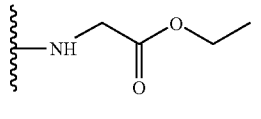 |
| 057 | 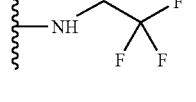 |
| 058 | 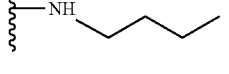 |
| 059 | 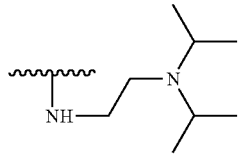 |
| 060 | 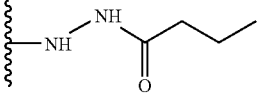 |

TABLE 5

| No. | Structure |
|-----|-----------|
| 061 | 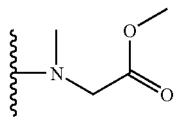 |
| 062 | 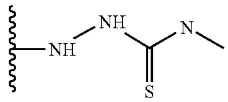 |
| 063 | 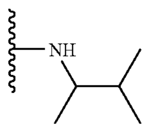 |
| 064 | 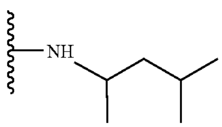 |
| 065 | 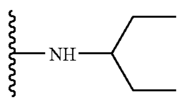 |
| 066 | 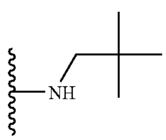 |
| 067 | 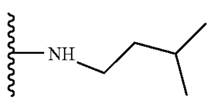 |
| 068 | 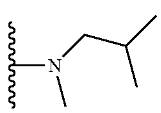 |
| 069 | 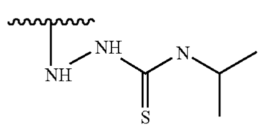 |
| 070 | 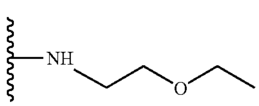 |
| 071 | 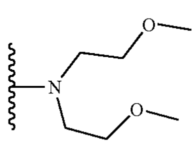 |
| 072 | 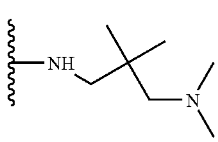 |

TABLE 5-continued

| No. | Structure |
|-----|-----------|
| 073 | 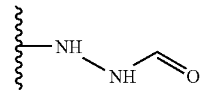 |
| 074 | 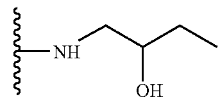 |
| 075 | 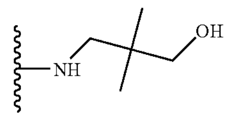 |
| 076 | 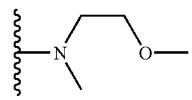 |
| 077 | 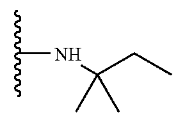 |
| 078 | 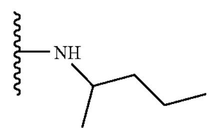 |
| 079 | 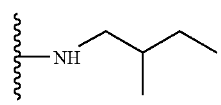 |
| 080 | 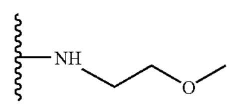 |

TABLE 6

| No. | Structure |
|-----|-----------|
| 081 | 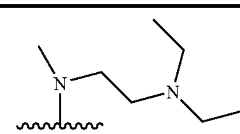 |
| 082 | 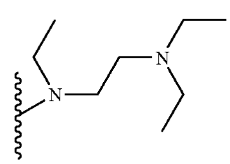 |
| 083 | 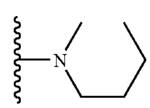 |
| 084 | 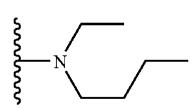 |

TABLE 6-continued

| No. | Structure |
|---|---|
| 085 | —NH-CH(propyl)(butyl) |
| 086 | —N(ethyl)(isopropyl) |
| 087 | —N(ethyl)(ethyl) |
| 088 | —N(propyl)(sec-butyl) |
| 089 | —N(propyl)(CH₂CH₂OCH₃) |
| 090 | —NH-NH-C(=S)-NH-CH₂-CH=CH₂ |
| 091 | —NH-CH(CH₃)-C(CH₃)₃ |
| 092 | —NH-CH₂CH₂CH₂-O-isopropyl |
| 093 | —NH-NH-C(=O)-CH₂CH₂-OH |
| 094 | —NH-CH(CH₃)-C(=O)-O-CH₃ |
| 095 | —N(CH₂CN)₂ |
| 096 | —NH-CH₂-CH(OH)-CH₃ |

TABLE 6-continued

| No. | Structure |
|---|---|
| 097 | —NH-CH₂-CH(CH₃)₂ |
| 098 | —NH-CH₂CH₂-O-CH₂CH₂-OH |
| 099 | —NH-CH₂CH₂CH₂-OH |
| 100 | —NH-CH(CH₂OH)-CH(CH₃)(ethyl) |

TABLE 7

| No. | Structure |
|---|---|
| 101 | —NH-CH₂CH₂-N(ethyl)₂ |
| 102 | —N(butyl)₂ |
| 103 | —NH-CH₂-CN |
| 104 | —N(CH₃)-CH₂CH₂CH₂-N(CH₃)₂ |
| 105 | —NH-CH₂-CH(CH₃)₂ |
| 106 | —NH-CH(CH₃)-ethyl |
| 107 | —NH-CH(CH(CH₃)₂)-CH₂OH |

TABLE 7-continued

| No. | Structure |
|---|---|
| 108 | 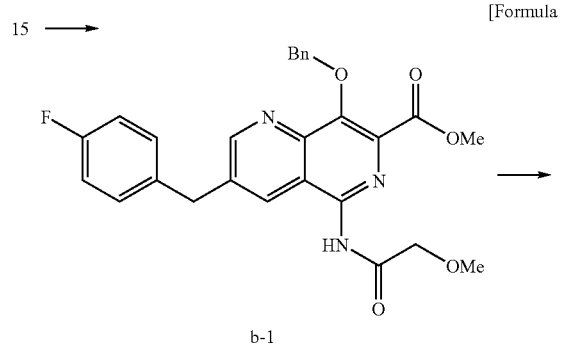 |
| 109 | 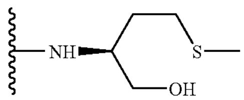 |
| 110 | 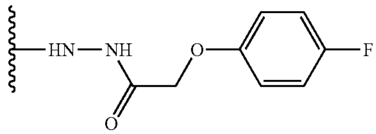 |
| 111 | 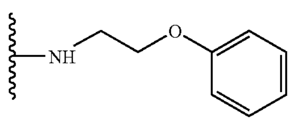 |
| 112 | 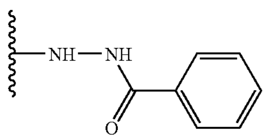 |
| 113 | 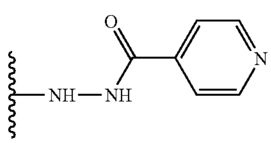 |
| 114 | 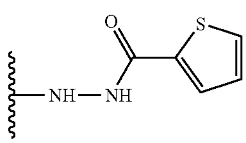 |

Example B-1

[Formula 15]

15 →

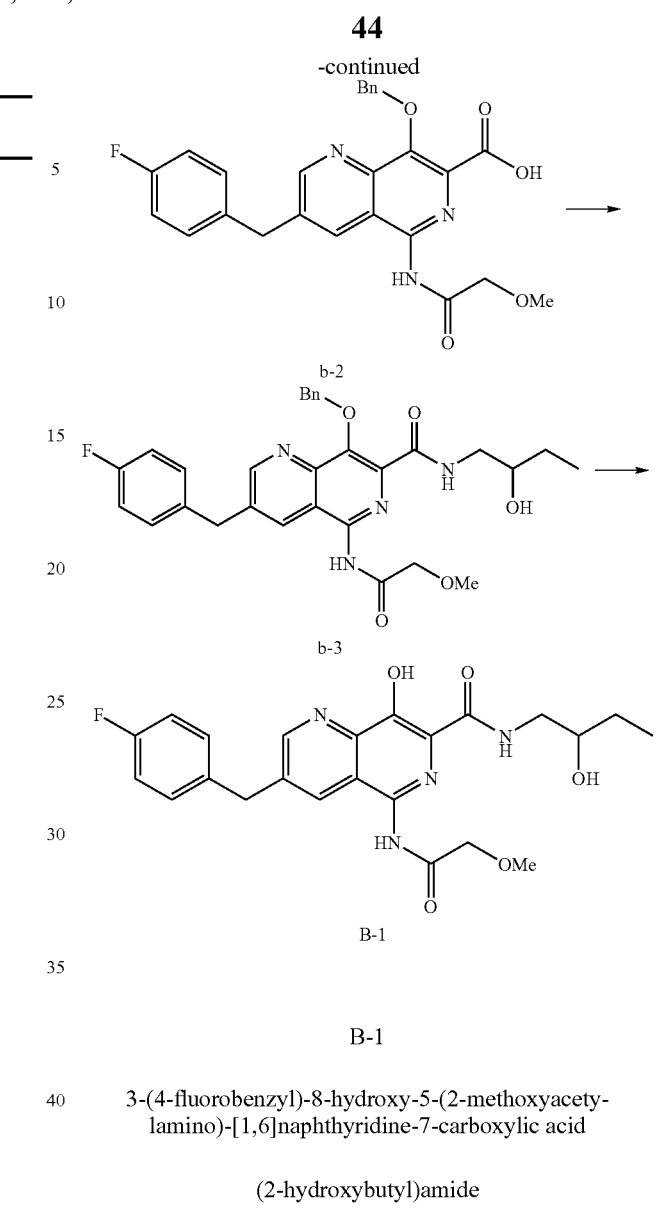

B-1

3-(4-fluorobenzyl)-8-hydroxy-5-(2-methoxyacetylamino)-[1,6]naphthyridine-7-carboxylic acid (2-hydroxybutyl)amide 1) A dichloromethane (100 ml) solution of Compound 15 (8.5 g, 20.4 mmol) and pyridine (2.47 ml, 30.6 mmol) was cooled on ice, added with methoxyacetyl chloride (2.23 ml, 24.5 mmol), stirred or 50 minutes at the same temperature, and then stirred for 1 hour at room temperature. After adding 0.5 M citric acid aqueous solution, the mixture was extracted with chloroform. The organic phase was washed with water and saturated brine. After drying over anhydrous sodium sulfate, the solvent was distilled off, and the resultant residue was subjected to silica gel chromatography. The obtained crystals were washed with methanol, to give methyl 8-benzyloxy-3-(4-fluorobenzyl)-5-(2-methoxyacetylamino)-[1,6]naphthyridine-7-carbonate b-1 (8.11 g) in 81% yield.

NMR (CDCl$_3$) d: 3.55 (3H, s), 3.94 (3H, s), 4.13 (2H, s), 4.21 (2H, s), 5.52 (2H, s), 7.00-7.06 (2H, m), 7.19-7.27 (2H, m), 7.33-7.43 (3H, m), 7.57-7.61 (2H, m), 8.06 (1H, s), 8.98 (1H, br s), 9.01 (1H, d, J=1.8 Hz).

2) According to the method of 5) in Example A-3, from the above Compound b-1 (7.86 g, 16.1 mmol), 8-benzyloxy-3-(4-fluorobenzyl)-5-(2-methoxyacetylamino)-[1,6]naphthyridine-7-carboxylic acid b-2 (6.85 g) was obtained in 90% yield.

NMR (CDCl$_3$) d: 3.57 (3H, s), 4.15 (2H, s), 4.23 (2H, s), 5.72 (2H, s), 7.00-7.08 (2H, m), 7.18-7.23 (2H, m), 7.34-7.39 (3H, m), 7.56-7.60 (2H, m), 8.09 (1H, s), 9.06 (1H, d, J=2.1 Hz), 9.06 (1H, br s).

3) According to the method of 9) in Example A-1, from the above Compound b-2 (200 mg, 0.421 mmol), 8-benzyloxy-3-(4-fluorobenzyl)-5-(2-methoxyacetylamino)-[1,6]naphthyridine-7-carboxylic acid (2-hydroxybutyl)amide b-3 (223 mg) was obtained in 97% yield.

NMR (DMSO-d$_6$) d: 0.94 (3H, t, J=7.4 Hz), 1.48 (2H, qui, J=7.4 Hz), 3.21-3.31 (1H, m), 3.51-3.67 (2H, m), 3.55 (3H, s), 4.16 (2H, s), 4.21 (2H, s), 5.56 (2H, s), 6.99-7.08 (2H, m), 7.18-7.24 (2H, m), 7.35-7.43 (3H, m), 7.56-7.60 (2H, m), 8.11 (1H, br s), 8.20-8.24 (1H, m), 9.00 (1H, d, J=1.8 Hz), 9.03 (1H, br s).

4) According to the method of 11) in Example A-1, B-1 (126 mg) was obtained in 68% yield from the above Compound b-3 (215 mg, 0.408 mmol).

Melting point: 75-77° C.

NMR (CDCl$_3$) d: 1.03 (3H, t, J=7.4 Hz), 1.51-1.67 (2H, m), 3.37 (1h, ddd, J=14.0, 7.9, 5.9 hz), 3.57 (3H, s), 3.72 (1H, ddd, J=14.0, 6.9, 3.0 Hz), 3.78-3.85 (1H, m), 4.12 (2H, s), 4.20 (2H, s), 6.98-7.07 (2H, m), 7.14-7.20 (2H, m), 7.92 (1H, s), 8.20 (1H, t, J=6.1 Hz), 8.69 (1H, s), 8.98 (1H, d, J=2.1 Hz), 13.18 (1H, br s).

Example B-2

8 ⟶ [Formula 16]

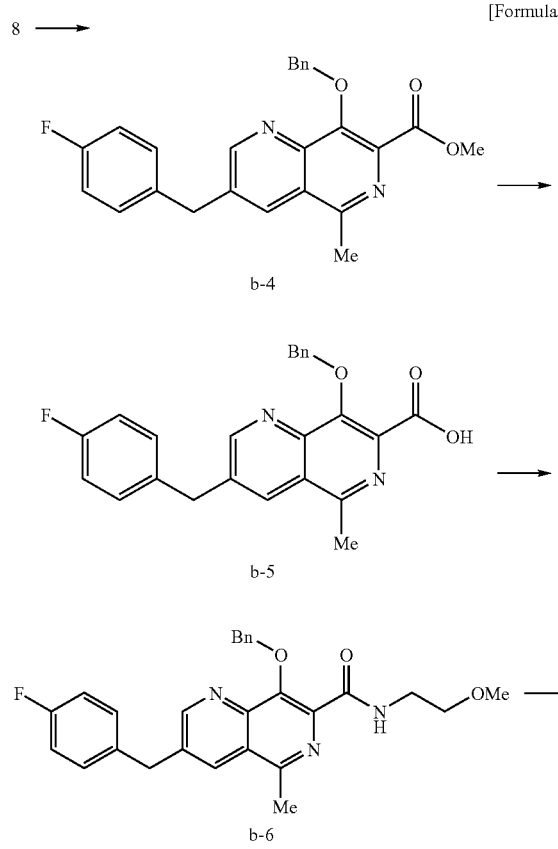

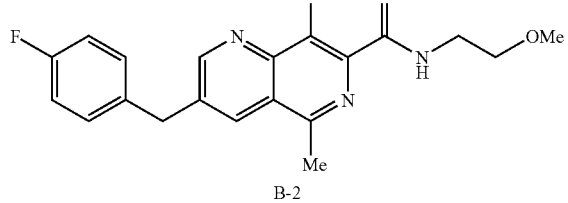

B-2

3-(4-fluorobenzyl)-8-hydroxy-5-methyl[1,6]naphthyridine-7-carboxylic acid (2-methoxyethyl)amide 1) Compound 8 (2.113 g, 4.0 mmol) and potassium phosphate (4.24 g, 20 mmol) were put into a reaction flask, and after drying in vacuo, tetrakistriphenyl phosphine palladium (462 mg, 0.4 mmol), methyl boronate (599 mg, 10 mmol) was added and suspended in dioxane (48 ml). Vacuum deaeration under stirring at room temperature was carried out followed by heating under stirring in an oil bath at 100° C. After 3.5 hours, the reaction was left overnight at room temperature. On the next day, the reaction mixture was added with ethyl acetate ester (150 ml) and water (150 ml), as well as 10% citric acid (60 ml), shaken for separation, washed once with brine, dried over sodium sulfate, and the subjected to distillation under reduce pressure. The obtained residue (2.58 g) was subjected to high flash column chromatography (hexane: ethyl acetate ester (2:1)), and the gathered fractions were combined and subjected to distillation. The residue (467 mg) was added with diisopropyl ether and caused to crystallize, to give methyl 8-benzyloxy-3-(4-fluorobenzyl)-5-methyl[1,6]naphthyridine-7-carbonate b-4 (407 mg) as ocher crystals in 24.4% yield.

NMR (CDCl$_3$) d: 2.90 (3H, s), 3.95 (3H, s), 4.23 (2H, s), 5.50 (2H; s), 7.02-7.08 (2H, m), 7.19-7.23 (2H, m), 7.32-7.41 (3H, m), 7.58-7.61 (2H, m), 8.13 (1H, m), 9.04 (1H, d, J=2.1 Hz).

2) According to the method of 5) in Example A-3, from the above Compound b-4 (815 mg, 1.96 mmol), 8-benzyloxy-3-(4-fluorobenzyl)-5-methyl[1,6]naphthyridine-7-carboxylic acid b-5 (740 mg) was obtained in 93.9% yield.

NMR (CDCl$_3$) d: 2.87 (3H, s), 4.25 (2H, s), 5.62 (2H, s), 7.03-7.09 (2H, m), 7.18-7.23 (2H, m), 7.31-7.38 (3H, m), 7.64-7.66 (2H, m), 8.13 (1H, m), 9.09 (1H, d, J=2.1 Hz).

3) According to the method of 9) in Example A-1, from the above Compound b-5 (201 mg, 0.5 mmol), 8-benzyloxy-3-(4-fluorobenzyl)-5-methyl[1,6]naphthyridine-7-carboxylic acid (2-methoxyethyl) amide b-6 (180 mg) was obtained in 78.3% yield.

NMR (DMSO-d$_6$) d: 2.88 (3H, s), 3.36 (3H, s), 3.54-3.58 (2H, m), 3.64-3.70 (2H, m), 4.22 (2H, s), 5.48 (2H, s), 7.02-7.08 (2H, m), 7.18-7.23 (2H, m), 7.31-7.40 (3H, m), 7.65-7.67 (2H, m), 8.11 (1H, m), 8.24 (1H, m), 9.03 (1H, d, J=2.1 Hz).

4)-According to the method of 11) in Example A-1, from the above Compound b-6 (177 mg, 0.385 mmol), Compound B-2 (109 mg) was obtained in 76.8% yield.

Melting point: 167-168° C.
Elemental analysis for C$_{20}$H$_{20}$FN$_3$O$_3$
Calcd.(%): C, 65.03; H, 5.46; F, 5.14; N, 11.38.
Found.(%): C, 64.91; H, 5.51; F, 5.08; N, 11.26.
NMR (CDCl$_3$) d: 12.76 (3H, s), 3.44 (3H, s), 3.61-3.64 (2H, m), 3.68-3.73 (2H, m), 4.21 (2H, s), 7.01-7.06 (2H, m), 7.16-7.21 (2H, m), 8.03 (1H, d, J=2.1 Hz), 8.40 (1H, m), 9.01 (1H, d, J=2.1 Hz), 13.09 (1H, s).

Example B-3

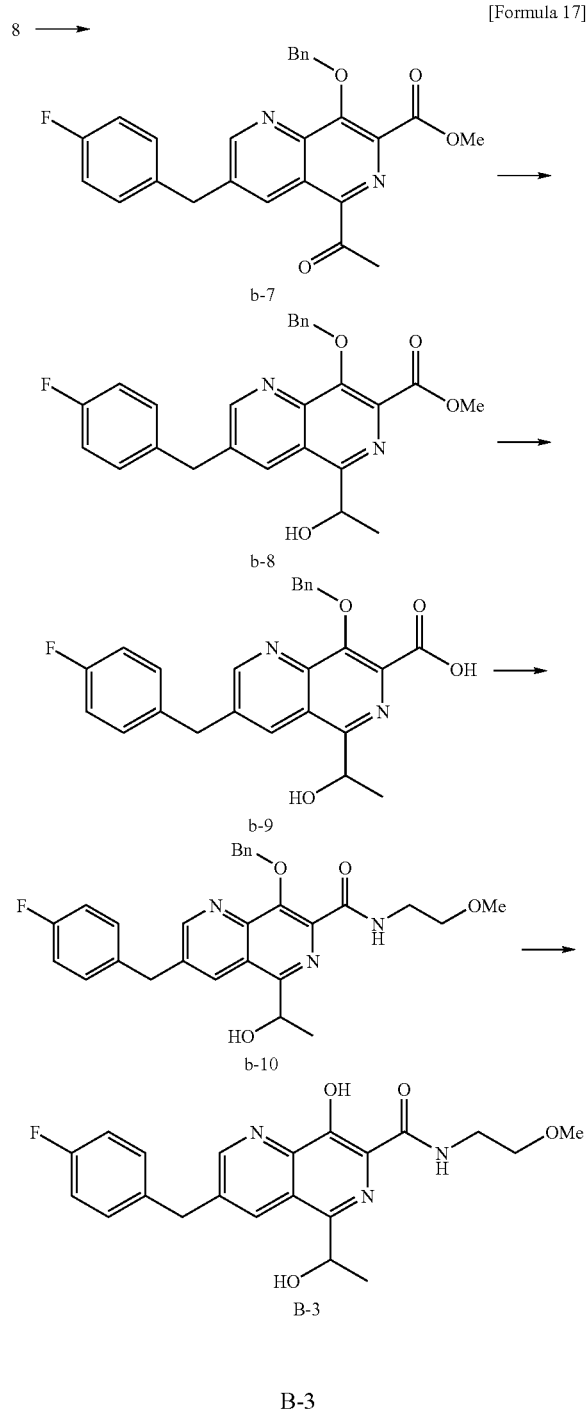

B-3

3-(4-fluorobenzyl)-8-hydroxy-5-(1-hydroxyethyl)[1,6]naphthyridine-7-carboxylic acid (2-methoxyethyl) amide 1) To Compound 8 (1.585 g, 3 mmol) was added toluene (60 ml), and the resultant solution was stirred at room temperature in nitrogen gas flow, added with tetrakistriphenylphosphine palladium (522 mg, 0.452 mmol) followed by tributyl(1-ethoxyvinyl)tin (2.04 ml, 6.04 mmol), and heated in an oil bath at 100° C. under stirring. After 4 hours, the mixture was let stand at room temperature, and on the next day, the reaction mixture was subjected to distillation under reduced pressure and added with tetrahydrofuran (60 ml). Then the mixture was stirred at room temperature, added with 2N hydrochloric acid (6 ml), stirred for 30 minutes, added with ethyl acetate ester (140 ml) and water (100 ml), shaken for separation, and washed with saturated brine. Then the mixture was concentrated under reduced pressure, added with an water (20 mL) solution of potassium fluoride (4 g), and stirred for 30 minutes at room temperature. Then the precipitated insoluble matters were filtered off, and washed with ethyl acetate ester, and the filtration wash liquid was gathered and subjected to separation. After one washing with water and drying over sodium sulfate, distillation under reduce pressure was conducted. The obtained residue (2.65 g) was subjected to high flash column chromatography (hexane:ethyl acetate ester (7:1)), and the gathered fractions were combined and subjected to distillation. The obtained residue was crystallized from diisopropyl ether, to give methyl 5-acetyl-8-benzyloxy-3-(4-fluorobenzyl)[1,6]naphthyridine-7-carbonate b-7 (1.164 g) as yellow powder in 87.3% yield.

NMR (CDCl$_3$) d: 2.85 (3H, s), 3.96 (3H, s), 4.21 (2H, s), 5.70 (2H, s), 7.00-7.06 (2H, m), 7.19-7.24 (2H, m), 7.33-7.40 (3H, m), 7.53-7.56 (2H, m), 9.01 (1H, d, J=2.1 Hz), 9.33 (1H, m).

2) To the above Compound b-7 (441 mg, 0.992 mmol) was added methanol (40 ml), and the mixture was warmed on water bath and stirred at room temperature. After adding sodium borohydride (38 mg, 1.004 mmol) at a time, the mixture was stirred. After 2 hours, the reaction solution was poured into the ammonium chloride aqueous solution and ice water, extracted with ethyl acetate ester, washed with brine, dried over sodium sulfate, and then subjected to distillation under reduced pressure. The resultant residue (0.56 g) was subjected to high flash chromatography (toluene:acetone (9:1)), and gathered fractions were combined and subjected to distillation. The obtained residue was dissolved in ethyl acetate ester, and added with 2N hydrochloric acid and water. The mixture was shaken for separation, washed with water, washed with sodium hydrogen carbonate aqueous solution, and further washed once with water. Then the mixture was dried over sodium sulfate and subjected to distillation under reduced pressure, to give methyl 8-benzyloxy-3-(4-fluorobenzyl)-5-(1-hydroxyethyl)[1,6]naphthyridine-7-carbonate b-8 (406 mg) as oil in 91.6% yield.

NMR (CDCl$_3$) d: 1.55 (3H, d, J=6.6 Hz), 3.94 (3H, s), 4.23 (3H, s), 4.68 (1H, bs), 5.44 (1H, m), 5.52 (2H, s), 7.03-7.08 (2H, m), n 7.17-7.22 (2H, m), 7.34-7.44 (3H, m), 7.58-7.60 (2H, m), 8.15 (1H, d, J=2.1 Hz), 9.06 (1H, d, J=2.1 Hz).

3) According to the method of 5) in Example A-3, from the above Compound b-8 (480 mg, 1.08 mmol), 8-benzyloxy-3-(4-fluorobenzyl)-5-(1-hydroxyethyl)[1,6]naphthyridine-7-carboxylic acid b-9 (420 mg) was obtained in 90.3% yield.

NMR (CDCl$_3$) d: 1.63 (3H, d, J=6.6 Hz), 4.25 (2H, s), 5.49 (1H, quart, J=6.6 Hz), 5.69 (2H, s), 7.03-7.09 (2H, m) 7.18-7.23 (2H, m), 7.35-7.38 (3H, m), 7.59-7.62 (2H, m), 8.36 (1H, m), 9.08 (1H, d, J=2.1 Hz).

4) According to the method of 9) in Example A-1, NMR (DMSO-d$_6$) d: 8-benzyloxy-3-(4-fluorobenzyl)-5-(1-hydroxyethyl)[1,6]naphthyridine-7-carboxylic acid (2-methoxyethyl)amide b-10 (201 mg) was obtained in 88.9% yield from the above Compound b-9 (200 mg, 0.463 mmol).

NMR (DMSO-d$_6$) d: 1.58 (3H, d, K=6.6 hz), 3.34 (3H, s), 3.52-3.55 (2H, m), 3.63-3.67 (2H, m), 4.23 (2H, s), 4.45 (1H, bs), 5.43-5.56 (1H, m), 5.50 (1H, d, J=10.5 Hz), 5.54 (1H, d, J=10.5 Hz), 7.02-7.08 (2H, m), 7.18-7.22 (2H, m) 7.33-7.41 (3H, m), 7.63-7.65 (2H, m), 7.96 (1H, m), 8.18 (1H, d, J=2.1 Hz), 9.05 (1H, d, J=2.1 Hz).

5) According to the method of 11) in Example A-1, Compound B-3 (136 mg) was obtained in 84% yield from the above Compound b-10 (198 mg, 0.404 mmol).

Melting point: 179° C.

Elemental analysis for C$_{21}$H$_{22}$FN$_3$O$_4$

Calcd.(%): C, 63.15; H, 5.55; F, 4.76; N, 10.52.

Found.(%): C, 63.15; H, 5.61; F, 4.66; N, 10.38.

NMR (CDCl$_3$) d: 1.56 (3H, d, J=6.6 Hz) 3.43 (3H, s), 3.61-3.64 (2H, m), 3.70-3.75 (2H, m), 4.22 (2H, s), 5.40 (1H, quart, J=6.6 Hz), 7.01-7.07 (2H, m), 7.16-7.20 (2H, m), 8.15 (1H, m), 8.14-8.17 (1H, m), 9.04 (1H, d, J=2.1 Hz).

Example B-4

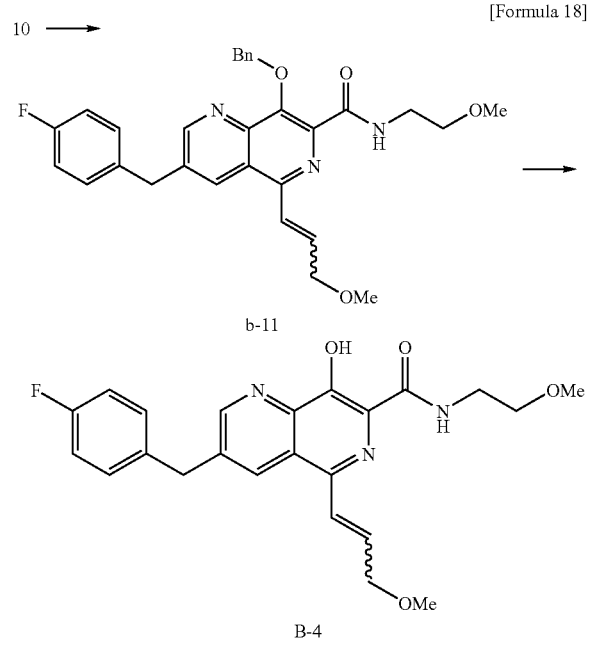

[Formula 18]

b-11

B-4

B-4

3-(4-fluorobenzyl)-8-hydroxy-5-(3-methoxypropenyl)[1,6]naphthyridine-7-carboxylic acid (2-methoxyethyl)amide 1) To Compound 10 (286 mg, 0.5 mmol) and tetrakistriphenyl phosphine palladium (30 mg, 0.026 mmol) was added a dimethylformamide (4 ml) solution of 2-((E)-3-methoxypropenyl)-4,4,5,5-tetramethyl[1,3,2]dioxaborolane (142 mg, 0.65 mmol), followed by an aqueous solution of 2 moles of potassium carbonate (0.66 ml, 1.32 mmol), and after vacuum deaeration under stirring at room temperature, and replacement with nitrogen, the reaction was heated under stirring in an oil bath at 100° C. After 3 hours, to the reaction mixture were added and dissolved ethyl acetate and water, and was added 10% citric acid (8 ml), and then the mixture was shaken for separation, washed twice with water, dried over sodium sulfate, and subjected to distillation under reduced pressure. The residue was subjected to high flash column chromatography (toluene:acetone (4:1)), and the obtained residue (170 mg) was crystallized from diisopropyl ether, to give 8-benzyloxy-3-(4-fluorobenzyl)-5-(3-methoxypropenyl)[1,6]naphthyridine-7-carboxylic acid (2-methoxyethyl)amide b-11 (135 mg) in 52.3% yield.

NMR (CDCl$_3$) d: 3.38 (3H, s), 3.50 (3H, s), 3.56-3.59 (2H, m), 3.66-3.71 (2H, m), 4.21 (2H, s), 4.27 (2H, dd, J=1.8, 4.5 Hz), 5.50 (2H, s), 7.01-7.39 (9H, m), 7.67-7.70 (2H, m), 8.21 (1H, m), 8.31 (1H, d, J=1.8 Hz), 9.01 (1H, d, J=1.8 Hz).

2) According to the method 11) of Example A-1, Compound B-4 (140 mg) was obtained in 84.8% yield from the above Compound b-11 (200 mg, 0.388 mmol).

Melting point: 125-126° C.

Elemental analysis for C$_{23}$H$_{24}$FN$_3$O$_4$

Calcd.(%): C, 64.93; H, 5.69; F, 4.47; N, 9.88.

Found.(%): C, 64.78; H, 5.54; F, 4.24; N, 9.75.

NMR (CDCl$_3$) d: 3.44 (3H, s), 3.49 (3H, s), 3.62-3.65 (2H, m), 3.69-3.74 (2H, m), 4.21 (2H, s), 4.24 (2H, dd, J=1.8, 5.1 Hz), 6.89-6.97 (1H, m), 7.00-7.07 (2H, m), 7.15-7.26 (3H, m), 8.25 (1H, d, J=1.8 Hz), 8.39 (1H, m), 9.00 (1H, d, J=2.1 Hz), 13.27 (1H, s).

Example B-5 to B-16

According to the method of Example B-1, Compounds B-5 to B-16 were synthesized.

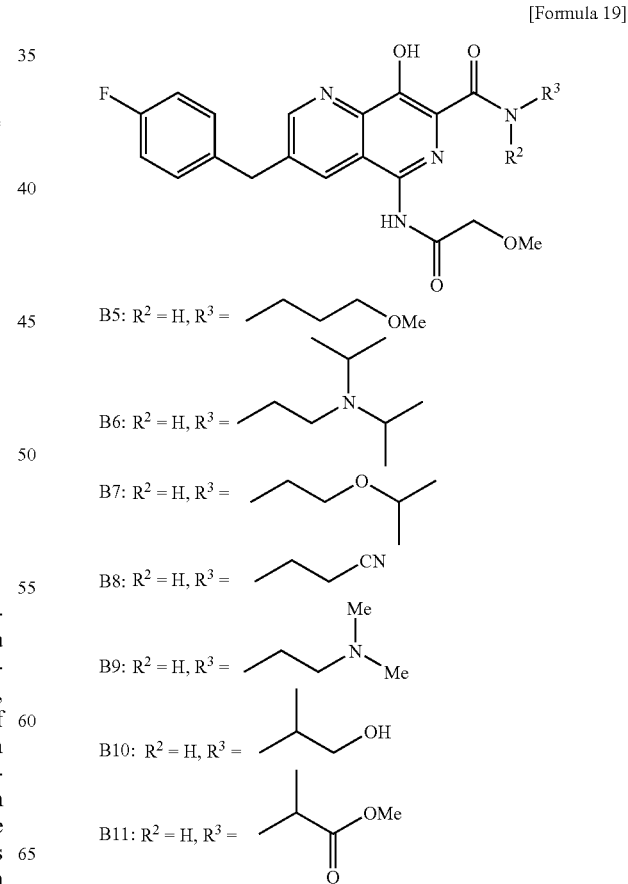

[Formula 19]

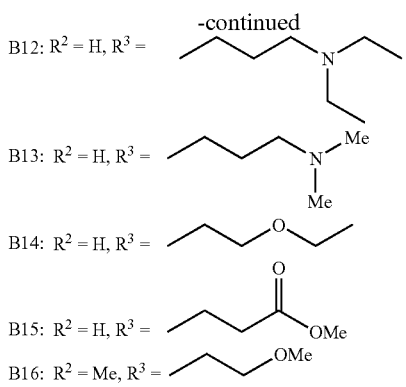

B12: R² = H, R³ = (propyl-N-diethyl chain)

B13: R² = H, R³ = (propyl-N(Me)Me chain)

B14: R² = H, R³ = (ethoxyethyl chain)

B15: R² = H, R³ = (propanoate OMe chain)

B16: R² = Me, R³ = (propyl-OMe chain)

Example B-5

3-(4-fluorobenzyl)-8-hydroxy-5-(2-methoxyacety-lamino)[1,6]naphthyridine-7-carboxylic acid (3-methoxypropyl) amide Melting point: 159-160° C.
Elemental analysis for $C_{23}H_{25}FN_4O_5$
Calcd.(%): C, 60.52; H, 5.52; F, 4.16; N, 12.27.
Found.(%): C, 60.47; H, 5.60; F, 4.09; N, 12.23.
NMR (CDCl$_3$) d: 1.90-1.98 (2H, m), 3.41 (3H, s), 3.55-3.64 (5H, m), 3.57 (3H, s), 4.13 (2H, s), 4.20 (2H, s), 6.99-7.05 (2H, m), 7.15-7.20 (2H, m), 7.94 (1H, s), 8.23-8.27 (1H, m), 9.00 (1H, d, J=2.0 Hz), 13.37 (1H, brs).

Example B-6

3-(4-fluorobenzyl)-8-hydroxy-5-(2-methoxyacety-lamino)[1,6]naphthyridine-7-carboxylic acid (2-diisopropylaminoethyl)amide Melting point: 69-70° C.
Elemental analysis for $C_{27}H_{34}FN_5O_4$
Calcd.(%): C, 63.39; H, 6.70; F, 3.71; N, 13.69.
Found.(%): C, 60.69; H, 6.65; F, 3.34; N, 13.10.
NMR (CDCl$_3$) d: 1.07 (12H, d, J=5.8 Hz), 2.73 (2H, brs), 3.08 (2H, brs), 3.44 (2H, brs), 3.58 (3H, s), 4.12 (2H, s), 4.20 (2H, s), 6.99-7.05 (2H, m), 7.15-7.19 (2H, m), 7.97 (1H, s), 8.34 (1H, brs), 8.62 (1H, brs), 8.99 (1H, d, J=2.1 Hz), 13.39 (1H, brs).

Example B-7

3-(4-fluorobenzyl)-8-hydroxy-5-(2-methoxyacety-lamino)[1,6]naphthyridine-7-carboxylic acid (2-isopropoxyethyl)amide Melting point: 149-150° C.
Elemental analysis for $C_{24}H_{27}FN_4O_5$
Calcd.(%): C, 61.27; H, 5.78; F, 4.04; N, 11.91.
Found.(%): C, 61.16; H, 5.88; F, 3.92; N, 11.79.
NMR (CDCl$_3$) d: 1.21 (6H, d, J=6.1 Hz), 3.58 (3H, s), 3.62-3.70 (5H, m), 4.13 (2H, s), 4.20 (2H, s), 6.99-7.05 (2H, m), 7.15-7.20 (2H, m), 7.95 (1H, s), 8.16 (1H, brs), 8.64 (1H, s), 8.99 (1H, d, J=1.9 Hz), 13.26 (1H, brs).

Example B-8

3-(4-fluorobenzyl)-8-hydroxy-5-(2-methoxyacety-lamino)[1,6]naphthyridine-7-carboxylic acid (2-cya-noethyl)amide Melting point: 173-175° C.
NMR (CDCl$_3$) d: 2.79 (2H, t, J=6.4 Hz), 3.59 (3H, s), 3.78 (2H, q, J=6.4 Hz), 4.14 (2H, s), 4.21 (2H, s), 6.99-7.06 (2H, m), 7.94 (1H, d, J=2.1 Hz), 8.21 (1H, t, J=6.1 Hz), 8.69 (1H, s), 9.02 (1H, d, J=2.1 Hz), 12.79 (1H, br s).

Example B-9

3-(4-fluorobenzyl)-8-hydroxy-5-(2-methoxyacety-lamino)[1,6]naphthyridine-7-carboxylic acid (2-dimethylaminoethyl)amide Melting point: 164-166° C.
NMR (DMSO-d$_6$) d: 2.21 (6H, s), 2.45-2.51 (2H, m), 3.39 (3H, s), 3.43-3.50 (2H, m), 4.15 (2H, s), 4.25 (2H, s), 7.12-7.19 (2H, m), 7.32-7.38 (2H, m), 8.12 (1H, s), 8.76 (1H, t, J=5.6 Hz), 9.08 (1H, d, J=1.8 Hz), 10.26 (1H, s), 13.49 (1H, br s).

Example B-10

3-(4-fluorobenzyl)-8-hydroxy-5-(2-methoxyacety-lamino)[1,6]naphthyridine-7-carboxylic acid (2-hydroxy-1-methylethyl)amide Melting point: 85-87° C.
NMR (CDCl$_3$) d: 1.36 (3H, d, J=6.9 Hz), 3.58 (3H, s), 3.71 (1H, dd, J=11.1, 5.8 Hz), 3.84 (1H, dd, J=11.1, 3.8 Hz), 4.13 (2H, s), 4.20 (2H, s), 4.25-4.35 (1H, m), 6.99-7.06 (2H, m), 7.15-7.21 (2H, m), 7.91 (1H, s), 7.93 (1H, s), 8.67 (1H, s), 8.99 (1H, d, J=2.1 Hz), 13.18 (1H, br s).

Example B-11

Methyl

2-{[3-(4-fluorobenzyl)-8-hydroxy-5-(2-methoxy-acetylamino)[1,6]naphthyridine-7-carbonyl] amino}propionate Melting point: 181-182° C.
Elemental analysis for $C_{23}H_{23}FN_4O_6$
Calcd.(%): C, 58.72; H, 4.93; F, 4.04; N, 11.91.
Found.(%): C, 58.62; H, 4.84; F, 3.80; N, 11.86.
NMR (CDCl$_3$) d: 1.58 (3H, s), 3.59 (3H, s), 3.82 (3H, s), 4.14 (2H, s), 4.20 (2H, s), 4.77-4.87 (1H, m), 7.00-7.05 (2H, m), 7.15-7.20 (2H, m), 7.94 (1H, m), 8.26 (1H, d, J=7.8 Hz), 8.66 (1H, s), 9.00 (1H, d, J=2.1 Hz), 12.95 (1H, s).

Example B-12

3-(4-fluorobenzyl)-8-hydroxy-5-(2-methoxyacety-lamino)[1,6]naphthyridine-7-carboxylic acid (3-diethylaminopropyl)amide NMR (CDCl$_3$) d: 1.13 (3H, d, J=6 Hz), 1.25 (6H, trip, J=6.9 Hz), 2.06 (2H, bs), 2.94 (6H, bs), 3.58 (3H, s), 3.58-3.67 (2H, m), 4.13 (2H, s), 4.20 (2H, s), 6.99-7.05 (2H, m), 7.15-7.20 (2H, m), 7.96 (1H, s), 8.65 (1H, bs), 8.74 (1H, bs), 8.99 (1H, d, J=2.1 Hz), 13.15 (1H, bs).

Example B-13

3-(4-fluorobenzyl)-8-hydroxy-5-(2-methoxyacetylamino)[1,6]naphthyridine-7-carboxylic acid (3-dimethylaminopropyl)amide NMR (CDCl$_3$) d: 1.96-2.00 (2H, m), 2.51 (6H, s), 2.71-2.75 (2H, m), 3.56-3.60 (2H, m), 3.58 (3H, s), 4.13 (2H, s), 4.20 (2H, s), 6.99-7.05 (2H, m), 7.15-7.20 (2H, m), 7.96 (1H, m), 8.67 (1H, bs), 8.70 (1H, s), 8.99 (1H, d, J=2.1 Hz), 13.30 (1H, bs).

Example B-14

3-(4-fluorobenzyl)-8-hydroxy-5-(2-methoxyacetylamino)[1,6]naphthyridine-7-carboxylic acid (2-ethoxyethyl)amide Melting point: 175-177° C.
Elemental analysis for C$_{23}$H$_{25}$FN$_4$O$_5$
Calcd.(%): C, 60.52; H, 5.52; F, 4.16; N, 12.27.
Found.(%): C, 60.59; H, 5.38; F, 3.93; N, 12.17.
NMR (CDCl$_3$) d: 1.25 (3H, t, J=7.0 Hz), 3.56-3.62 (5H, m), 3.64-3.73 (4H, m), 4.14 (2H, s), 4.20 (2H, s), 6.99-7.04 (2H, m), 7.15-7.22 (2H, m), 7.95 (1H, s), 8.12 (1H, m), 8.64 (1H, s), 9.00 (1H, s), 13.26 (1H, s).

Example B-15

Methyl 3-([3-(4-fluorobenzyl)-8-hydroxy-5-(2-methoxyacetylamino)[1,6]naphthyridine-7-carbonyl]amino) propionate Melting point: 168-170° C.
Elemental analysis for C$_{23}$H$_{23}$FN$_4$O$_6$
Calcd.(%): C, 58.72; H, 4.93; F, 4.04; N, 11.91.
Found.(%): C, 58.56; H, 4.83; F, 3.90; N, 11.80.
NMR (CDCl$_3$) d: 2.72 (2H, t, J=6.2 Hz), 3.74-3.81 (5H, m), 4.13 (2H, s), 4.21 (2H, s), 6.99-7.05 (2H, m), 7.15-7.20 (2H, m), 7.93 (1H, s), 8.22 (1H, m), 8.63 (1H, s), 9.00 (1H, s), 13.18 (1H, s).

Example B-16

3-(4-fluorobenzyl)-8-hydroxy-5-(2-methoxyacetylamino)[1,6]naphthyridine-7-carboxylic acid (2-methoxyethyl)methylamide Melting point: 66-68° C.
Elemental analysis for C$_{23}$H$_{23}$FN$_4$O$_6$
Calcd.(%): C, 58.72; H, 4.93; F, 4.04; N, 11.92.
Found.(%): C, 58.56; H, 4.83; F, 3.90; N, 11.80.
NMR (CDCl$_3$) d: 3.36 (6H, s), 3.55 (3H, s), 3.72 (2H, t, J=5.2 Hz), 4.11 (2H, s), 4.20 (2H, s), 6.99-7.05 (2H, m), 7.15-7.20 (2H, m), 7.92 (1H, s), 8.66 (1H, bs), 8.98 (1H, s).

Example B-17

According to the method of Example B-2, Compound B-17 was synthesized.

[Formula 20]

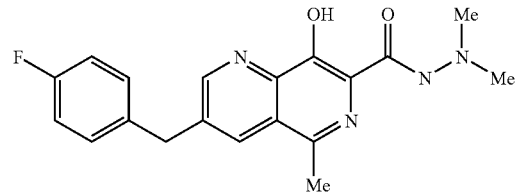

Example B-17

3-(4-fluorobenzyl)-8-hydroxy-5-methyl[1,6]naphthyridine-7-carboxylic acid N',N'-dimethylhydrazide Melting point: 137-139° C.
Elemental analysis for C$_{19}$H$_{19}$FN$_4$O$_2$
Calcd.(%): C, 64.40; H, 5.40; F, 5.36; N, 15.81.
Found.(%): C, 64.14; H, 5.30; F, 5.24; N, 15.51.
NMR (CDCl$_3$) d: 2.76 (3H, s), 2.80 (6H, s), 4.22 (2H, s), 7.01-7.06 (2H, m), 7.16-7.21 (2H, m), 8.03 (1H, m), 8.80 (1H, bs), 9.02 (1H, d, J=2.1 Hz), 12.91 (1H, bs).

Example B-18

According to the method of Example B-3, Compound B-18 was synthesized.

[Formula 21]

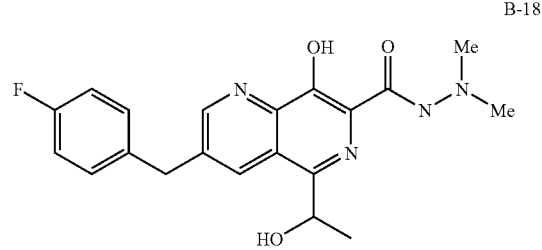

Example B-18

3-(4-fluorobenzyl)-8-hydroxy-5-(1-hydroxyethyl)[1,6]naphthyridine-7-carboxylic acid N',N'-dimethylhydrazide Melting point: 114-116° C.
Elemental analysis for C$_{20}$H$_{21}$FN$_4$O$_3$·0.9H$_2$O
Calcd.(%): C, 59.96; H, 5.74; F, 4.74; N, 13.99.
Found.(%): C, 60.05; H, 5.68; F, 4.94; N, 13.70.
NMR (CDCl$_3$) d: 1.57 (3H, d, J=6.3 Hz), 2.82 (6H, s), 3.59 (1H, bs), 4.22 (2H, s), 5.39 (1H, d, J=5.4 Hz), 7.01-7.07 (2H, m), 7.16-7.20 (2H, m), 8.04 (1H, s), 8.57 (1H, bs), 9.04 (1H, s), 13.16 (1H, bs).

Example B-19 to B-20

According to the method of Example B-4, Compounds B-19 to 20 were synthesized.

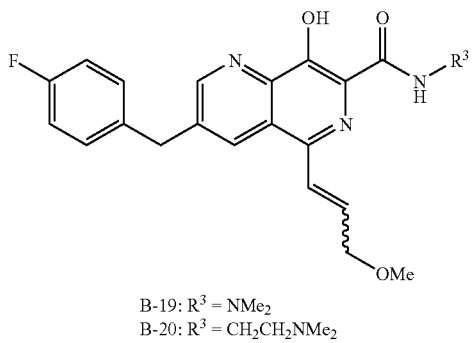

B-19: R³ = NMe₂
B-20: R³ = CH₂CH₂NMe₂

Example B-19

3-(4-fluorobenzyl)-8-hydroxy-5-(3-methoxypropenyl)[1,6]naphthyridine-7-carboxylic acid N',N'-dimethylhydrazide Melting point: 115-116° C.
Elemental analysis for $C_{22}H_{23}FN_4O_3$
Calcd.(%): C, 64.38; H, 5.65; F, 4.63; N, 13.65.
Found.(%): C, 64.23; H, 5.65; F, 4.35; N, 13.34.
NMR (CDCl₃) d: 2.82 (6H, s), 3.49 (3H, s), 4.21 (2H, s), 4.24 (1H, d, J=1.8 Hz), 4.26 (1H, d, J=1.8 Hz), 6.86-6.94 (1H, m), 7.00-7.06 (2H, m), 7.15-7.25 (3H, m), 8.24 (1H, d, J=1.84 Hz), 8.77 (1H, bs), 9.01 (1H, d, J=1.8 Hz), 13.07 (1H, bs).

Example B-20

3-(4-fluorobenzyl)-8-hydroxy-5-(3-methoxypropenyl)[1,6]naphthyridine-7-carboxylic acid (2-dimethylaminoethyl)amide hydrochloride monohydrate Melting point: 156-158° C.
Elemental analysis for $C_{24}H_{27}FN_4O_3 \cdot HCl \cdot H_2O$
Calcd.(%): C, 58.47; H, 6.13; Cl, 7.19; F, 3.85; N, 11.37.
Found.(%): C, 58.39; H, 16.16; Cl, 7.22; F, 3.99; N, 11.36.
NMR (d6-DMSO)) d: 2.85 (6H, s), 3.38 (3H, s), 3.74-3.76 (2H, m), 4.23-4.27 (4H, m), 7.13-7.18 (2H, m), 7.30-7.52 (4H, m), 8.79 (1H, s), 9.07 (1H, m), 9.32-9.36 (1H, m), 9.80 (1H, bs), 13.35 (1H, bs).

Example B-21 to B-24

According to the method of Example A-4, Compounds B-21 to B-24 were synthesized.

[Formula 23]

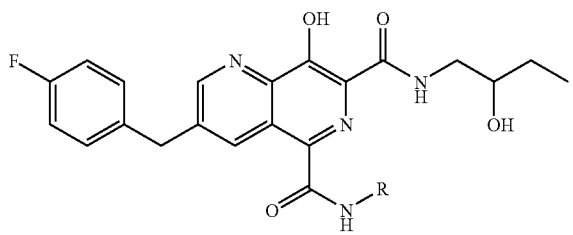

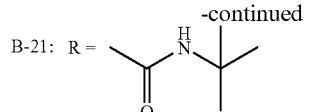

B-21: R =

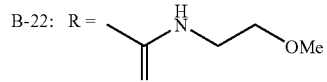

B-22: R =

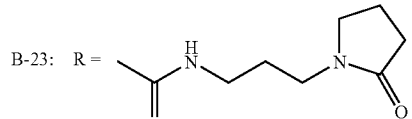

B-23: R =

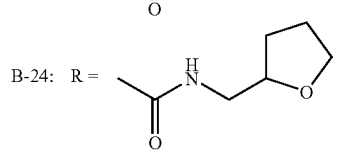

B-24: R =

Example B-21

3-(4-fluorobenzyl)-8-hydroxy[1,6]naphthyridine-5,7-dicarboxylic acid 5-tert-butylamide 7-[(2-hydroxybutyl)amide]

NMR (CDCl₃) d: 1.05 (3H, t, J=7.5 Hz), 1.53 (9H, s), 1.58-1.74 (2H, m), 3.30-3.40 (1H, m), 3.79-3.90 (2H, m), 4.20 (2H, s), 6.96-7.04 (2H, m), 7.16-7.21 (2H, m), 7.52 (1H, s), 8.13-8.17 (1H, m), 8.98 (1H, d, J=2.2 Hz), 9.78 (1H, d, J=2.2 Hz), 13.59 (1H, br s).

Example B-22

3-(4-fluorobenzyl)-8-hydroxy[1,6]naphthyridine-5,7-dicarboxylic acid 7-[(2-hydroxybutyl)amide]

5-[(2-methoxyethyl)amide]

NMR (CDCl₃) d: 1.05 (3H, d, J=7.5 Hz), 1.54-1.70 (2H, m), 3.33-3.42 (1H, m), 3.42 (3H, s), 3.60-3.64 (2H, m), 3.66-3.72 (2H, m), 3.76-3.91 (2H, m), 4.19 (2H, s), 6.97-7.04 (2H, m), 7.16-7.21 (2H, m), 8.05-8.11 (1H, m), 8.29-8.36 (1H, m), 8.98 (1H, d, J=2.1 Hz), 9.70 (1H, d, J=2.1 Hz), 13.69 (1H, br s).

Example B-23

3-(4-fluorobenzyl)-8-hydroxy[1,6]naphthyridine-5,7-dicarboxylic acid 7-[(2-hydroxybutyl)amide]5-{[3-(2-oxopyrrolidine-1-yl)propyl]amide}

NMR (CDCl₃) d: 1.03 (3H, d, J=7.4 Hz), 1.54-1.64 (2H, m), 1.78-1.86 (2H, m), 2.08-2.19 (2H, m), 2.53-2.56 (2H, m), 3.33-3.56 (7H, m), 3.73-3.85 (2H, m), 4.20 (2H, s), 6.95-7.04 (2H, m), 7.17-7.22 (2H, m), 9.00 (1H, d, J=2.1 Hz), 9.04-9.11 (1H, m), 9.19 (1H, t, J=6.3 Hz), 9.94 (1H, d, J=2.1 Hz), 14.03 (1H, s).

Example B-24

3-(4-fluorobenzyl)-8-hydroxy[1,6]naphthyridine-5,7-dicarboxylic acid 7-[(2-hydroxybutyl)amide]

5-[(tetrahydrofuran-2-ylmethyl)amide]

NMR (CDCl₃) d: 1.05 (3H, t, J=7.5 Hz), 1.56-1.72 (2H, m), 1.90-2.01 (3H, m), 2.01-2.18 (1H, m), 3.31-3.43 (2H, m), 3.76-3.98 (5H, m), 4.09-4.20 (1H, m), 4.20 (2H, s), 6.97-7.04 (2H, m), 7.16-7.22 (2H, m), 8.11-8.18 (1H, m), 8.41 (1H, br s), 8.99 (1H, d, J=2.0 Hz), 9.73 (1H, s), 13.67 (1H, br s).

Example B-25 to B-29

According to the method of Example A-3, Compounds B-25 to B-29 were synthesized.

[Formula 24]

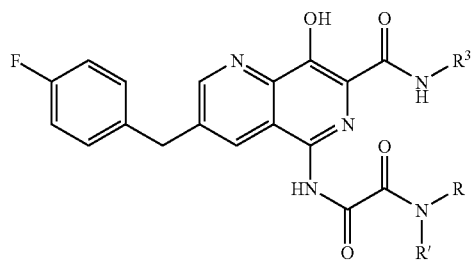

B-25: R³ = —NMe₂, R = —CH₂CH₂OMe, R' = —H
B-26: R³ = —NMe₂, R = —Me, R' = —Me,
B-27: R³ = —CH₂CH₂OH, R = —Me, R' = —H
B-28: R³ = —CH(Me)CH₂OH, R = —Me, R' = —H
B-29: R³ = —CH₂CH₂CH₂NMe₂, R = —Me, R' = —H

Example B-25

N-[7-(N',N'-dimethylhydrazinocarbonyl)-3-(4-fluorobenzyl)-8-hydroxy[1,6]naphthyridine-5-yl]-N'-(2-methoxyethyl)oxalamide Melting point: 167-169° C.
NMR (CDCl₃) d: 2.79 (6H, s), 3.43 (3H, s), 3.55-3.67 (4H, m), 4.21 (2H, s), 6.99-7.06 (2H, m), 7.15-7.20 (2H, m), 7.74-7.80 (1H, m), 7.94 (1H, d, J=1.4 Hz), 8.52 (1H, br s), 9.03 (1H, d, J=2.1 Hz), 9.63 (1H, s), 13.08 (1H, brs).

Example B-26

N-[7-(N',dimethylhydrazinocarbonyl)-3-(4-fluorobenzyl)-8-hydroxy[1,6]naphthyridine-5-yl]-N',N'-dimethyl oxalamide Melting point: 125-128° C.
NMR (CDCl₃) d: 2.78 (6H, s), 3.13 (3H, s), 3.43 (3H, s) 4.21 (2H, s), 6.98-7.06 (2H, m), 7.15-7.21 (2H, m), 7.88 (1H, s), 8.56 (1H, br s), 9.04 (1H, d, J=2.0 Hz), 9.66 (1H, br s), 13.07 (1H, br s).

Example B-27

N-[3-(4-fluorobenzyl)-8-hydroxy-7-(2-hydroxyethylcarbamoyl)[1,6]naphthyridine-5-yl]-N'-methyl oxalamide Melting point: 136-137° C.
NMR (CDCl₃) d: 3.02 (3H, d, J=5.2 Hz), 3.65-3.71 (2H, m), 3.87-3.93 (2H, m), 4.19 (2H, s), 6.98-7.05 (2H, m), 7.13-7.19 (2H, m), 7.53 (1H, d, J=5.2 Hz), 7.92 (1H, s), 8.17-8.23 (1H, m), 9.01 (1H, d, J=2.0 Hz), 13.19 (1H, s).

Example B-28

N-[3-(4-fluorobenzyl)-8-hydroxy-7-(2-hydroxy-1-methylethylcarbamoyl)[1,6]naphthyridine-5-yl]-N'-methyl oxalamide Melting point: 131-133° C.
NMR (CDCl₃) d: 1.36 (3H, d, J=6.7 Hz), 3.03 (3H, d, J=5.2 Hz), 3.71 (1H, dd, J=11.1, 5.9 Hz), 3.84 (1H, dd, J=11.1, 3.8 Hz), 4.19 (2H, s), 4.26-4.35 (1H, m), 6.98-7.06 (2H, m), 7.14-7.19 (2H, m), 7.49 (1H, d, J=5.2 Hz), 7.92 (1H, d, J=2.0 Hz), 9.02 (1H, d, J=2.0 Hz), 9.65 (1H, s), 13.21 (1H, s).

Example B-29

N-[7-(3-dimethylaminopropylcarbamoyl)-3-(4-fluorobenzyl)-8-hydroxy[1,6]naphthyridine-5-yl]-N'-methyl oxalamide NMR (CDCl₃) d: 1.83 (2H, m), 2.33 (6H, s), 2.49-2.55 (2H, m), 3.03 (3H, d, J=5.2 Hz), 3.54-3.63 (2H, m), 4.19 (2H, s), 6.98-7.05 (2H, m), 7.13-7.19 (2H, m), 7.49 (1H, br s), 7.94 (1H, s), 8.86 (1H, br s), 9.02 (1H, s), 9.62 (1H, br s), 13.52 (1H, br s).

Example B-30

The following compounds were synthesized.

[Formula 25]

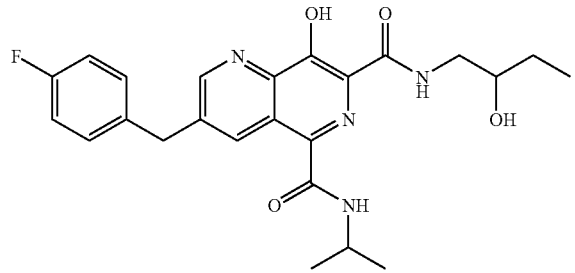

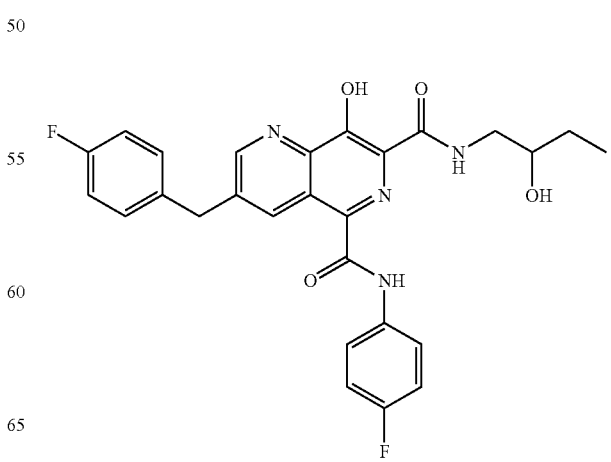

59
-continued
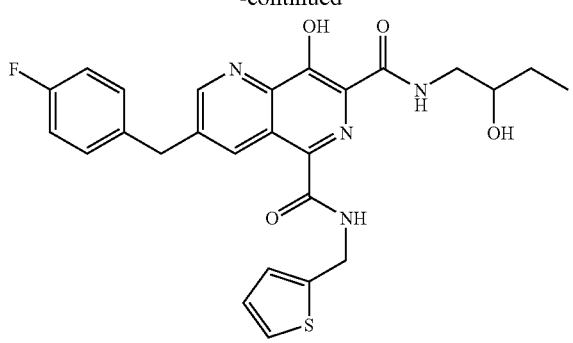
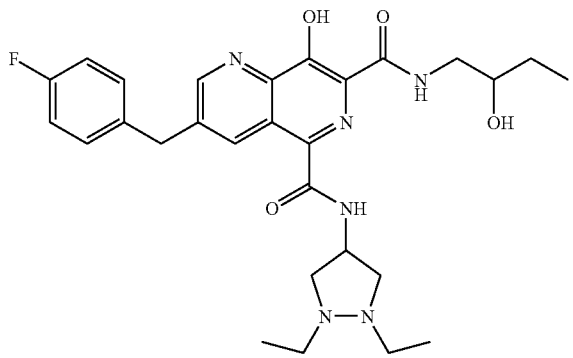
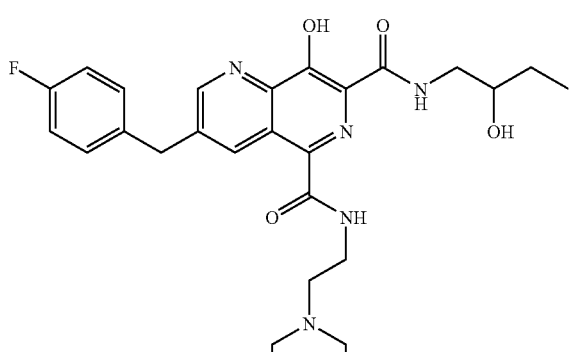
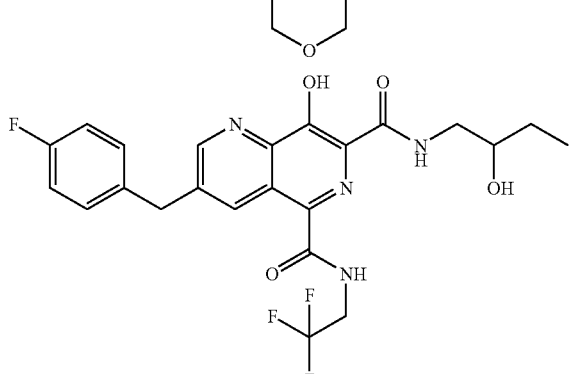
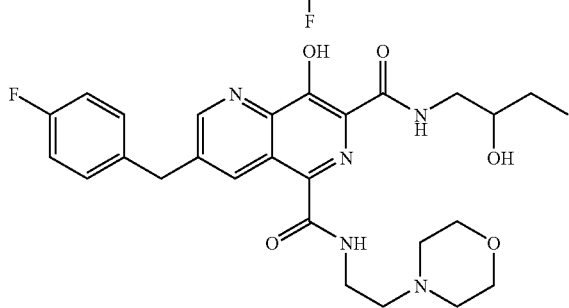
60
-continued
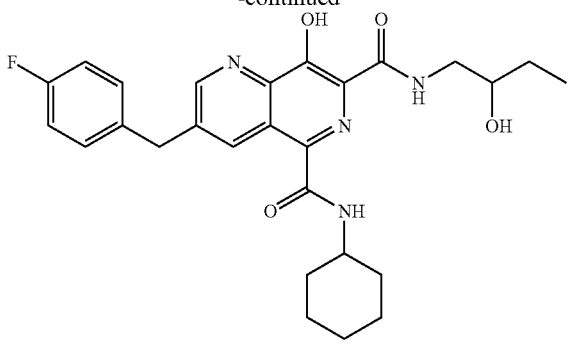
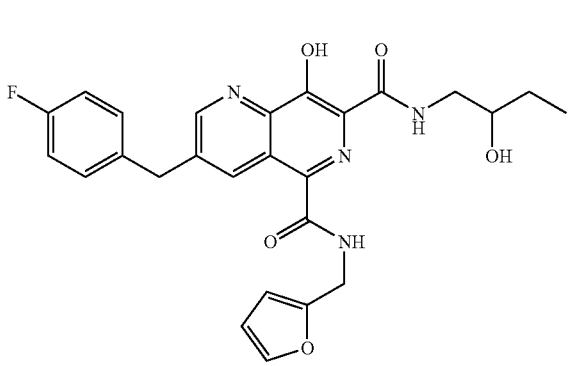
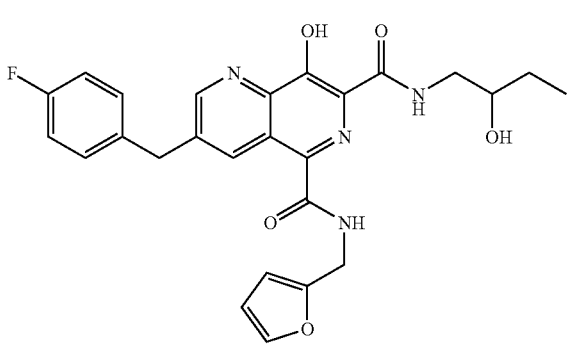
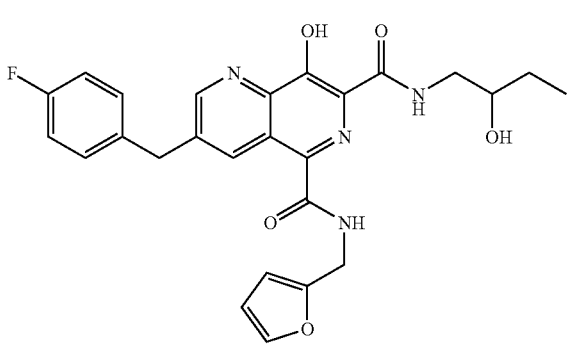
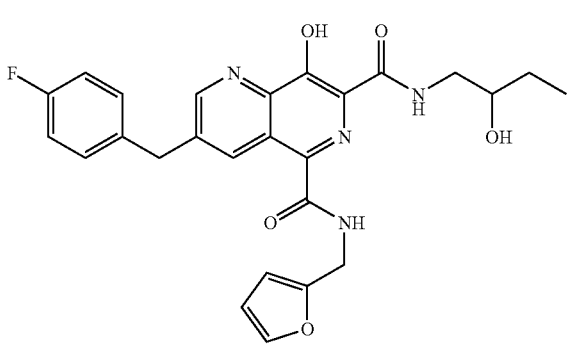

-continued
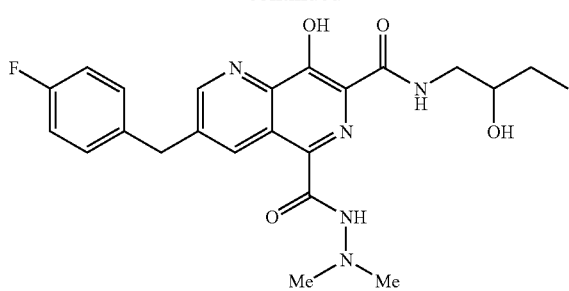
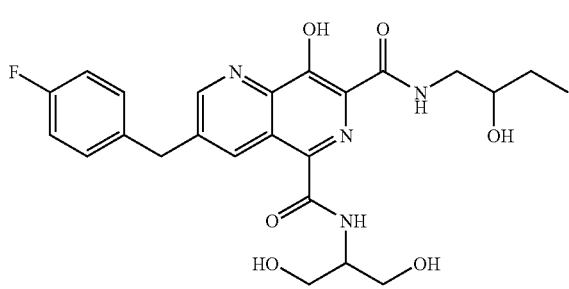
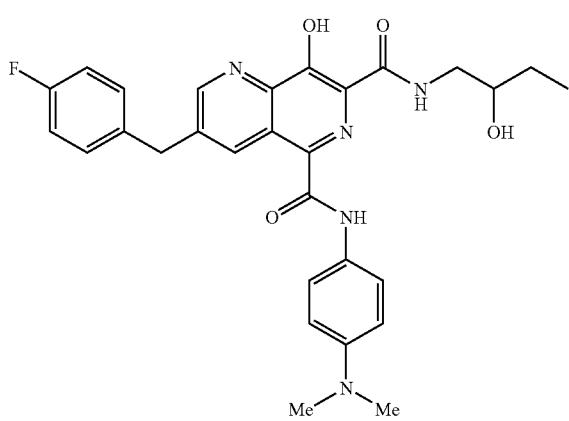
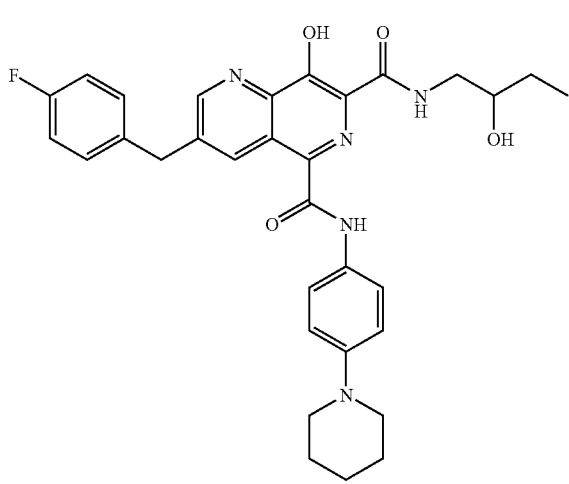
-continued
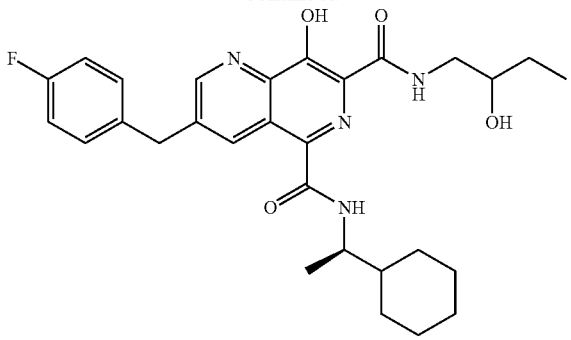
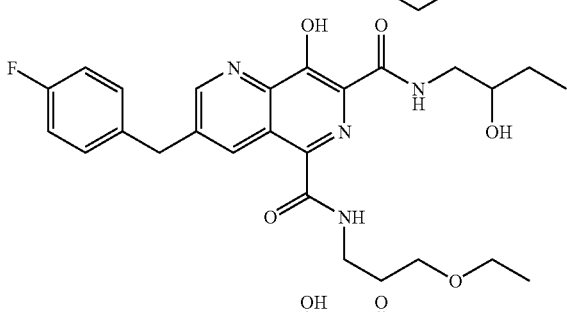
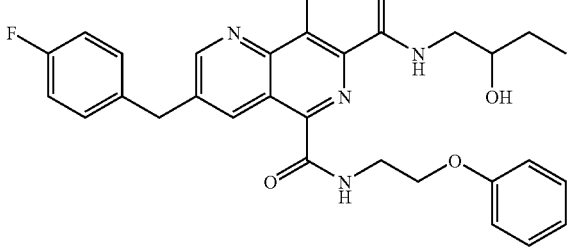
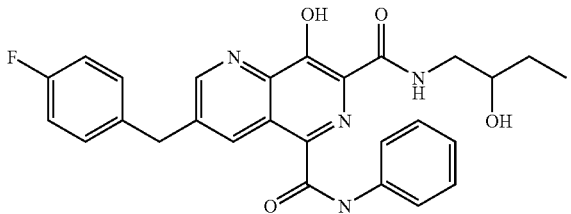
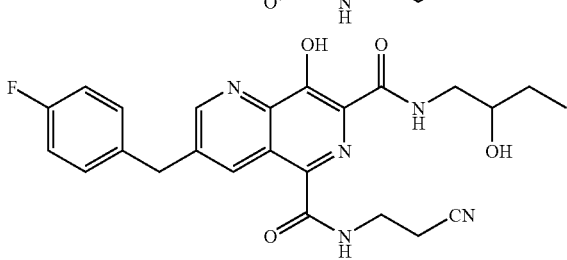
[Formula 26]
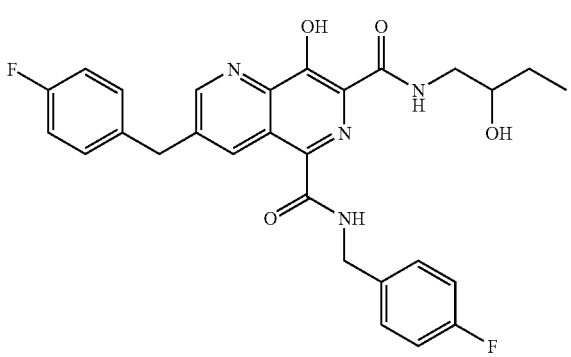

63
-continued
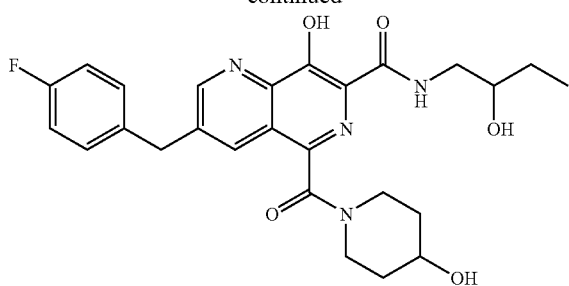
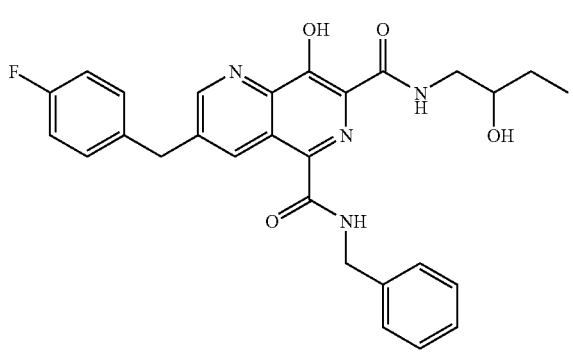
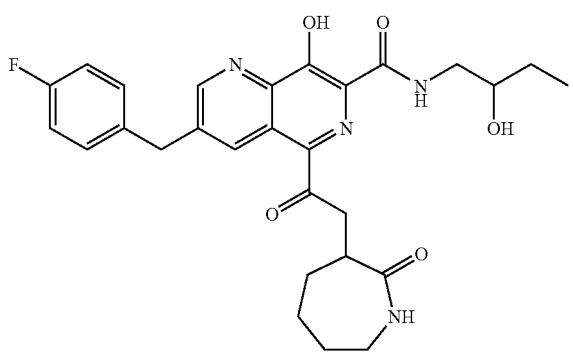
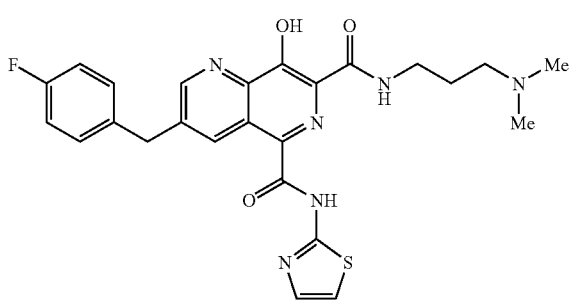
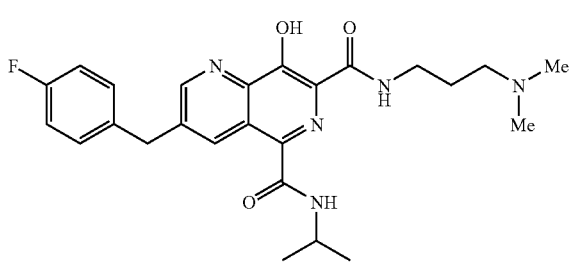
64
-continued
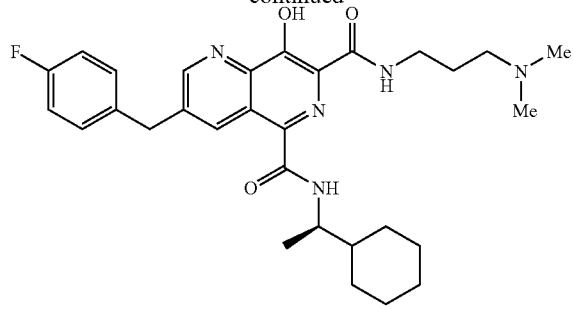
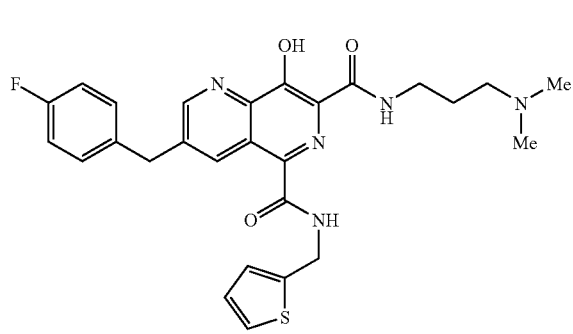
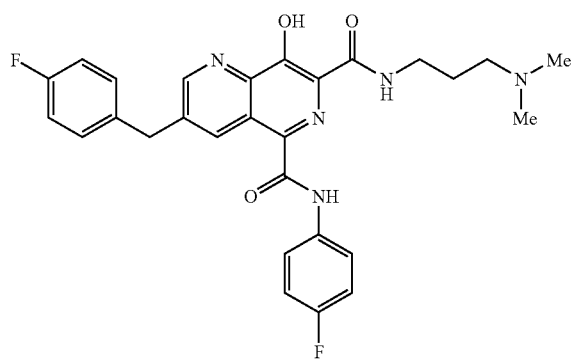
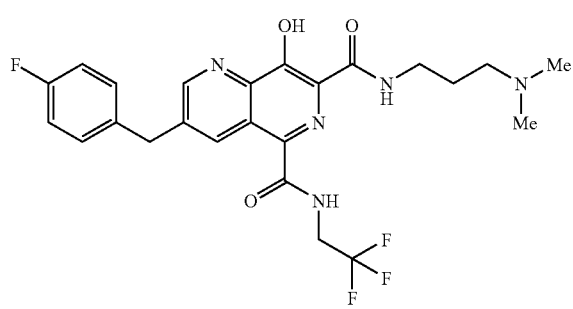
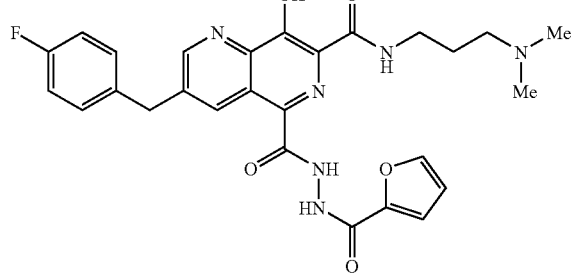

65
-continued
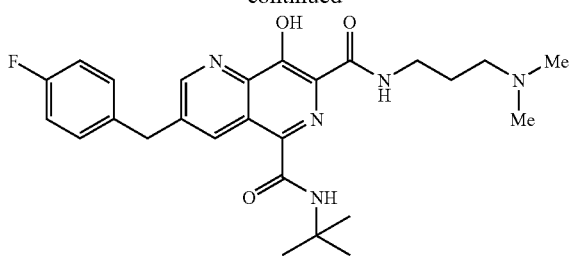
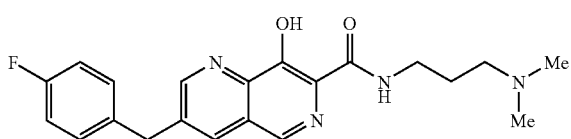
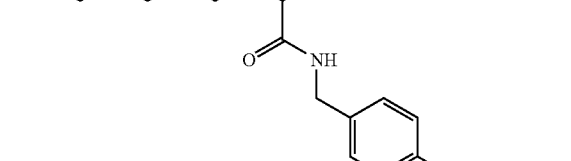
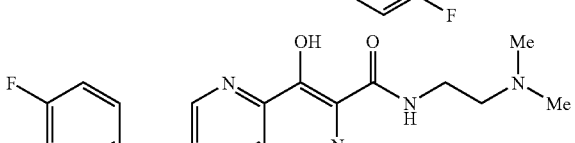
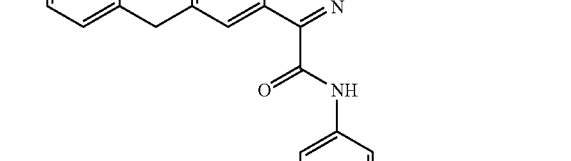
66
-continued
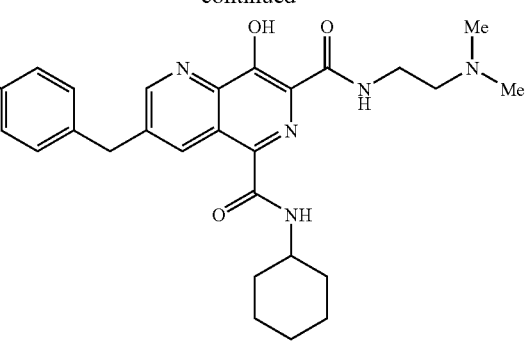
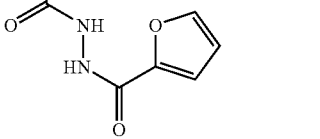
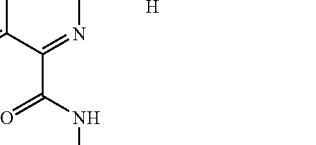
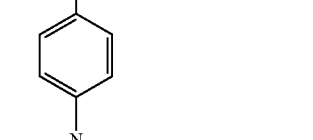

-continued
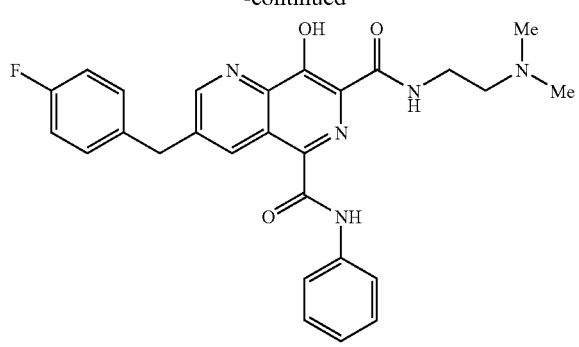
[Formula 27]
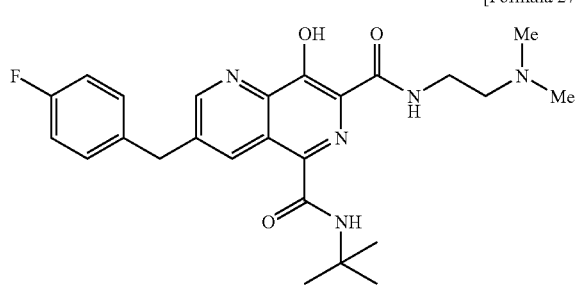
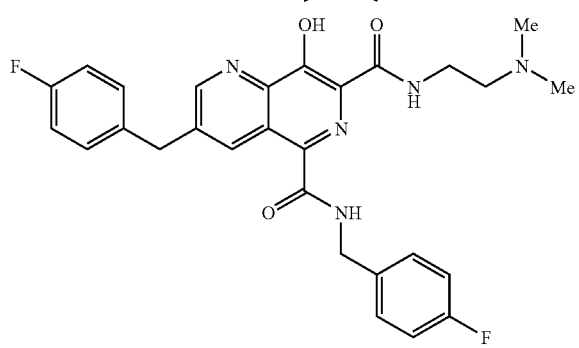
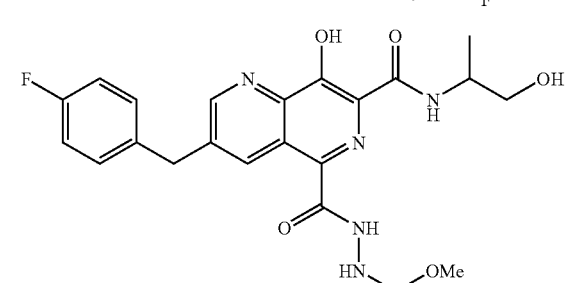
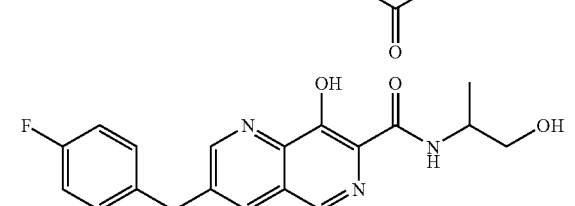
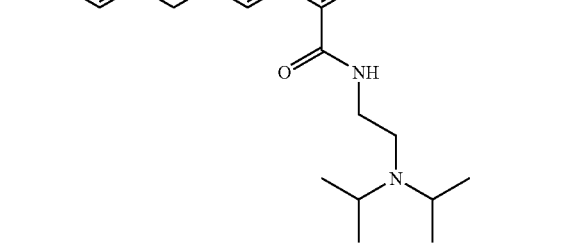
-continued
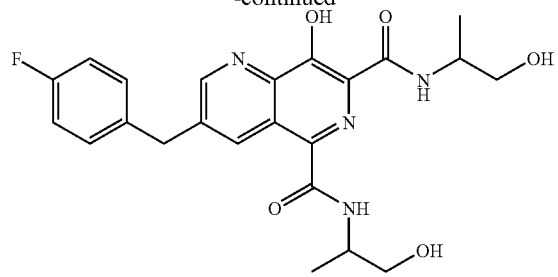
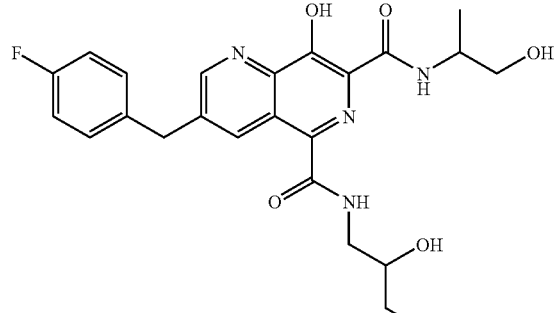
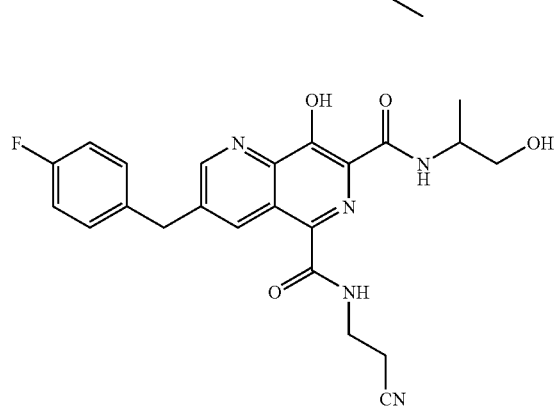
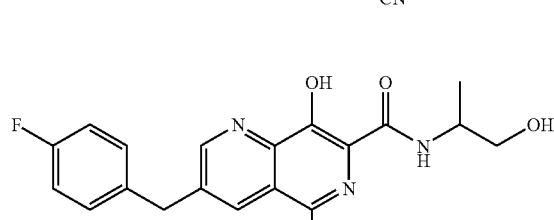
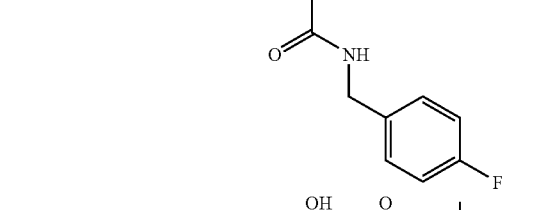
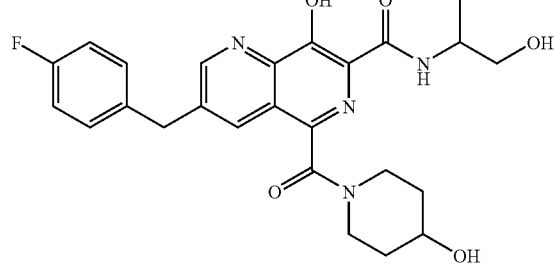

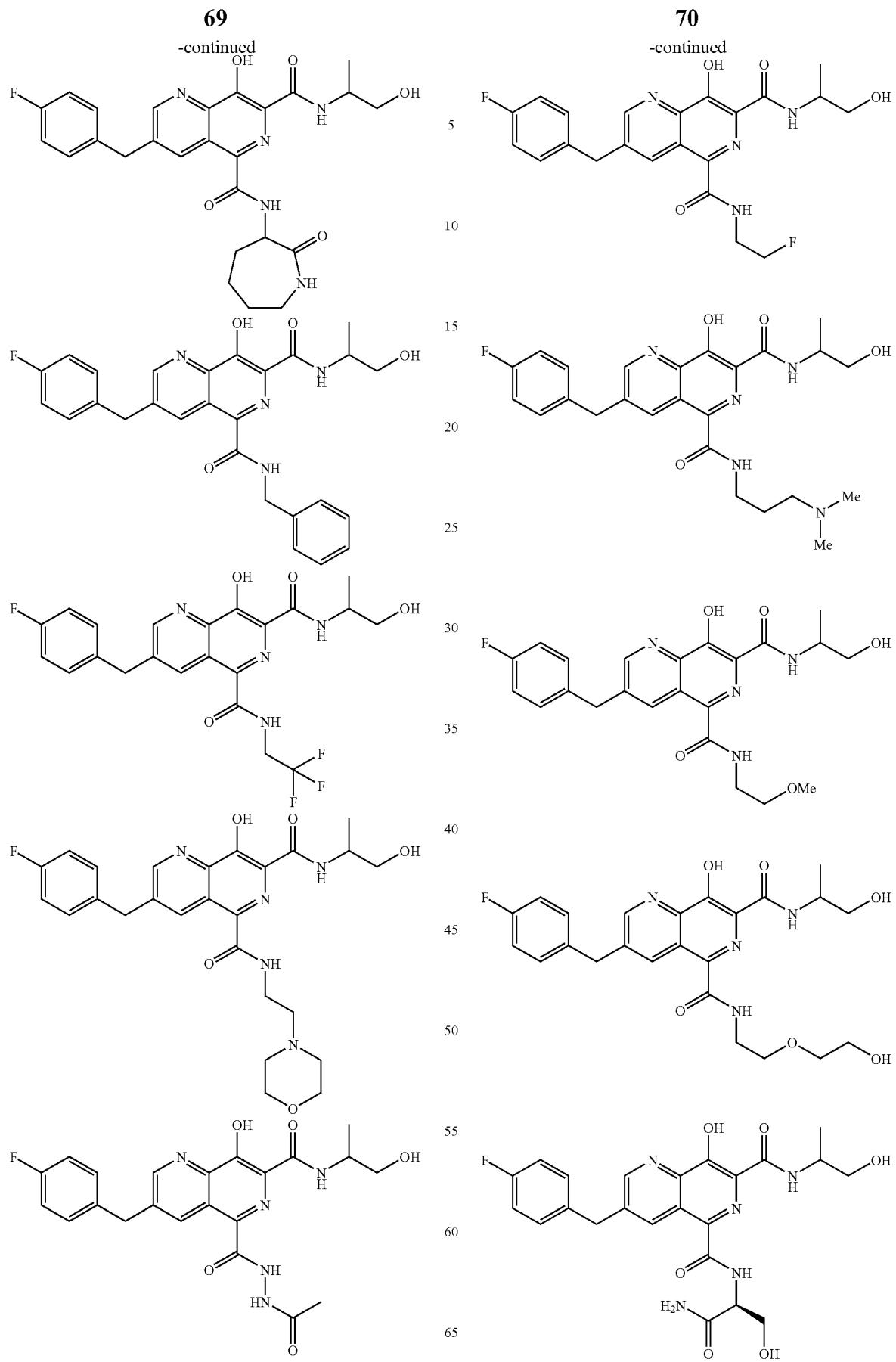

71
-continued
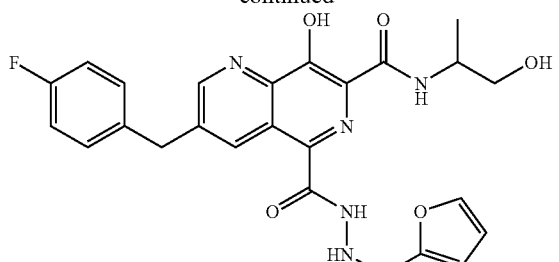
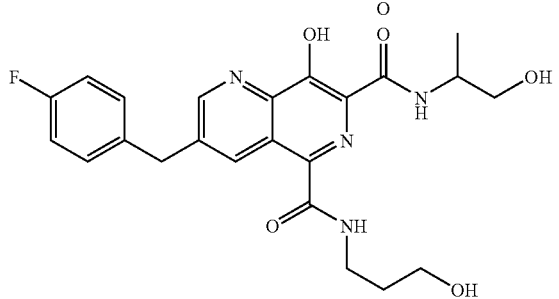
[Formula 28]
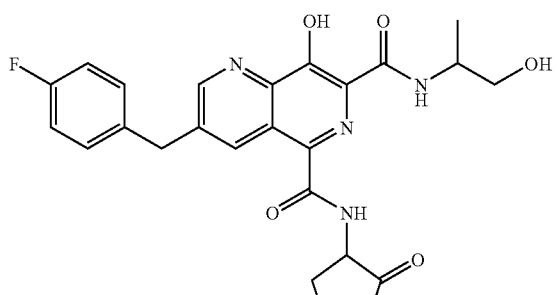
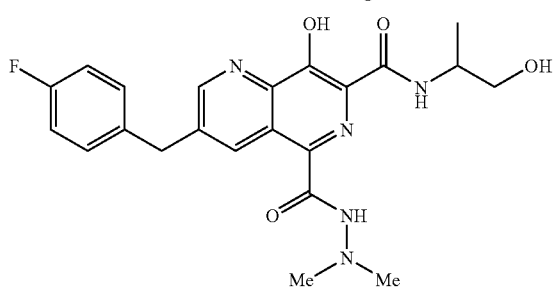
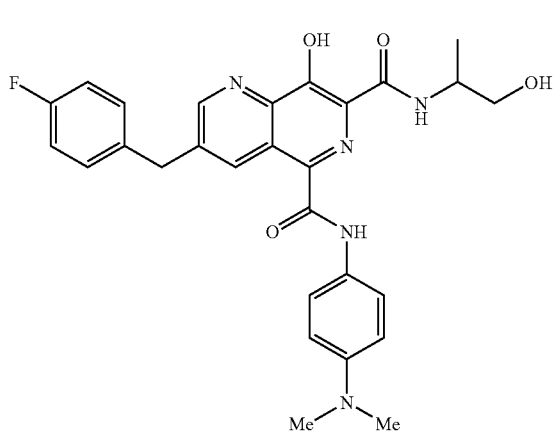
72
-continued
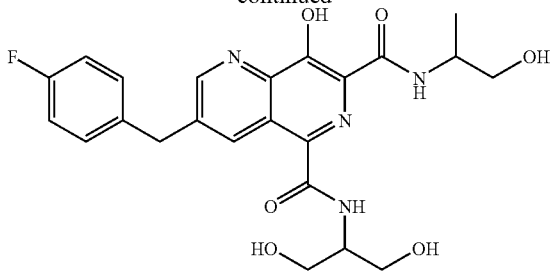
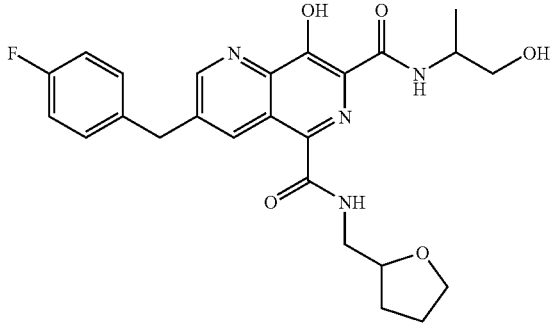
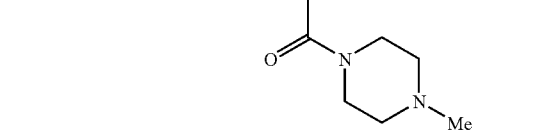
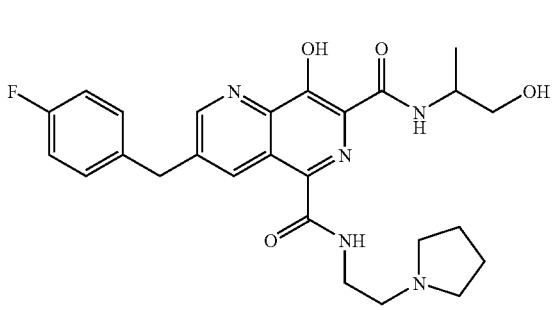
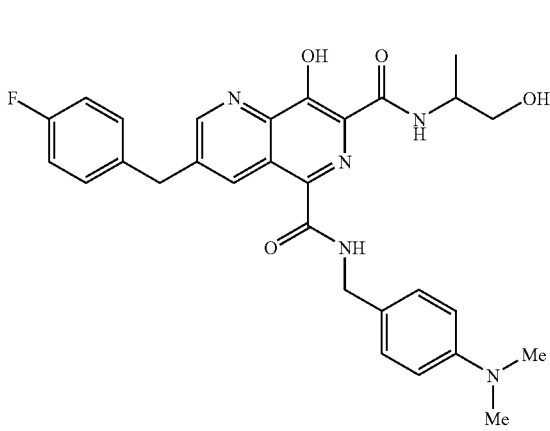

Experimental Example 1

The inhibitory activities against integrase were determined by the assay described below.

(1) Preparation of DNA Solutions

A substrate DNA solution (2 pmol/µl) and a target DNA solution (5 pmol/µl) were prepared in the manner as described in Experimental example 1 of WO 2004/024693. Before using the DNA solutions, complementary chains were annealed by slowly cooling after boiling. Substrate DNA and target DNA had sequences as described in that Experimental example.

(2) Determination of Inhibition Rate ($IC_{50}$ Values)

Streptavidin, obtained from Vector Laboratories, was dissolved in 0.1 M carbonate buffer (composition: 90 mM $Na_2CO_3$, 10 mM $NaHCO_3$) at concentration of 40 µg/ml. After coating each well of immunoplates (obtained from NUNC) with 50 µl of the above solution at 4° C. over night, each well was washed twice with PBS (composition: 13.7 mM NaCl, 0.27 mM KCl, 0.43 mM $Na_2HPO_4$, 0.14 mM $KH_2PO_4$) and blocked with 300 µl of 1% skim milk in PBS for 30 min. Additionally, each well was washed twice with PBS and added 50 µl of substrate DNA solution (2 pmol/µl). The immunoplates were kept at room temperature for 30 min while shaking. Then, each well was washed twice with PBS and once with the distilled water.

Subsequently, in the each well prepared above were added 51 µl of the reaction solution prepared from 12 µl of the buffer (composition: 150 mM MOPS (pH7.2), 75 mM $MnCl_2$, 50 mM 2-mercaptoethanol, 25% glycerol, 500 µg/ml bovine serum albumin-fraction V), and 39 µl of the distilled water. Then 9 µl of an integrase solution (30 pmol) was added and mixed well. In the well of negative control (NC) was added 9 µl of the integrase dilution buffer (composition: 20 mM MOPS (pH7.2), 400 mM potassium glutamate, 1 mM EDTA, 0.1% NP-40, 20% glycerol, 1 mM DTT, 4M urea), and mixed well using a plate mixer.

The plates were incubated at 30° C. for 60 minutes. The reaction solution was removed and washed three times with 250 µl of washing buffer (composition: 150 mM MOPS (pH7.2), 50 mM 2-mercaptoethanol, 25% glycerol, 500 µg/ml bovine serum albumin-fraction V).

Then each well was added with 53 µl of reaction solution prepared from 12 µl of buffer (composition: 150 mM MOPS (pH7.2), 75 mM $MgCl_2$, 50 mM 2-mercaptoethanol, 25% glycerol, 500 µg/ml bovine serum albumin-fraction V) and 41 µl of distilled water. Further, each well was added with 6 µl of DMSO solution of a compound to be tested, and the well of positive control (PC) was added with 6 µl of DMSO, and mixed well by a plate mixer. After incubating the plate for 30 minutes at 30° C., was added 1 µl of target DNA (5 pmol/µl), and mixed well by a plate mixer.

After incubation for 10 minutes at 30° C., each plate was washed twice with PBS after removal of the reaction solution. Then, 100 µl of ×2000 diluted solution of anti-digoxigenin antibody labeled with alkaline phosphatase (sheep Fab fragment: Boehringer) was added allowed to bind for 1 hour at 30° C., and washed twice with PBS containing 0.05% Tween20 and once with PBS in this sequence. Next, 150 µl of the Alkaline phosphatase coloring buffer (composition: 10 mM p-Nitrophenylphosphate (obtained from Vector Laboratories), 5 mM $MgCl_2$, 100 mM NaCl, 100 mM Tris-HCl (pH 9.5)) was added and allowed to react for 2 hours at 30° C. Then the reaction was terminated by the addition of 50 µl of 1N NaOH solution. The optical density at 405 nm ($OD_{405nm}$) of each well was measured and the inhibition rate ($IC_{50}$) was determined by the following expression.

The inhibition rate(%)=100[1−{(C abs.−NC abs.)/(PC abs.−NC abs.)}]

C abs.; the OD of the well of the compound
NC abs.: the OD of the negative control (NC)
PC abs.: the OD of the positive control (PC)

Experimental Example 2

The inhibitory activities against HIV cell proliferation were determined by the assay method described below.

(1) HIV (HTLV-IIIB strain) persistence infection human T-cell strain Molt-4 clone 8 was cultured on RPMI-1640 medium supplemented with 10% fetal bovine serum, and the supernatant was measured for viral titer after filtration, and stored at −80° C. On the other hand, each anti-HIV active agent was diluted in the above culture medium to a predetermined concentration, and each well of a 96-well microplate was added with 50 µl of the resultant active agent solution. Then, 100 µl ($3.5×10^4$ cells) each of MT-4 cell suspension was poured into each well, followed by each 50 µl (60 pfu (plaque forming unit)) of the HIV-containing supernatant diluted with the above culture medium.

(2) After incubating for 4 days in a carbon dioxide incubator at 37° C., every well was added with 30 µl of 3-(4,5-dimethylthiazole-2-yl)-2,5-diphenyltetrazolium bromide (MTT) 5 mg/ml), PBS, and incubated for another 1 hour. At this time, since living cells reduce MTT to cause precipitation of formazane, 150 µl of cell supernatant was removed from each well, and instead 150 µl of lysis solution (isopropanol supplemented with 10% Triton X-100 and 0.4% (v/v) HCl) was added, to make formazane eluate by shaking with a plate mixer. Formazane was observed with OD 560 nm and 690 nm (reference wavelength) using a micro reader, and the results were compared with the references. The concentration of Compound at which 50% of cytopathy caused by viruses was inhibited was defined as $EC_{50}$.

The results of the above experiment are shown below.

TABLE 8

| Example (Compound No.) | Experimental example 1 ($IC_{50}$, µg/ml) |
|---|---|
| A-1 | 0.0024 |
| A-2 | 0.019 |
| A-3 | 0.019 |
| A-5 | 0.0045 |
| A-6 | 0.0056 |
| A-9 | 0.060 |
| A-10 | 0.068 |
| B-1 | 0.011 |
| B-2 | 0.0074 |
| B-3 | 0.0068 |
| B-4 | 0.0048 |
| B-5 | 0.018 |
| B-6 | 0.072 |
| B-7 | 0.015 |
| B-8 | 0.012 |
| B-9 | 0.017 |
| B-10 | 0.022 |
| B-11 | 0.024 |
| B-12 | 0.079 |
| B-13 | 0.033 |
| B-14 | 0.022 |
| B-15 | 0.021 |
| B-16 | 0.026 |
| B-17 | 0.006 |
| B-18 | 0.017 |
| B-19 | 0.0046 |

TABLE 8-continued

| Example (Compound No.) | Experimental example 1 ($IC_{50}$, μg/ml) |
|---|---|
| B-20 | 0.017 |
| B-21 | 0.0084 |
| B-22 | 0.017 |
| B-23 | 0.019 |
| B-24 | 0.015 |
| B-25 | 0.019 |
| B-26 | 0.018 |
| B-27 | 0.018 |
| B-28 | 0.021 |
| B-29 | 0.025 |

Formulation Example

The term "active ingredient" means the compounds of the present invention, the tautomers, the prodrugs thereof, their pharmaceutical acceptable salts, or their solvate.

Formulation Example 1

Hard gelatin capsules are prepared using of the following ingredients:

| | Dose (mg/capsule) |
|---|---|
| Active ingredient | 250 |
| Starch, dried | 200 |
| Magnesium stearate | 10 |
| Total | 460 mg |

Formulation Example 2

A tablet is prepared using of the following ingredients:

| | Dose (mg/tablet) |
|---|---|
| Active ingredient | 250 |
| Cellulose, microcrystals | 400 |
| Silicon dioxide, fumed | 10 |
| Stearic acid | 5 |
| Total | 665 mg |

The components are blended and compressed to form tablets each weighing 665 mg.

Formulation Example 3

An aerosol solution is prepared containing the following components:

| | Weight |
|---|---|
| Active ingredient | 0.25 |
| Ethanol | 25.75 |
| Propellant 22 (chlorodifluoromethane) | 74.00 |
| Total | 100.00 |

The active ingredient is mixed with ethanol and the admixture added to a portion of the propellant 22, cooled to −30° C. and transferred to a filling device. The required amount is then fed to a stainless steel container and diluted with the reminder of the propellant. The valve units are then fitted to the container.

Formulation Example 4

Tablets, each containing 60 mg of active ingredient, are made as follows.

| | |
|---|---|
| Active ingredient | 60 mg |
| Starch | 45 mg |
| Microcrystals cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve, and the mixed thoroughly. The aqueous solution containing polyvinylpyrrolidone is mixed with the resultant powder, and the admixture then is passed through a No. 14 mesh U.S. sieve. The granules so produced are dried at 50° C. and passed through a No. 18 mesh U.S. sieve. The sodium carboxymethyl starch, magnesium stearate, and talc, previously passed through No. 60 mesh U.S. sieve, are then added to the granules which, after mixing, are compressed on a tablet machine to yield tablets each weighing 150 mg.

Formulation Example 5

Capsules, each containing 80 mg of active ingredient, are made as follows:

| | |
|---|---|
| Active ingredient | 80 mg |
| Starch | 59 mg |
| Microcrystals cellulose | 59 mg |
| Magnesium stearate | 2 mg |
| Total | 200 mg |

The active ingredient, starch, cellulose, and magnesium stearate are blended, passed through a No. 45 mesh U.S. sieve, and filled into hard gelatin capsules in 200 mg quantities.

Formulation Example 6

Suppositories, each containing 225 mg of active ingredient, are made as follows:

| | |
|---|---|
| Active ingredient | 225 mg |
| Saturated fatty acid glycerides | 2000 mg |
| Total | 2225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation Example 7

Suspensions, each containing 50 mg of active ingredient, are made as follows:

| Active ingredient | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 U.S. sieve, and mixed with the sodium carboxymethyl cellulose and syrup to form a smooth paste. The benzoic acid solution and flavor are diluted with a portion of the water and added, with stirring. Sufficient water is then added to produce the required volume.

Formulation Example 8

An intravenous formulation may be prepared as follows:

| Active ingredient | 100 mg |
|---|---|
| Saturated fatty acid glycerides | 1000 ml |

The solution of the above ingredients is generally administered intravenously to a subject at a rate of 1 ml per minute.

What is claimed is:
1. A compound of the formula:

[Formula 1]

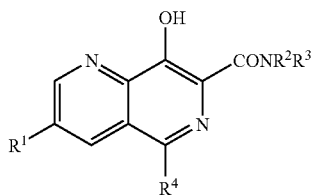

(I)

(wherein:
$R^1$ is benzyl substituted with halogen;
$R^2$ is hydrogen or lower alkyl;
$R^3$ is optionally substituted alkyl (substituent: lower alkoxy, amino optionally substituted with lower alkyl, cyano, hydroxy, carboxy, or lower alkoxycarbonyl) or optionally substituted amino (substituent: lower alkyl);
$R^4$ is optionally substituted carboxy (substituent: lower alkyl, hydroxy lower alkyl, lower alkoxy lower alkyl, optionally substituted amino lower alkyl, or an optionally substituted heterocyclic group), optionally substituted formylamino (substituent: lower alkyl, hydroxy lower alkyl, lower alkoxy lower alkyl, optionally substituted carbamoyl lower alkyl, optionally substituted lower alkoxy, optionally substituted amino, or optionally substituted carbamoyl), optionally substituted carbamoyl (substituent: lower alkyl, optionally substituted lower alkyl (substituent: hydroxy, lower alkoxy, optionally substituted amino, optionally substituted lower alkoxy, carbamoyl), or optionally substituted heterocyclic group lower alkyl), optionally substituted alkyl (substituent: hydroxy, halogen, an optionally substituted heterocyclic group, optionally substituted lower alkoxy, optionally substituted amino, optionally substituted carbamoyl, or optionally substituted carboxy), or optionally substituted alkenyl (substituent: hydroxy, halogen, an optionally substituted heterocyclic group, optionally substituted lower alkoxy, optionally substituted amino, optionally substituted carbamoyl, or optionally substituted carboxy)), or a pharmaceutically acceptable salt thereof (except for Compound (I-A) shown in Table 1 below)

TABLE 1

[Formula I-A]

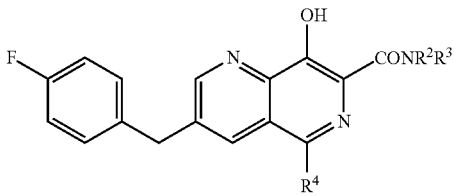

(I-A)

| Compound No. | $R^2$ | $R^3$ | $R^4$ |
|---|---|---|---|
| 20 | H | CH2CH2OMe | H |
| 27 | H | Me | NHMs |
| 28 | H | CH2CH2OMe | NHMs |
| 29 | H | i-Pr | NHMs |
| 85 | Me | Me | H |
| 86 | H | NHMe | H |
| 87 | H | NMe2 | H |
| 88 | H | OMe | H |
| 89 | H | H | H |
| 90 | H | Me | H |
| 91 | H | Et | H |
| 92 | H | i-Pr | H |
| 126 | H | CH2CH2NMe2 | H |
| 160 | H | CH2CH2OMe | NHCOCH2OMe |
| 161 | H | CH2CH2OMe | NHCOCH2CH2CO2Et |
| 162 | H | CH2CH2OMe | NHCOCH2CO2Et |
| 163 | H | CH2CH2OMe | NHCOOEt |
| 164 | H | CH2CH2OMe | NHCOCH2CH2OMe |
| 165 | H | CH2CH2OMe | NHCO-thiophene |
| 180 | H | CH2CH2OMe | Ph-CH2OH |
| 181 | H | NMe2 | Ph-CH2OH |

(Me = methyl; i-Pr = isopropyl; Et = ethyl; Ms = methanesulfonyl; thiophene = thiophene; Ph = phenyl).

2. The compound according to claim 1, wherein $R^1$ is p-fluorobenzyl, or a pharmaceutically acceptable salt thereof.

3. The compound according to claim 1, wherein $R^2$ is hydrogen; $R^3$ is $CH_2CH_2OCH_3$, $CH_2CH_2OEt$, $CH_2CH_2COOCH_3$, $CH_2CH_2CH_2OCH_3$, $CH_2CH_2CH_2O(i-Pr)$, $N(CH_3)_2$, $CH_2CH_2CN$, $CH_2CH_2N(CH_3)_2$, $CH_2CH_2N(i-Pr)_2$, $CH_2CH_2CH_2N(CH_3)_2$, $CH_2CH_2CH_2N(Et)_2$, $CH(CH_3)CH_2OH$, $CH(CH_3)COOCH_3$ or $CH_2CH(OH)CH_2CH_3$, or a pharmaceutically acceptable salt thereof.

4. The compound according to claim 1, wherein $R^4$ is a group shown below, or a pharmaceutically acceptable salt thereof

[Formula 2]

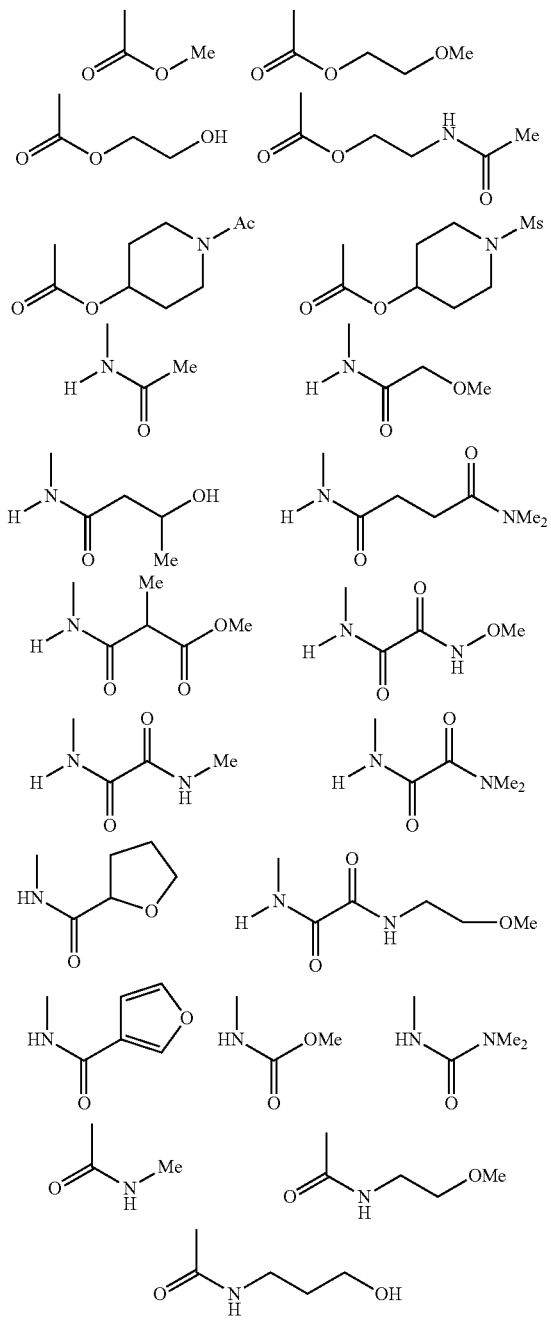
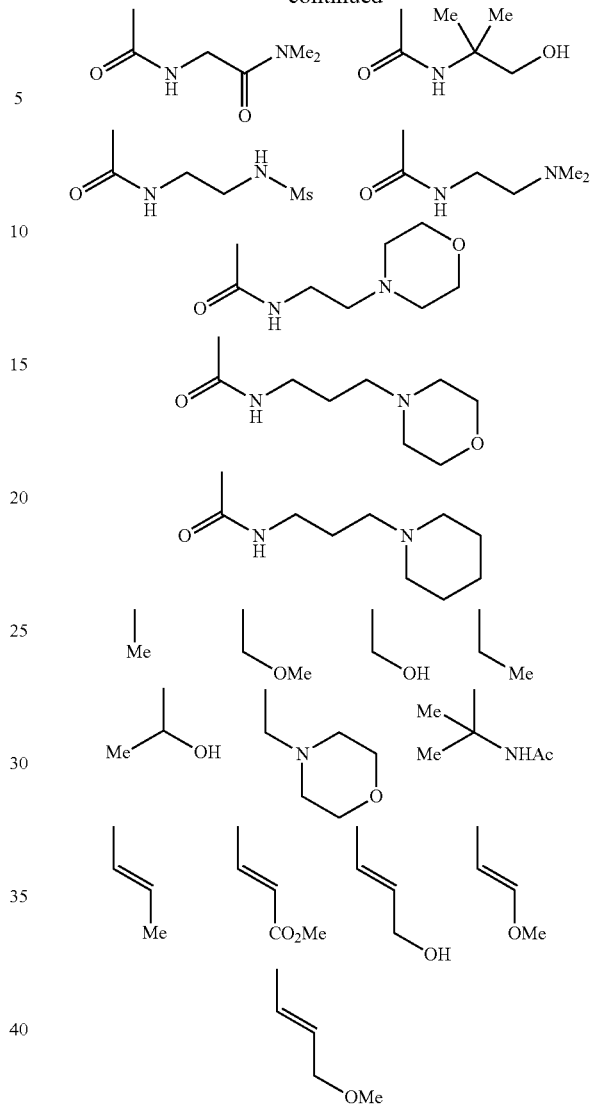

(wherein, Me is methyl; Ac is acetyl; Ms is methanesulfonyl).

5. The compound according to claim 4, wherein $R^1$ is p-fluorobenzyl, or a pharmaceutically acceptable salt thereof.

6. The compound according to claim 4, wherein $R^1$ is p-fluorobenzyl; $R^2$ is hydrogen; $R^3$ is $CH_2CH_2OCH_3$, $N(CH_3)_2$, $CH_2CH_2CN$, $CH_2CH_2N(CH_3)_2$, $CH_2CH_2CH_2N(CH_3)_2$, or $CH_2CH(OH)CH_2CH_3$; or a pharmaceutically acceptable salt thereof.

* * * * *